United States Patent
Efe et al.

(10) Patent No.: US 9,376,664 B2
(45) Date of Patent: Jun. 28, 2016

(54) REPROGRAMMING OF CELLS TO A NEW FATE

(75) Inventors: Jem A. Efe, San Diego, CA (US); Janghwan Kim, Daejeon (KR); Saiyong Zhu, San Diego, CA (US); Simon Hilcove, Vancouver (CA); Sheng Ding, Orinda, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/704,214

(22) PCT Filed: Jun. 14, 2011

(86) PCT No.: PCT/US2011/040390
§ 371 (c)(1),
(2), (4) Date: Jul. 2, 2013

(87) PCT Pub. No.: WO2011/159726
PCT Pub. Date: Dec. 22, 2011

(65) Prior Publication Data
US 2013/0280809 A1 Oct. 24, 2013

Related U.S. Application Data

(60) Provisional application No. 61/354,651, filed on Jun. 14, 2010, provisional application No. 61/376,148, filed on Aug. 23, 2010, provisional application No. 61/437,294, filed on Jan. 28, 2011.

(51) Int. Cl.
*C12N 15/85* (2006.01)
*C12N 5/071* (2010.01)
*C12N 5/077* (2010.01)
*C12N 5/079* (2010.01)
*C12N 5/0793* (2010.01)
*C12N 5/0797* (2010.01)

(52) U.S. Cl.
CPC ............ *C12N 5/0676* (2013.01); *C12N 5/0602* (2013.01); *C12N 5/0618* (2013.01); *C12N 5/0619* (2013.01); *C12N 5/0623* (2013.01); *C12N 5/0657* (2013.01); *C12N 5/0678* (2013.01); *C12N 15/85* (2013.01); *C12N 2501/01* (2013.01); *C12N 2501/155* (2013.01); *C12N 2501/602* (2013.01); *C12N 2501/603* (2013.01); *C12N 2501/604* (2013.01); *C12N 2501/606* (2013.01); *C12N 2501/727* (2013.01); *C12N 2506/1307* (2013.01); *C12N 2510/00* (2013.01)

(58) Field of Classification Search
CPC ............ C12N 15/85; C12N 2501/603; C12N 2501/604; C12N 2501/606; C12N 2501/01; C12N 2506/1307; C12N 2510/00; C12N 5/0602; C12N 2501/155; C12N 5/0623; C12N 5/0657; C12N 2501/602
See application file for complete search history.

(56) References Cited

U.S. PATENT DOCUMENTS

| | | |
|---|---|---|
| 5,824,837 A | 10/1998 | Chen et al. |
| 5,843,780 A | 12/1998 | Thomson |
| 6,200,806 B1 | 3/2001 | Thomson |
| 7,029,913 B2 | 4/2006 | Thomson |
| 7,265,138 B2 | 9/2007 | Doherty et al. |
| 8,298,825 B1 | 10/2012 | Hochedlinger et al. |
| 8,603,818 B1 | 12/2013 | Hochedlinger et al. |
| 8,906,677 B2 | 12/2014 | Li et al. |
| 2002/0142457 A1 | 10/2002 | Umezawa et al. |
| 2004/0157324 A1 | 8/2004 | Spradling et al. |
| 2006/0182724 A1 | 8/2006 | Riordan |
| 2007/0032447 A1 | 2/2007 | Eilertsen |
| 2007/0128719 A1 | 6/2007 | Tseng et al. |
| 2007/0134215 A1 | 6/2007 | Fukuda et al. |
| 2007/0141703 A1 | 6/2007 | Stanley et al. |
| 2007/0161107 A1* | 7/2007 | Mummery et al. ........... 435/366 |
| 2007/0172946 A1 | 7/2007 | Smith et al. |
| 2007/0196919 A1 | 8/2007 | Reh et al. |
| 2007/0254359 A1 | 11/2007 | Rezania et al. |
| 2007/0259423 A1 | 11/2007 | Odorico et al. |
| 2007/0264709 A1 | 11/2007 | Smith et al. |
| 2007/0269412 A1 | 11/2007 | Kopyov |
| 2007/0281355 A1 | 12/2007 | Dalton et al. |
| 2008/0066197 A1 | 3/2008 | Ying et al. |
| 2008/0242594 A1* | 10/2008 | McKay et al. ................ 514/3 |
| 2008/0268533 A1 | 10/2008 | Dalton et al. |
| 2009/0068742 A1 | 3/2009 | Yamanaka |

(Continued)

FOREIGN PATENT DOCUMENTS

| | | |
|---|---|---|
| CN | 101356270 | 1/2009 |
| EP | 1970446 A1 | 9/2008 |

(Continued)

OTHER PUBLICATIONS

Hakelien et al. 2004 "transient alteration of cell fate using a nuclear and cytoplasmic extract of an insulinoma cell line" BBRC 316:834-841.*
Chen et al., "Self-renewal of embryonic stem cells by a small molecule," PNAS, 103(46):17266-17271, 2006.
Watanabe et al., "A ROCK inhibitor permits survival of dissociated human embryonic stem cells," Nature Biotechnology, 25(6):681-868, 2007.
Artyomov et al., PLoS Comput Biol 6, e1000785 (2010).
Brambrink et al., Cell Stem Cell 2, 151-9 (2008).

(Continued)

*Primary Examiner* — Adam M Weidner
(74) *Attorney, Agent, or Firm* — Kilpatrick Townsend & Stockton LLP

(57) ABSTRACT

Methods and compositions for transdifferentiation of an animal cell from (i) a first pluripotent cell fate to a second nonpluripotent cell fate or (ii) from a non-pluripotent mesodermal, endodermal, or ectodermal cell fate to a different non-pluripotent mesodermal, endodermal, or ectodermal cell fate.

23 Claims, 45 Drawing Sheets

(56) References Cited

U.S. PATENT DOCUMENTS

| | | | |
|---|---|---|---|
| 2009/0117439 | A1 | 5/2009 | Fujinami et al. |
| 2009/0203690 | A1 | 8/2009 | Akritopoulou-Zanze et al. |
| 2009/0227032 | A1 | 9/2009 | Yamanaka et al. |
| 2010/0233804 | A1 | 9/2010 | Zhou et al. |
| 2010/0267141 | A1 | 10/2010 | Shi et al. |
| 2011/0033931 | A1 | 2/2011 | Schwartz et al. |
| 2011/0039332 | A1 | 2/2011 | Sakurada et al. |
| 2012/0122212 | A1 | 5/2012 | Grskovic et al. |
| 2012/0129172 | A1 | 5/2012 | Okano et al. |
| 2012/0196360 | A1 | 8/2012 | Okita et al. |
| 2013/0323833 | A1* | 12/2013 | Zhu et al. ............... 435/366 |
| 2015/0079675 | A1 | 3/2015 | Li et al. |

FOREIGN PATENT DOCUMENTS

| | | | |
|---|---|---|---|
| GB | 2 436 737 | | 10/2007 |
| GB | 2 450 603 | A | 12/2008 |
| JP | 2007/508026 | | 4/2007 |
| JP | 2008/307007 | | 12/2008 |
| JP | 2010/529851 | | 9/2010 |
| WO | 03/095628 | A2 | 11/2003 |
| WO | 2007/016566 | A2 | 2/2007 |
| WO | 2007/069666 | | 6/2007 |
| WO | 2007/113505 | | 10/2007 |
| WO | 2008/015418 | A2 | 2/2008 |
| WO | 2008/056173 | A2 | 5/2008 |
| WO | 2008/089351 | | 7/2008 |
| WO | WO2008088882 | * | 7/2008 ............ A61K 48/00 |
| WO | 2008/105630 | A1 | 9/2008 |
| WO | 2009/006422 | A1 | 1/2009 |
| WO | 2009/032194 | A1 | 3/2009 |
| WO | 2009/032456 | A1 | 3/2009 |
| WO | 2009/057831 | | 5/2009 |
| WO | 2009/067756 | A1 | 6/2009 |
| WO | 2009/067757 | A1 | 6/2009 |
| WO | 2009/073523 | A2 | 6/2009 |
| WO | 2009/117439 | A1 | 9/2009 |
| WO | 2011/047300 | A1 | 4/2011 |
| WO | 2011/109695 | A1 | 9/2011 |

OTHER PUBLICATIONS

Christen et al., BMC Biol 8, 5 (2010).
Ernst et al., "gp130-mediated Signal Transduction in Embryonic Stem Cells Involves Activation of Jak and Ras/Mitogen-activated Protein Kinase Pathways," J. Biol. Chem., Nov. 22, 1996, vol. 271, No. 47, pp. 30163-30143.
Graf et al., Nature 462(7273):587-594 (2009).
Han et al., Nat Cell Biol 13(1):66-71 (2011).
Hanna et al., Cell 133, 250-64, 2008.
Hanna et al., Nature 462, 595-601 (2009).
Hochedlinger et al., Development 136, 509-23 (2009).
Ieda et al., Cell 142, 375-86 (2010).
Jia et al., Nat Methods 7(3):197-199 (2010).
Kim et al., "Direct reprogramming of mouse fibroblasts to neural progenitors," Proc. Natl. Acad. Sci., USA, May 10, 2011, vol. 108, No. 9, pp. 7838-7843.
Kuzmenkin et al., FASEB J. 23, 4168-80 (2009).
Mikkelsen et al., Nature 454(7200):49-55 (2008).
Okada et al., Biochem Biophys Acta 1800, 956-63 (2010).
Okita et al., Nature 448, 313-317 (2007).
Schenke-Layland et al., Stem Cell 26, 1537-46 (2008).
Silva et al., Cell 138, 722-37 (2009).
Sridharan et al., Cell 136(2):364-377 (2009).
Stadtfeld et al., Cell Stem Cell 2, 230-40 (2008).
Stadtfeld et al., Nat Methods 7, 53-55 (2010).
Szabo et al., Nature 468(7323):521-526 (2010).
Takahashi et al., Nat Protoc 2, 3081-9 (2007).
Vierbuchen et al., "Direct conversion of fibroblasts to functional neurons by defined factors," Nature, Feb. 25, 2010, vol. 463, No. 7284, pp. 1035-1042.
Warren et al., Cell Stem Cell 7(5):618-630 (2010).
Wernig et al., Nat Biotechnol 26, 916-24 (2008).
Takahashi K, Cell 126, 663-676 (2006).
Zhou et al., Nature 455(7213):627-632 (2008).
PCT Application No. PCT/US2011/40390, International Search Report, mailed Jan. 26, 2012, 2 pages.
Aasen et al., Nat Biotechnol 26:1276-1284 (2008).
Beaujean et al., Dev. Biol., 2000, vol. 221, pp. 337-354.
Brons et al., Nature, 2007, vol. 448, pp. 191-195.
Chambers et al., Nature, 2007, vol. 450, pp. 1230-1234.
Chen et al., Proc Natl Acad Sci USA, 2007, vol. 104, pp. 10482-10487.
Chou et al., Cell, 2008, vol. 135, pp. 449-461.
Classen et al., "ROCK inhibition enhances the recovery and growth of cryopreserved human embryonic stem cells and human induced pluripotent stem cells," Molecular Reproduction and Developments, 2009, vol. 76, No. 8, pp. 722-732.
Collas et al., Reproductive BioMedicine Online: 762-770, 2006.
D'Amour et al., Nat Biotechnol, 2005, vol. 23, pp. 1534-1541.
Debs et al., J. Biol. Chem., 1990, vol. 265, pp. 10189-10192.
Demers et al., Cloning Stem Cells, 2007, vol. 9, pp. 512-522.
Dimos et al., Science, 2008, vol. 321, pp. 1218-1221.
Djuric et al., 202, Stem Cell Research and Therapy, 2010, 1:3.
Dvorak et al., Stem Cells, 2005, vol. 23, pp. 1200-1211.
Feng et al, "Molecules that Promote or Enhance Reprogramming of Somatic Cells to Induced Pluripotent Stem Cells," Cell Stem Cell, 2009, 4, 301-12.
Guo et al., Development, 2009, vol. 136, pp. 1063-1069.
Han et al., Curr Stem Cell Res Ther, 2008, vol. 3, pp. 66-74.
Hanna et al, "Treatment of Sickle Cell Anemia Mouse Model with iPS Cells Generated from Autologous Skin," Science, Dec. 21, 2007, vol. 318, pp. 1920-1922.
Hayashi et al., Cell Stem Cell, 2008, vol. 3, pp. 391-401.
Hindie et al., "Structure and allosteric effects of low-molecular-weight activators on the protein kinase PDK1," Nat Chem Biol, Oct. 2009, vol. 5, No. 10, pp. 758-764.
Ho et al., Cancer Res., 2001, vol. 61, pp. 474-477.
Hochedlinger, et al., "Nuclear reprogramming and pluripotency," Nature, Jun. 2006, vol. 441, pp. 1061-1067.
Huangfu et al., "Induction of pluripotent stem cells by defined factors is greatly improved by small-molecule compounds," Nat Biotechnol, Jul. 2008, vol. 26, No. 7, pp. 795-799.
Huangfu et al., "Induction of pluripotent stem cells from primary human fibroblasts with only Oct4 and Sox2," 2008, Nature Biotechnology, 26:11, pp. 1269-1275.
Hudecz et al., Medicinal Research Reviews, 25(6): 679-736, 2005.
Kanatsu-Shinohara et al., Cell, 2004, vol. 119, pp. 1001-1012.
Kim et al., Cell, 2009, vol. 136, pp. 411-419.
Kim et al., Cell Stem Cell, 4(6):472-476, 2009.
Krippl et al., Proc. Natl. Acad. Sci. USA, 1984, vol. 81, pp. 6988-6992.
Kubicek, et al., "Reversal of H3K9me2 by a Small-Molecule Inhibitor for the G9a Histone Methyltransferase," Molecular Cell, Feb. 2007, vol. 25, No. 3, pp. 473-481.
Li et al., "Generation of rat and human induced pluripotent stem cells by combining genetic reprogramming and chemical inhibitors," Cell Stem Cell, 2009, vol. 4, pp. 16-19.
Li et al., Differentiation, 2007, vol. 75, pp. 299-307.
Li et al., "Small molecules that modulate embryonic stem cell fate and somatic cell reprogramming," Trends Pharmacol Sci, Jan. 2010, vol. 31, No. 1, pp. 36-45.
Li et al., Stem Cells 27:2992-3000 (2009).
Lin et al., Nat Methods 6:805-808 (2009).
Lowry et al., Proc Natl Acad Sci USA, 2008, vol. 105, pp. 2883-2888.
Maherali et al., "Directly Reprogrammed Fibroblasts Show Global Epigenetic Remodeling and Widespread Tissue Contribution," Cell Stem Cell, 2007, 1, pp. 55-70.
Maherali et al., "Tgfβ Signal Inhibition Cooperates in the Induction of iPSCs and Replaces Sox2 and cMyc," Current Biology, 2009, vol. 19, pp. 1718-1723.
Meissner, et al., "Direct reprogramming of genetically unmodified fibroblasts into pluripotent stem cells," Nature Biotechnology, Oct. 2007, vol. 25, No. 10, pp. 1177-1181.
Mi et al., Mol. Ther., 2001, vol. 4, pp. 339-347.

(56) References Cited

OTHER PUBLICATIONS

Muller et al., "Upping the Ante: Recent Advances in Direct Reprogramming," Mol. Ther., 2009, vol. 17, pp. 947-953.
Nakagawa et al., Nat Biotechnol, 2008, vol. 26, pp. 101-106.
Okita et al., Science 322:949-953, 2008.
Oliveri et al., Regenerative Medicine, 2(5): 795-816, Sep. 2007.
Pan et al., J. Biol. Chem., 2004, vol. 279, pp. 37013-37020.
Peerani et al., EMBO J., 2007, vol. 26, pp. 4744-4755.
Plath et al., Nature Reviews, 12: 253-265, 2011.
Plews, et al., "Activation of Pluripotency Genes in Human Fibroblast Cells by a Novel mRNA Based Approach," PLoS One, Dec. 2010, vol. 5, No. 12, pp. 1-10.
Roberts et al., "PD98059 Enhanced Insulin, Cytokine, and Growth Factor Activation of Xanthine Oxidoreductase in Epithelial Cells Involves STAT3 and the Glucocoticoid Receptor," Journal of Cellular Biochemistry 2007, 101: 1567-1587.
Ruhnke et al., Stem Cells, 2003, vol. 21, pp. 428-436.
Saha et al., Biophys. J., 2008, vol. 94, pp. 4123-4133.
Sato et al., Dev. Biol., 2003, vol. 260, pp. 404-413.
Schugar et al., Gene Ther, 2008, vol. 15, pp. 126-135.
Schulze et al., Methods Mol Biol, 2006, vol. 329, pp. 45-58.
Sells et al., BioTechniques, 1995, vol. 19, pp. 72-78.
Shi, et al., "A Combined Chemical and Genetic Approach for the Generation of Induced Pluripotent Stem Cells," Cell Stem Cell, Jun. 2008, vol. 2, No. 6, pp. 525-528.
Shi "Induction of Pluripotent Stem Cells from Mouse Embryonic Fibroblasts by Oct4 and Klf4 with Small-Molecule Compounds," Cell Stem Cell, 2008, vol. 3, pp. 568-574.
Shields et al., J. Biol. Chem., 1997, vol. 272, pp. 18504-18507.
Silva et al., PLoS Biology, 6(10): 2237-2247 9 (e253), Oct. 2008.
Singh et al., Stem Cells, 2007, vol. 25, pp. 2534-2542.
Stacey et al., Mol. Cell. Biol., 1987, vol. 7, pp. 523-527.
Stadtfeld et al., Science 322:945-949, 2008.
Sullivan et al., Reproductive BioMed. Online, 16(1): 41-50, Nov. 2008.
Sylvester et al. (Arch Surg. 136:93-99, 2004).
Tada, et al., "Nuclear reprogramming of somatic cells by in vitro hybridization with ES cells," Current Biology, 2001, vol. 11, pp. 1553-1558.
Takahashi, et al., "Induction of Pluripotent Stem Cells from Mouse Embryonic and Adult Fibroblast Cultures by Defined Factors," Cell, Aug. 2006, vol. 126, No. 4, pp. 663-676.
Takahashi et al.; "Induction of Pluripotent Stem Cells from Adult Human Fobroblasts by Defined Factors"; Cell, 2007 131, pp. 861-872.
Taranger et al., "Induction of Dedifferentiation, Genomewide Transcriptional Programming, and Epigenetic Reprogramming by Extracts of Carcinoma and Embryonic Stem Cells," Molecular Biology of the Cell, 2005, vol. 16, pp. 5719-5735.
Tesar et al., Nature, 2007, vol. 448, pp. 196-199.
Tojo, et al., "The ALK-5 inhibitor A-83-01 inhibits Smad signaling and epithelia-to-mesenchymal transition by transforming growth factor-$\beta$," Cancer Sci, Nov. 2005, vol. 96, No. 11, pp. 791-800.
Toyooka et al., Development, 2008, vol. 135, pp. 909-918.
Ueda et al., PLoS ONE 3, 2008, e2800.
Wadia et al., Curr. Opin. Biotechnol., 2002, vol. 13, pp. 52-56.
Wering et al., "c-Myc is Dispensable for Direct Reprogramming of Mouse Fibroblasts," Cell Stem Cell, 2008, 2, 10-12.
Wernig, et al., "In vitro reprogramming of fibroblasts into a pluripotent ES-cell-like state," Nature, Jul. 2007, vol. 448, No. 7151, pp. 318-324.
Xu et al., Nature 453, 338-44 (2008).
Xu et al., Nat. Biotechnol, 2002, vol. 20, pp. 1261-1264.
Yamanaka, "Strategies and New Developments in the Generation of Patient-Specific Pluripotent Stem Cells," Cell Stem Cell, Jul. 2007, vol. 1, pp. 39-49.
Ying et al, Nature, 2008, vol. 453, pp. 519-523.
Ying et al., Cell, 2003, vol. 115, pp. 281-292.
Yu et al., Science, 2007, vol. 318, pp. 1917-1920.
Zhao et al., Cell Death and Differentiation, 2007, vol. 14, pp. 489-499.
Zheng et al., Cancer Res., 2003, vol. 63, pp. 6909-6913.
Zhou, Hongyan et al.; "Generation of Induced Pluripotent Stem Cells Using Recombinant Proteins"; Cell Stem Cell, 4: 381-384 (2009).
Zhu et al., "Reprogramming of human primary somatic cells by OCT4 and chemical compounds," Cell Stem Cell, Dec. 3, 2010, vol. 7, No. 6, pp. 651-655.
Feldman et al., "G9a-mediated irreversible epigenetic inactivation of Oct-3/4 during early embryogenesis," Nature Cell Biology, 2006, vol. 8(2), pp. 188-194.
Wu et al., "Cellular senescence is an important mechanism of tumor regression upon c-Myc inactivation," PNAS, 2007, vol. 104(32), pp. 13028-13033.
Tighe et al., BMC 8:34 doi//:www.biomedcentral.com/1471-2121/8/34, printout pp. 1-17.
Aoi et al., "Generation of Pluripotent Stem Cells from Adult Mouse Liver and Stomach Cells," Sciencexpress, Feb. 2008, DOI 10.1126/science.1154884, 8 pages.
Lin et al., Nat Methods 6:805-808 (2009), Supplemental Information, 7 pages.
Noggle et al., "A Molecular Basis for Human Embryonic Stem Cell Pluripotency," Stem Cell Reviews and Reports, Jan. 2005, vol. 1(2), pp. 1550-8943; DOI: 10.1385/scr:1:2:111.
Stadtfeld et al., "Reprogramming of Pancreatic $\beta$ Cells into Pluripotent Stem Cells," Curr. Biol., Jun. 2008, vol. 18(12): 890, doi: 10.1016/j.cub.2008.05.010.
Vallier et al., "Activin/Nodal and FGF pathways cooperate to maintain pluripotency of human embryonic stem cells," Journal of Cell Science, Oct. 2005, vol. 118(19), pp. 4495-4509, DOI: 10.1111/J.1432-0436.2006.00143.X.
Wenlin et al., "Generation of novel rat and human pluripotent stem cells by reprogramming and chemical approaches," Methods in Molecular Biology, Jan. 2010, vol. 636, pp. 293-300.
Xiong et al., "Histone deacetylase inhibitors DNA methyltransferase-3B messenger RNA stability and down-regulate de novo DNA methyltransferase activity in human endometrial cells," Cancer Res., Apr. 2005, vol. 65(7), pp. 2684-2689.
Zhou et al., "Conversion of Mouse Epiblast Stem Cells to an Earlier Pluripotency State by Small Molecules," Journal of Biological Chemistry, Sep. 2010, vol. 285(39), pp. 29676-29680; DOI: 10.1074/jbc.C110.150599.
Xu et al., "Revealing a core signaling regulatory mechanism for pluripotent stem cell survival and self-renewal by small molecules," PNAS, 2010, vol. 107(8), pp. 8129-8134.
Condorelli, G. et al., "Cardiomyocytes induce endothelial cells to trans-differentiate into cardiac muscle: Implications for myocardium regeneration," PNAS, vol. 98, No. 19, Sep. 11, 2001, pp. 10733-10738.
Dravida, S. et al., "The transdifferentiation potential of limbal fibroblast-like cells," Developmental Brain Research, vol. 160, No. 2, Dec. 7, 2005, pp. 239-251.
Efe, Jem E. et al., "Conversion of mouse fibroblasts into cardiomyocytes using a direct reprogramming strategy," Nature Cell Biology, vol. 13, No. 3, Mar. 1, 2011, pp. 215-222.
Kaji et al., "Virus free induction of pluripotency and subsequent excision of reprogramming factors," Nature, Apr. 2009, vol. 458(7239), pp. 771-775.
Kim et al., "Pluripotent stem cells induced from adult neural stem cells by reprogramming with two factors," 2008, Nature 454:646-651.
Loh et al., "Generation of induced pluripotent stem cells from human blood," Blood, May 2009, vol. 113(22), pp. 5476-5479.
Takei, Shunsuke et al., "Bone morphogenetic protein-4 promotes induction of cardiomyocytes from human embryonic stem cells in serum-based embryoid body development," AJP Heart and Circulatory Physiology, vol. 296, No. 6, Jun. 2009, pp. H1793-H1803.
Takeuchi, Jun K. et al., "Directed transdifferentiation of mouse mesoderm to heart tissue by defined factors," Nature, vol. 459, No. 7247, Jun. 4, 2009, pp. 708-711.
Egler et al., "Histone Deacetylase Inhibition and Blockade of the Glycolytic Pathway Synergistically Induce Glioblastoma Cell Death," Clin. Cancer Res., 2008, vol. 14(10), pp. 3132-3140.

(56) References Cited

OTHER PUBLICATIONS

Engel et al., "Allosteric activation of the protein kinase PDK1 with low molecular weight compounds," The EMBO Journal, 2006, vol. 25, pp. 5469-5480.

Gonzalez et al., "Generation of mouse-induced pluripotent stem cells by transient expression of a single nonviral polycistronic vector," PNAS, Jun. 2009, vol. 106(22), pp. 8918-8922.

Pesce et al., "Differential expression of the Oct-4 transcription factor during mouse germ cell differentiation," Mechanisms of Development, 1998, vol. 71, pp. 89-98.

Wang et al., "The Immunophilin FKBP12 Functions as a Common Inhibitor of the TGFβ Family Type 1 Receptors," Cell, Aug. 1996, vol. 86, pp. 435-444.

Watanabe et al., "Activation of Akt signaling is sufficient to maintain pluripotency in mouse and primate embryonic stem cells," Oncogene, 2006, vol. 25, pp. 2697-2707.

Zhao et al., "Resorcylic Acid Lactones: Naturally Occurring Potent and Selective Inhibitors of MEK," The Journal of Antibiotics, Dec. 1999, vol. 52(12), pp. 1086-1094.

* cited by examiner

A

B

A

B

C-peptide        Hoescht        Overlay

SEQUENCE LISTING

<160> NUMBER OF SEQ ID NOS: 31

<210> SEQ ID NO 1
<211> LENGTH: 61
<212> TYPE: PRT

<213> ORGANISM: Artificial Sequence
<220> FEATURE:
<223> OTHER INFORMATION: synthetic herpes simplex virus structural
      protein VP22 sequence that enhances transport across membranes

<400> SEQUENCE: 1

Gly Ser Pro Pro Thr Ala Pro Thr Arg Ser Lys Thr Pro Ala Gln Gly
1               5                   10                  15

Leu Ala Arg Lys Leu His Phe Ser Thr Ala Pro Pro Asn Pro Asp Ala
            20                  25                  30

Pro Trp Thr Pro Arg Val Ala Gly Phe Asn Lys Arg Val Phe Arg Phe
        35                  40                  45

Ser Pro Gln Thr Ala Arg Arg Ala Thr Thr Thr Arg Ile
    50                  55                  60

<210> SEQ ID NO 2
<211> LENGTH: 26
<212> TYPE: PRT
<213> ORGANISM: Artificial Sequence
<220> FEATURE:
<223> OTHER INFORMATION: synthetic Kaposi FGF signal sequence (kFGF)
      that enhances transport across membranes

<400> SEQUENCE: 2

Ala Gly Ser Gly Gly Ala Ala Val Ala Leu Leu Pro Ala Val Leu Leu
1               5                   10                  15

Ala Leu Leu Ala Pro Gly Gly Glu Phe Ala
            20                  25

<210> SEQ ID NO 3
<211> LENGTH: 21
<212> TYPE: PRT
<213> ORGANISM: Artificial Sequence
<220> FEATURE:
<223> OTHER INFORMATION: synthetic protein transduction domain-4 (PTD4)
      sequence that enhances transport across membranes

<400> SEQUENCE: 3

Ala Gly Ser Gly Gly Tyr Ala Arg Ala Ala Ala Arg Gln Ala Arg Ala
1               5                   10                  15

Gly Gly Glu Phe Ala
            20

<210> SEQ ID NO 4
<211> LENGTH: 16
<212> TYPE: PRT
<213> ORGANISM: Artificial Sequence
<220> FEATURE:
<223> OTHER INFORMATION: synthetic Penetratin peptide sequence that
      enhances transport across membranes

<400> SEQUENCE: 4

Arg Gln Ile Lys Ile Trp Phe Gln Gly Arg Arg Met Lys Trp Lys Lys
1               5                   10                  15

<210> SEQ ID NO 5
<211> LENGTH: 11
<212> TYPE: PRT
<213> ORGANISM: Artificial Sequence
<220> FEATURE:
<223> OTHER INFORMATION: synthetic HIV-1 transcriptional activator TAT
      protein sequence that enhances transport across membranes

<400> SEQUENCE: 5

Tyr Gly Arg Lys Lys Arg Arg Gln Arg Arg Arg

<210> SEQ ID NO 6
<211> LENGTH: 22
<212> TYPE: PRT
<213> ORGANISM: Artificial Sequence
<220> FEATURE:
<223> OTHER INFORMATION: synthetic M918 sequence that enhances transport
      across membranes

<400> SEQUENCE: 6

Met Val Thr Val Leu Phe Arg Arg Leu Arg Ile Arg Arg Ala Cys Gly
1               5                   10                  15

Pro Pro Arg Val Arg Val
            20

<210> SEQ ID NO 7
<211> LENGTH: 21
<212> TYPE: PRT
<213> ORGANISM: Artificial Sequence
<220> FEATURE:
<223> OTHER INFORMATION: synthetic Transportan-10 sequence that enhances
      transport across membranes

<400> SEQUENCE: 7

Ala Gly Tyr Leu Leu Gly Lys Ile Gly Leu Lys Ala Leu Ala Ala Leu
1               5                   10                  15

Ala Lys Lys Ile Leu
            20

<210> SEQ ID NO 8
<211> LENGTH: 20
<212> TYPE: PRT
<213> ORGANISM: Artificial Sequence
<220> FEATURE:
<223> OTHER INFORMATION: synthetic peptide comprising 11 contiguous
      arginines that enhances transport across membranes

<400> SEQUENCE: 8

Glu Ser Gly Gly Gly Gly Ser Pro Gly Arg Arg Arg Arg Arg Arg Arg
1               5                   10                  15

Arg Arg Arg Arg
            20

<210> SEQ ID NO 9
<211> LENGTH: 11
<212> TYPE: PRT
<213> ORGANISM: Artificial Sequence
<220> FEATURE:
<223> OTHER INFORMATION: synthetic L803 unmyristoylated GSK-3beta
      Inhibitor XIII
<220> FEATURE:
<221> NAME/KEY: MOD_RES
<222> LOCATION: (10)..(10)
<223> OTHER INFORMATION: phosphoserine
<220> FEATURE:
<221> NAME/KEY: MOD_RES
<222> LOCATION: (11)..(11)
<223> OTHER INFORMATION: AMIDATION at C-terminus, prolinamide

<400> SEQUENCE: 9

Lys Glu Ala Pro Pro Ala Pro Pro Gln Ser Pro
1               5                   10

<210> SEQ ID NO 10
<211> LENGTH: 24
<212> TYPE: DNA

<213> ORGANISM: Artificial Sequence
<220> FEATURE:
<223> OTHER INFORMATION: synthetic RT-PCR sense primer for Oct3/4 (Oct4, OCT4) Octamer family transcription factor

<400> SEQUENCE: 10
ggcgttctct ttggaaaggt gttc                                     24

<210> SEQ ID NO 11
<211> LENGTH: 20
<212> TYPE: DNA
<213> ORGANISM: Artificial Sequence
<220> FEATURE:
<223> OTHER INFORMATION: synthetic RT-PCR antisense primer for Oct3/4 (Oct4, OCT4) Octamer family transcription factor

<400> SEQUENCE: 11
ctcgaaccac atccttctct                                          20

<210> SEQ ID NO 12
<211> LENGTH: 20
<212> TYPE: DNA
<213> ORGANISM: Artificial Sequence
<220> FEATURE:
<223> OTHER INFORMATION: synthetic RT-PCR sense primer for early-stage cardiac marker Brachyury T (BryT)

<400> SEQUENCE: 12
catgtactct ttcttgctgg                                          20

<210> SEQ ID NO 13
<211> LENGTH: 20
<212> TYPE: DNA
<213> ORGANISM: Artificial Sequence
<220> FEATURE:
<223> OTHER INFORMATION: synthetic RT-PCR antisense primer for early-stage cardiac marker Brachyury T (BryT)

<400> SEQUENCE: 13
ggtctcggga aagcagtggc                                          20

<210> SEQ ID NO 14
<211> LENGTH: 24
<212> TYPE: DNA
<213> ORGANISM: Artificial Sequence
<220> FEATURE:
<223> OTHER INFORMATION: synthetic RT-PCR sense primer for mid-stage cardiac marker GATA4 (GATA-4, Gata-4) zinc-finger transcription factor

<400> SEQUENCE: 14
ttccttgtcc tcatcaccca caga                                     24

<210> SEQ ID NO 15
<211> LENGTH: 24
<212> TYPE: DNA
<213> ORGANISM: Artificial Sequence
<220> FEATURE:
<223> OTHER INFORMATION: synthetic RT-PCR antisense primer for mid-stage cardiac marker GATA4 (GATA-4, Gata-4) zinc-finger transcription factor

<400> SEQUENCE: 15
gacaatgtta acgggttgtg gagg                                     24

<210> SEQ ID NO 16
<211> LENGTH: 24

```
<212> TYPE: DNA
<213> ORGANISM: Artificial Sequence
<220> FEATURE:
<223> OTHER INFORMATION: synthetic RT-PCR sense primer for mid-stage
      cardiac marker Flk1 (Flk-1) receptor for vascular endothelial
      growth factor (VEGF)

<400> SEQUENCE: 16
ggttctctgt caagtggcgg taaa                                          24

<210> SEQ ID NO 17
<211> LENGTH: 24
<212> TYPE: DNA
<213> ORGANISM: Artificial Sequence
<220> FEATURE:
<223> OTHER INFORMATION: synthetic RT-PCR antisense primer for mid-stage
      cardiac marker Flk1 (Flk-1) receptor for vascular endothelial
      growth factor (VEGF)

<400> SEQUENCE: 17
agcacacagg cagaaaccag taga                                          24

<210> SEQ ID NO 18
<211> LENGTH: 21
<212> TYPE: DNA
<213> ORGANISM: Artificial Sequence
<220> FEATURE:
<223> OTHER INFORMATION: synthetic RT-PCR sense primer for mid-stage
      cardiac marker Isl1 (Isl-1, Islet-1)

<400> SEQUENCE: 18
tgtcaggaga cttgccactt t                                             21

<210> SEQ ID NO 19
<211> LENGTH: 29
<212> TYPE: DNA
<213> ORGANISM: Artificial Sequence
<220> FEATURE:
<223> OTHER INFORMATION: synthetic RT-PCR antisense primer for mid-stage
      cardiac marker Isl1 (Isl-1, Islet-1)

<400> SEQUENCE: 19
gccaaacgtt tattagtgaa atagtcctg                                     29

<210> SEQ ID NO 20
<211> LENGTH: 24
<212> TYPE: DNA
<213> ORGANISM: Artificial Sequence
<220> FEATURE:
<223> OTHER INFORMATION: synthetic RT-PCR sense primer for mid-stage
      cardiac marker Nkx2.5 cardiac specific transcription factor

<400> SEQUENCE: 20
acctttctcc gatccatccc actt                                          24

<210> SEQ ID NO 21
<211> LENGTH: 24
<212> TYPE: DNA
<213> ORGANISM: Artificial Sequence
<220> FEATURE:
<223> OTHER INFORMATION: synthetic RT-PCR antisense primer for mid-stage
      cardiac marker Nkx2.5 cardiac specific transcription factor

<400> SEQUENCE: 21
gcgttagcgc actcacttta atgg                                          24

<210> SEQ ID NO 22
```

```
<211> LENGTH: 24
<212> TYPE: DNA
<213> ORGANISM: Artificial Sequence
<220> FEATURE:
<223> OTHER INFORMATION: synthetic RT-PCR sense primer for late-stage
      cardiac marker Mlc2a (Mlc-2a) atrial isoform of myosin light chain

<400> SEQUENCE: 22
aagggaaggg tcccatcaac ttca                                              24

<210> SEQ ID NO 23
<211> LENGTH: 24
<212> TYPE: DNA
<213> ORGANISM: Artificial Sequence
<220> FEATURE:
<223> OTHER INFORMATION: synthetic RT-PCR antisense primer for
      late-stage cardiac marker Mlc2a (Mlc-2a) atrial isoform of myosin
      light chain

<400> SEQUENCE: 23
aacagttgct ctacctcagc agga                                              24

<210> SEQ ID NO 24
<211> LENGTH: 24
<212> TYPE: DNA
<213> ORGANISM: Artificial Sequence
<220> FEATURE:
<223> OTHER INFORMATION: synthetic RT-PCR sense primer for Mlc2v
      (MLC-2v, Myl7) cardiac specific ventricular structural gene

<400> SEQUENCE: 24
acttcaccgt gttcctcacg atgt                                              24

<210> SEQ ID NO 25
<211> LENGTH: 24
<212> TYPE: DNA
<213> ORGANISM: Artificial Sequence
<220> FEATURE:
<223> OTHER INFORMATION: synthetic RT-PCR antisense primer for Mlc2v
      (MLC-2v, Myl7) cardiac specific ventricular structural gene

<400> SEQUENCE: 25
tccgtgggta atgatgtgga ccaa                                              24

<210> SEQ ID NO 26
<211> LENGTH: 20
<212> TYPE: DNA
<213> ORGANISM: Artificial Sequence
<220> FEATURE:
<223> OTHER INFORMATION: synthetic RT-PCR sense primer for atrial
      natriuretic factor (ANF)

<400> SEQUENCE: 26
ttcctcgtct tggccttttg                                                   20

<210> SEQ ID NO 27
<211> LENGTH: 23
<212> TYPE: DNA
<213> ORGANISM: Artificial Sequence
<220> FEATURE:
<223> OTHER INFORMATION: synthetic RT-PCR antisense primer for atrial
      natriuretic factor (ANF)

<400> SEQUENCE: 27
cctcatcttc taccggcatc ttc                                               23

<210> SEQ ID NO 28
```

```
<211> LENGTH: 24
<212> TYPE: DNA
<213> ORGANISM: Artificial Sequence
<220> FEATURE:
<223> OTHER INFORMATION: synthetic RT-PCR sense primer for Nrg1

<400> SEQUENCE: 28
ccaatggcca cattgccaat aggt                                          24

<210> SEQ ID NO 29
<211> LENGTH: 24
<212> TYPE: DNA
<213> ORGANISM: Artificial Sequence
<220> FEATURE:
<223> OTHER INFORMATION: synthetic RT-PCR antisense primer for Nrg1

<400> SEQUENCE: 29
agcctggcct gtaattcttc ctgt                                          24

<210> SEQ ID NO 30
<211> LENGTH: 24
<212> TYPE: DNA
<213> ORGANISM: Artificial Sequence
<220> FEATURE:
<223> OTHER INFORMATION: synthetic RT-PCR sense primer for beta-actin

<400> SEQUENCE: 30
gaaggtgaca gcattgcttc tgtg                                          24

<210> SEQ ID NO 31
<211> LENGTH: 24
<212> TYPE: DNA
<213> ORGANISM: Artificial Sequence
<220> FEATURE:
<223> OTHER INFORMATION: synthetic RT-PCR antisense primer for
      beta-actin

<400> SEQUENCE: 31
ttggtctcaa gtcagtgtag aggc                                          24
```

US 9,376,664 B2

REPROGRAMMING OF CELLS TO A NEW FATE

CROSS-REFERENCES TO RELATED APPLICATIONS

This application is a U.S. National Phase under 35 USC 371 of PCT Application No. PCT/US2011/040390 filed Jun. 14, 2011, which claims priority to U.S. provisional application Nos. 61/354,651 filed Jun. 14, 2010; 61/376,148 filed Aug. 23, 2010; and 61/437,294 filed Jan. 28, 2011, the disclosures of which are incorporated by reference herein.

REFERENCE TO A SEQUENCE LISTING," A TABLE, OR A COMPUTER PROGRAM LISTING APPENDIX SUBMITTED AS AN ASCII TEXT FILE

The Sequence Listing written in file 077103-.860259-004210US_SequenceListing.txt, created on Mar. 16, 2016, 10,063 bytes, machine format IBM-PC, MS-Windows operating system, is hereby incorporated by reference in its entirety for all purposes.

BACKGROUND OF THE INVENTION

The mammalian heart lacks significant regenerative capacity. In vitro generation of cardiac cells in quantities sufficient for transplantation would therefore revolutionize the treatment of heart disease. A recent report of successful transdifferentiation of somatic cells to a cardiac fate in vitro (Ieda, M. et al., *Cell* 142, 375-86 (2010)) has raised the possibility that this process might eventually be used for cell-based cardiac therapy. However, speed and efficiency must first be improved, especially if the ultimate goal is to provide a faster and safer alternative to the re-differentiation of autologous induced pluripotent stem cells (iPSCs) (Schenke-Layland, K. et al., *Stem Cells* 26, 1537-46 (2008)).

BRIEF SUMMARY OF THE INVENTION

The present invention provides for methods of converting an animal cell from a first non-pluripotent cell fate to a second non-pluripotent cell fate. In some embodiments, the method comprises:
  increasing the quantity of at least one reprogramming transcription factor in an animal cell having the first cell fate to generate a cell that differentiates in response to lineage-specific differentiating factors to a second cell fate different from the first cell fate; and
  submitting the cell that differentiates in response to lineage-specific differentiating factors to conditions that induce differentiation of the cell to generate a cell having the second non-pluripotent cell fate.

In some embodiments, the development or growth of pluripotent cells is limited, e.g., by limiting the expression of, or contact of the cells to, the reprogramming transcription factor(s), or by contacting the cell that differentiates in response to lineage-specific differentiating factors with an inhibitor that inhibits the growth of pluripotent cells. In some embodiments, the inhibitor that inhibits the growth of pluripotent cells is a JAK inhibitor.

In some embodiments, the cell that differentiates in response to lineage-specific differentiating factors does not significantly express Nanog.

In some embodiments, the method occurs in the absence of exogenous LIF. In some embodiments, the cell that differentiates in response to lineage-specific differentiating factors is not capable of forming a teratoma.

In some embodiments, the method does not comprise isolation or selection of cells between the increasing and submitting steps.

In some embodiments, the cell that differentiates in response to lineage-specific differentiating factors is not an induced pluripotent stem cell.

In some embodiments, the animal cell having the first cell fate is a fibroblast or a neural precursor cell. In some embodiments, the cell having the second non-pluripotent cell fate is a cardiomyocyte.

In some embodiments, the submitting step comprises contacting the cell that differentiates in response to lineage-specific differentiating factors with BMP4, a calcium channel agonist (e.g., BayK 8644), a Gαs activating agent, a cAMP analog, and/or a GSK-3 inhibitor.

In some embodiments, the cell having the second non-pluripotent cell fate has a neural cell fate. In some embodiments, the cell having the second non-pluripotent cell fate has a pancreatic cell fate.

In some embodiments, the reprogramming factors are selected from the group consisting of an Oct polypeptide, a Klf polypeptide, a Sox2 polypeptide and a Myc polypeptide. In some embodiments, the reprogramming factors comprise an Oct polypeptide, a Klf polypeptide, and a Sox2 polypeptide. In some embodiments, the reprogramming factors comprise an Oct polypeptide, a Klf polypeptide, and a Myc polypeptide. In some embodiments, the reprogramming factors comprise a Myc polypeptide, a Klf polypeptide, and a Sox2 polypeptide. In some embodiments, the reprogramming factors comprise an Oct polypeptide, a Sox2 polypeptide, and a Myc polypeptide. In some embodiments, the reprogramming factors comprise an Oct polypeptide, a Klf polypeptide, a Sox2 polypeptide, and a Myc polypeptide. In some embodiments, the reprogramming factors comprise an Oct polypeptide and a Klf polypeptide. In some embodiments, the reprogramming factors comprise an Oct polypeptide and a Sox2 polypeptide. In some embodiments, the reprogramming factors comprise an Oct polypeptide and a Myc polypeptide. In some embodiments, the reprogramming factors comprise a Klf polypeptide and a Sox2 polypeptide. In some embodiments, the reprogramming factors comprise a Klf polypeptide and a Myc polypeptide. In some embodiments, the reprogramming factors comprise a Sox2 polypeptide and a Myc polypeptide.

In some embodiments, the time from initiation of the increasing step to the generation of the cell having the second non-pluripotent cell fate is no more than 25, 24, 23, 22, or 21 days. In some embodiments, the time from initiation of the increasing step to the generation of the cell having the second non-pluripotent cell fate is no more than 20, 19, 18, 17, or 16 days. In some embodiments, the time from initiation of the increasing step to the generation of the cell having the second non-pluripotent cell fate is no more than 15, 14, 13, 12, or 11 days. In some embodiments, the time from initiation of the increasing step to the generation of the cell having the second non-pluripotent cell fate is between 8-22 days (i.e., 8, 9, 10, 11, 12, 13, 14, 15, 16, 17, 18, 19, 20, 21, or 22 days), between 9-22 days (i.e., 9, 10, 11, 12, 13, 14, 15, 16, 17, 18, 19, 20, 21, or 22 days), between 10-22 days (i.e., 10, 11, 12, 13, 14, 15, 16, 17, 18, 19, 20, 21, or 22 days), between 10-25 days (i.e., 10, 11, 12, 13, 14, 15, 16, 17, 18, 19, 20, 21, 22, 23, 24, or 25 days), between 10-20 days (i.e., 10, 11, 12, 13, 14, 15, 16, 17, 18, 19, or 20 days), between 7-20 days (i.e., 7, 8, 9, 10, 11, 12, 13, 14, 15, 16, 17, 18, 19, or 20 days), between 7-22 days (i.e., 7, 8, 9, 10, 11, 12, 13, 14, 15, 16, 17, 18, 19, 20, 21, or 22 days), or between 7-25 days (i.e., 7, 8, 9, 10, 11, 12, 13, 14, 15, 16, 17, 18, 19, 20, 21, 22, 23, 24, or 25 days).

In some embodiments, the conditions that induce differentiation are chemically defined conditions.

In some embodiments, the method is conducted at least partly in vivo. In some embodiments, the increasing step is performed in vivo. In some embodiments, the submitting step occurs by inducing the increasing step in a cell in a cellular context in vivo such that endogenous signals cause the cell to have the second non-pluripotent cell fate.

In some embodiments, the method is conducted in vitro.

In another aspect, the present invention provides for methods of differentiating an animal cell into a cardiomyocyte. In some embodiments, the method comprises contacting the animal cell with a GSK-3 inhibitor and/or a BMP protein (e.g., BMP4) under conditions to generate a cardiomyocyte.

In some embodiments, the animal cell is a non-human animal cell. In some embodiments, the animal cell is a human cell.

In some embodiments, the cell is a pluripotent cell. In some embodiments, the cell is not a pluripotent cell.

In some embodiments, the method is conducted at least partly in vivo. In some embodiments, the method is conducted in vitro.

In some embodiments, the conditions are chemically defined conditions.

In another aspect, the present invention provides for methods of transdifferentiating an animal cell into a cardiomyocyte. In some embodiments, the method comprises:
    introducing into a non-pluripotent animal cell having a first non-pluripotent cell fate one or more polynucleotides encoding one or more polypeptides selected from the group consisting of an Oct polypeptide, a Klf polypeptide, a Sox2 polypeptide and a Myc polypeptide; or contacting a non-pluripotent animal cell having a first non-pluripotent cell fate with one or more polypeptides selected from the group consisting of an Oct polypeptide, a Klf polypeptide, a Sox2 polypeptide and a Myc polypeptide; and
    contacting the cell with a GSK-3 inhibitor, a calcium channel agonist (e.g., BayK 8644), a Gαs activating agent, a cAMP analog, and/or a BMP protein (e.g., BMP4) under conditions to generate the cardiomyocyte; thereby differentiating the cell into the cardiomyocyte.

In some embodiments, the method further comprises contacting the non-pluripotent animal cell with a JAK inhibitor. In some embodiments, the non-pluripotent animal cell is contacted with the JAK inhibitor prior to contacting the cell with the GSK-3 inhibitor, the calcium channel agonist (e.g., BayK 8644), the Gαs activating agent, the cAMP analog, and/or the BMP protein (e.g., BMP4). In some embodiments, contacting the non-pluripotent animal cell with the JAK inhibitor comprises culturing the non-pluripotent animal cell in the presence of the JAK inhibitor. In some embodiments, the non-pluripotent animal cell is cultured in the presence of the JAK inhibitor for a period of about one to about nine days (e.g., about 1, 2, 3, 4, 5, 6, 7, 8, or 9 days).

In yet another aspect, the present invention provides for methods of transdifferentiating an animal cell into a neural progenitor cell. In some embodiments, the method comprises:
    introducing into a non-pluripotent animal cell having a first non-pluripotent cell fate one or more polynucleotides encoding one or more polypeptides selected from the group consisting of an Oct polypeptide, a Klf polypeptide, a Sox2 polypeptide and a Myc polypeptide; or contacting a non-pluripotent animal cell having a first non-pluripotent cell fate with one or more polypeptides selected from the group consisting of an Oct polypeptide, a Klf polypeptide, a Sox2 polypeptide and a Myc polypeptide; and
    contacting the cell with FGF2, FGF4, and EGF under conditions to generate the neural progenitor cell; thereby differentiating the cell into the neural progenitor cell.

In some embodiments, the method further comprises contacting the non-pluripotent animal cell with a Wnt inhibitor, a JAK inhibitor, or both a Wnt inhibitor and a JAK inhibitor. In some embodiments, the non-pluripotent animal cell is contacted with the Wnt inhibitor, the JAK inhibitor, or both the Wnt inhibitor and the JAK inhibitor prior to contacting the cell with FGF2, FGF4, and EGF.

In still another aspect, the present invention provides for methods of transdifferentiating an animal cell into a retinal pigmented epithelium cell. In some embodiments, the method comprises:
    introducing into a non-pluripotent animal cell having a first non-pluripotent cell fate one or more polynucleotides encoding one or more polypeptides selected from the group consisting of an Oct polypeptide, a Klf polypeptide, a Sox2 polypeptide and a Myc polypeptide; or contacting a non-pluripotent animal cell having a first non-pluripotent cell fate with one or more polypeptides selected from the group consisting of an Oct polypeptide, a Klf polypeptide, a Sox2 polypeptide and a Myc polypeptide;
    contacting the cell with FGF2, FGF4, and EGF under conditions to generate a neural progenitor cell; and
    contacting the neural progenitor cell with a TGFβ inhibitor and a GSK-3 inhibitor to generate the retinal pigmented epithelium cell; thereby differentiating the cell into the retinal pigmented epithelium cell.

In yet another aspect, the present invention provides for methods of transdifferentiating an animal cell into a tyrosine hydroxylase (TH)-positive neuronal cell. In some embodiments, the method comprises:
    introducing into a non-pluripotent animal cell having a first non-pluripotent cell fate one or more polynucleotides encoding one or more polypeptides selected from the group consisting of an Oct polypeptide, a Klf polypeptide, a Sox2 polypeptide and a Myc polypeptide; or contacting a non-pluripotent animal cell having a first non-pluripotent cell fate with one or more polypeptides selected from the group consisting of an Oct polypeptide, a Klf polypeptide, a Sox2 polypeptide and a Myc polypeptide; and
    contacting the cell with FGF8 and SHH under conditions to generate the TH-positive neuronal cell; thereby differentiating the cell into the TH-positive neuronal cell.

In still another aspect, the present invention provides for methods of transdifferentiating an animal cell into a pancreatic lineage cell. In some embodiments, the method comprises:
    (1) introducing into a non-pluripotent animal cell having a first non-pluripotent cell fate one or more polynucleotides encoding one or more polypeptides selected from the group consisting of an Oct polypeptide, a Klf polypeptide, a Sox2 polypeptide and a Myc polypeptide; or contacting a non-pluripotent animal cell having a first non-pluripotent cell fate with one or more polypeptides selected from the group consisting of an Oct polypeptide, a Klf polypeptide, a Sox2 polypeptide and a Myc polypeptide; and (2) under conditions to generate the pancreatic lineage cell,
  (a) contacting the cell with a TGFβ/Activin/Nodal family member and a JAK inhibitor;
  (b) contacting the cell of step (2)(a) with a TGFβ/ALK5 receptor inhibitor, BMP4, bFGF, and RA; and
  (c) contacting the cell of step (2)(b) with nicotinamide;
thereby differentiating the cell into the pancreatic lineage cell.

In still another aspect, the present invention provides for methods of transdifferentiating an animal cell into an induced definitive endoderm (iDE) cell. In some embodiments, the method comprises:
  introducing into a non-pluripotent animal cell having a first non-pluripotent cell fate one or more polynucleotides encoding one or more polypeptides selected from the group consisting of an Oct polypeptide, a Klf polypeptide, a Sox2 polypeptide and a Myc polypeptide; or contacting a non-pluripotent animal cell having a first non-pluripotent cell fate with one or more polypeptides selected from the group consisting of an Oct polypeptide, a Klf polypeptide, a Sox2 polypeptide and a Myc polypeptide; and
  contacting the cell with a GSK-3 inhibitor, an HDAC inhibitor, and a TGFβ/Activin/Nodal family member under conditions to generate the iDE cell; thereby differentiating the cell into the iDE cell.

In yet another aspect, the present invention provides for methods of transdifferentiating an animal cell into a pancreatic beta cell. In some embodiments, the method comprises:
  (1) introducing into a non-pluripotent animal cell having a first non-pluripotent cell fate one or more polynucleotides encoding one or more polypeptides selected from the group consisting of an Oct polypeptide, a Klf polypeptide, a Sox2 polypeptide and a Myc polypeptide; or contacting a non-pluripotent animal cell having a first non-pluripotent cell fate with one or more polypeptides selected from the group consisting of an Oct polypeptide, a Klf polypeptide, a Sox2 polypeptide and a Myc polypeptide;
  (2) contacting the cell with a GSK-3 inhibitor, an HDAC inhibitor, and a TGFβ/Activin/Nodal family member under conditions to generate an iDE cell; and
  (3) under conditions to generate the pancreatic beta cell,
    (a) contacting the iDE cell with FGF7, RA, a Hedgehog pathway inhibitor, a BMP inhibitor, and a TGFβ/ALK5 receptor inhibitor;
    (b) contacting the cell of step (3)(a) with EGF and a Notch inhibitor; and
    (c) contacting the cell of step (3)(b) with bFGF and nicotinamide;
  thereby differentiating the cell into the pancreatic beta cell.
In some embodiments, step (3) of the method further comprises contacting with extendin 4. In some embodiments, step (3)(c) further comprises contacting the cell of step (3)(b) with extendin 4.

DEFINITIONS

"Cell fate" as used herein is used as generally understood in the field of cell biology and refers to the ultimate differentiated state to which a cell has become committed.

An "Oct polypeptide" refers to any of the naturally-occurring members of Octamer family of transcription factors, or variants thereof that maintain transcription factor activity, similar (within at least 50%, at least 60%, at least 70%, at least 80%, or at least 90% activity) as compared to the closest related naturally occurring family member, or polypeptides comprising at least the DNA-binding domain of the naturally occurring family member, and can further comprise a transcriptional activation domain. Exemplary Oct polypeptides include, Oct-1, Oct-2, Oct-3/4, Oct-6, Oct-7, Oct-8, Oct-9, and Oct-11. e.g., Oct3/4 (referred to herein as "Oct4") which contains the POU domain, a 150 amino acid sequence conserved among Pit-1, Oct-1, Oct-2, and uric-86. See, Ryan, A. K. & Rosenfeld, M. G. *Genes Dev.* 11, 1207-1225 (1997). In some embodiments, variants have at least 85%, 86%, 87%, 88%, 89%, 90%, 91%, 92%, 93%, 94%, 95% or greater amino acid sequence identity across their whole sequence compared to a naturally occurring Oct polypeptide family member such as those listed above or such as listed in Genbank accession number NP_002692.2 (human Oct4) or NP_038661.1 (mouse Oct4). Oct polypeptides (e.g., Oct3/4) can be from human, mouse, rat, bovine, porcine, or other animals. Generally, the same species of protein will be used with the species of cells being manipulated.

A "Klf polypeptide" refers to any of the naturally-occurring members of the family of Krüppel-like factors (Klfs), zinc-finger proteins that contain amino acid sequences similar to those of the *Drosophila* embryonic pattern regulator Krüppel, or variants of the naturally-occurring members that maintain transcription factor activity similar (within at least 50%, at least 60%, at least 70%, at least 80%, or at least 90% activity) as compared to the closest related naturally occurring family member, or polypeptides comprising at least the DNA-binding domain of the naturally occurring family member, and can further comprise a transcriptional activation domain. See, Dang, D. T., Pevsner, J. & Yang, V. W. *Cell Biol.* 32, 1103-1121 (2000). Exemplary Klf family members include, Klf1, Klf2, Klf3, Klf-4, Klf5, Klf6, Klf7, Klf8, Klf9, Klf10, Klf11, Klf12, Klf13, Klf14, Klf15, Klf16, and Klf17. Klf2 and Klf-4 were found to be factors capable of generating iPS cells in mice, and related genes Klf1 and Klf5 did as well, although with reduced efficiency. See, Nakagawa, et al., *Nature Biotechnology* 26:101-106 (2007). In some embodiments, variants have at least 85%, 86%, 87%, 88%, 89%, 90%, 91%, 92%, 93%, 94%, 95% or greater amino acid sequence identity across their whole sequence compared to a naturally occurring Klf polypeptide family member such as those listed above or such as listed in Genbank accession number CAX16088 (mouse Klf4) or CAX14962 (human Klf4). Klf polypeptides (e.g., Klf1, Klf4, and Klf5) can be from human, mouse, rat, bovine, porcine, or other animals. Generally, the same species of protein will be used with the species of cells being manipulated. To the extent a Klf polypeptide is described herein, it can be replaced with an estrogen-related receptor beta (Essrb) polypeptide. Thus, it is intended that for each Klf polypeptide embodiment described herein, a corresponding embodiment using Essrb in the place of a Klf4 polypeptide is equally described.

A "Myc polypeptide" refers any of the naturally-occurring members of the Myc family (see, e.g., Adhikary, S. & Eilers, M. *Nat. Rev. Mol. Cell Biol.* 6:635-645 (2005)), or variants thereof that maintain transcription factor activity similar (within at least 50%, at least 60%, at least 70%, at least 80%, or at least 90% activity) as compared to the closest related naturally occurring family member, or polypeptides comprising at least the DNA-binding domain of the naturally occurring family member, and can further comprise a transcriptional activation domain. Exemplary Myc polypeptides include, e.g., c-Myc, N-Myc and L-Myc. In some embodiments, variants have at least 85%, 86%, 87%, 88%, 89%, 90%, 91%, 92%, 93%, 94%, 95% or greater amino acid sequence identity across their whole sequence compared to a naturally occurring Myc polypeptide family member, such as those listed above or such as listed in Genbank accession number CAA25015 (human Myc). Myc polypeptides (e.g., c-Myc) can be from human, mouse, rat, bovine, porcine, or other animals. Generally, the same species of protein will be used with the species of cells being manipulated.

A "Sox polypeptide" refers to any of the naturally-occurring members of the SRY-related HMG-box (Sox) transcription factors, characterized by the presence of the high-mobility group (HMG) domain, or variants thereof that maintain transcription factor activity similar (within at least 50%, at least 60%, at least 70%, at least 80%, or at least 90% activity) as compared to the closest related naturally occurring family member, or polypeptides comprising at least the DNA-binding domain of the naturally occurring family member, and can further comprise a transcriptional activation domain. See, e.g., Dang, D. T., et al., *Int. J. Biochem. Cell Biol.* 32:1103-1121 (2000). Exemplary Sox polypeptides include, e.g., Sox1, Sox-2, Sox3, Sox4, Sox5, Sox6, Sox7, Sox8, Sox9, Sox10, Sox11, Sox12, Sox13, Sox14, Sox15, Sox17, Sox18, Sox-21, and Sox30. Sox1 has been shown to yield iPS cells with a similar efficiency as Sox2, and genes Sox3, Sox15, and Sox18 have also been shown to generate iPS cells, although with somewhat less efficiency than Sox2. See, Nakagawa, et al., *Nature Biotechnology* 26:101-106 (2007). In some embodiments, variants have at least 85%, 86%, 87%, 88%, 89%, 90%, 91%, 92%, 93%, 94%, 95% or greater amino acid sequence identity across their whole sequence compared to a naturally occurring Sox polypeptide family member such as those listed above or such as listed in Genbank accession number CAA83435 (human Sox2). Sox polypeptides (e.g., Sox1, Sox2, Sox3, Sox15, or Sox18) can be from human, mouse, rat, bovine, porcine, or other animals. Generally, the same species of protein will be used with the species of cells being manipulated.

A "recombinant" polynucleotide is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

"Expression cassette" refers to a polynucleotide comprising a promoter or other regulatory sequence operably linked to a sequence encoding a protein.

The terms "promoter" and "expression control sequence" are used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Promoters include constitutive and inducible promoters. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "heterologous sequence" or a "heterologous nucleic acid", as used herein, is one that originates from a source foreign to the particular host cell, or, if from the same source, is modified from its original form. Thus, a heterologous expression cassette in a cell is an expression cassette that is not endogenous to the particular host cell, for example by being linked to nucleotide sequences from an expression vector rather than chromosomal DNA, being linked to a heterologous promoter, being linked to a reporter gene, etc.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, *Proteins* (1984)).

"Inhibitors," "activators," and "modulators" of expression or of activity are used to refer to inhibitory, activating, or modulating molecules, respectively, identified using in vitro and in vivo assays for expression or activity of a described target protein, e.g., ligands, agonists, antagonists, and their homologs and mimetics. The term "modulator" includes inhibitors and activators. Inhibitors are agents that, e.g., inhibit expression or bind to, partially or totally block stimulation or protease inhibitor activity, decrease, prevent, delay activation, inactivate, desensitize, or down regulate the activity of the described target protein, e.g., antagonists. Activators are agents that, e.g., induce or activate the expression of a described target protein or bind to, stimulate, increase, open, activate, facilitate, enhance activation or protease inhibitor activity, sensitize or up regulate the activity of described target protein (or encoding polynucleotide), e.g., agonists. Modulators include naturally occurring and synthetic ligands, antagonists and agonists (e.g., small chemical molecules, antibodies and the like that function as either agonists or antagonists). Such assays for inhibitors and activators include, e.g., applying putative modulator compounds to cells expressing the described target protein and then determining the functional effects on the described target protein activity, as described above. Samples or assays comprising described target protein that are treated with a potential activator, inhibitor, or modulator are compared to control samples without the inhibitor, activator, or modulator to examine the extent of effect. Control samples (untreated with modulators) are assigned a relative activity value of 100%. Inhibition of a described target protein is achieved when the activity value relative to the control is about 80%, optionally 50% or 25, 10%, 5% or 1%. Activation of the described target protein is achieved when the activity value relative to the control is 110%, optionally 150%, optionally 200, 300%, 400%, 500%, or 1000-3000% or more higher.

DETAILED DESCRIPTION

I. Introduction

Figure 1:
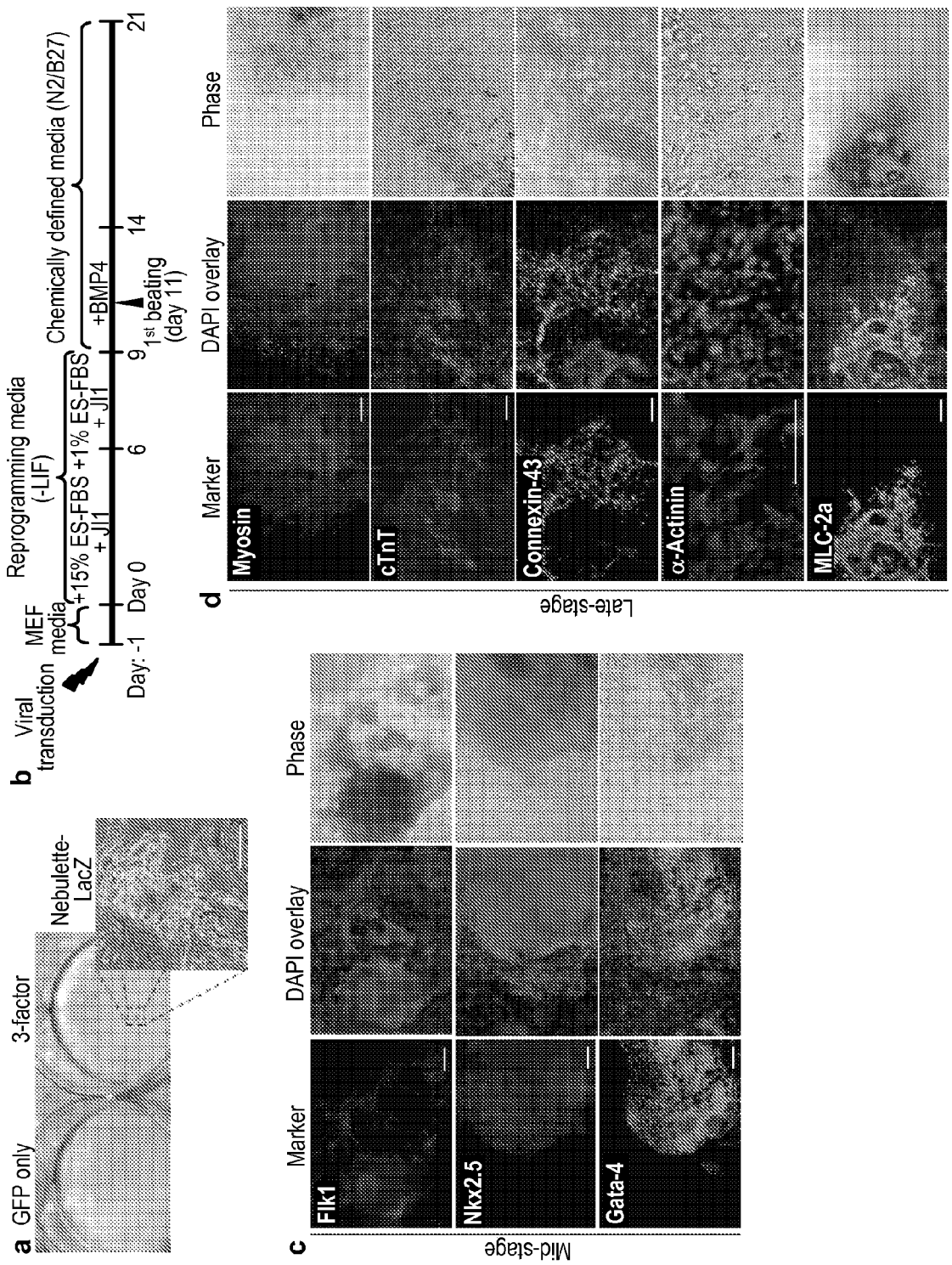
FIG. 1: Development of robust conditions for direct reprogramming of fibroblasts to a mature cardiac fate. (A) X-gal staining of Nebulette-LacZ$^+$ colonies arising seven days after three-factor transduction. (B) An outline of the final direct cardiac reprogramming conditions, with the onset of spontaneous contraction indicated. (C, D) Immunostaining of mid- and late-stage cardiac lineage markers on days 11-15 and 18-21, respectively. Scale bars in (A), (C), and (D) are 100 µm.

Methods and compositions for efficiently transdifferentiating a cell from a first cell fate to a second fate are provided. For example, a cell first differentiates into a first cell fate. During the transdifferentiation, the cell is changed from a first cell fate into a different cell fate. In some embodiments, the cell transdifferentiates from one cell type (e.g., cells of ectoderm, mesoderm, or endoderm) to a different cell type. In some embodiments, an ectoderm cell transdifferentiates into an endoderm cell. In some embodiments, an ectoderm cell transdifferentiates into a mesoderm cell. In some embodiments, an endoderm cell transdifferentiates into an ectoderm cell. In some embodiments, an endoderm cell transdifferentiates into a mesoderm cell. In some embodiments, a mesoderm cell transdifferentiates into an endoderm cell. In some embodiments, a mesoderm cell transdifferentiates into an ectoderm cell. In some embodiments, the method of transdifferentiation comprises at least two steps:

(1) submitting an animal cell having a first cell fate to conditions to generate a cell (i.e., a less differentiated cell) that is capable of differentiating into a second cell fate; and (2) submitting the less differentiated cell to conditions to differentiate the cell into a cell having the second cell fate.

For example, the inventors have discovered that it is possible to treat a differentiated cell (i.e., mouse embryonic fibroblasts (MEFs) or neural precursor cells) in culture to generate a less differentiated cell that can be subsequently differentiated into any of cardiac cells (e.g., cardiomyoctes), neuronal cells (e.g., when MEFs are initially used), or pancreatic cells. Thus, it is believed that the method is generally applicable for transdifferentiating one cell type to another without generating a pluripotent intermediate, or at least without generation of an induced pluripotent (iPS) cell. For example, the inventors have found that the transdifferentiation method does not require the inclusion of LIF, which is typically required for maintenance of iPS cells. Moreover, the transitory less differentiated cells generated express little or no Nanog and thus can be distinguished from iPS cells by substantial lack of expression of Nanog. To the extent Nanog or Oct4 expression was observed in beating colonies when conditions to generate cardio cells were used, only very large colonies sometimes contained both a beating patch and some very weak Nanog or Oct4 expression, but these areas never overlapped. Finally, the timing of generation of the new cells (e.g., the cardiomyocytes) measured from the start of reprogramming is considerably faster than would be expected if the cells were generated via an induced pluripotent stem cell intermediate.

II. Generation of Undifferentiated Cells from Cells Having a First Committed Cell Fate The inventors have found that applying partial, but not complete, iPS reprogramming conditions to differentiated cells can result in cells that are capable of differentiating into a second cell fate, i.e., to a different cell lineage than the first cell fate. As explained below, the inventors have found that induction of retrovirally-delivered three (Oct4, Klf4, Sox2) or four (Oct4, Klf4, Sox2, c-Myc) "Yamanaka factors" in serum but the absence of LIF (i.e., a factor generally necessary for significant iPS cell production) was sufficient to generate cells that could subsequently and directly be induced to other lineages. While the specific conditions used by the inventors can be used, it is believed that other iPS reprogramming conditions can also be modified such that substantially no iPS cells are generated and yet cells capable of altered differentiation are produced. To date, a large number of different methods and protocols have been established for inducing non-pluripotent mammalian cells into iPS cells. iPS cells are similar to ESCs in morphology, proliferation, and pluripotency, judged by teratoma formation and chimaera contribution. Reprogramming protocols that can be modified as described herein are believed to include those involving introduction of one or more reprogramming transcription factors selected from an Oct polypeptide (including but not limited to Oct 3/4), a Sox polypeptide (including but not limited to Sox2), a Klf polypeptide (including but not limited to Klf4) and/or a Myc polypeptide (including but not limited to c-Myc). The reprogramming factors can be introduced into the cells, for example, by expression from a recombinant expression cassette that has been introduced into the target cell, or by incubating the cells in the presence of exogenous reprogramming transcription factor polypeptides such that the polypeptides enter the cell.

Studies have shown that retroviral transduction of mouse fibroblasts with four transcription factors that are highly expressed in ESCs (Oct-3/4, Sox2, KLF4 and c-Myc) generate induced pluripotent stem (iPS) cells in combination with LIF. See, Takahashi, K. & Yamanaka, S. *Cell* 126, 663-676 (2006); Okita, K., Ichisaka, T. & Yamanaka, S, *Nature* 448, 313-317 (2007); Wernig, M. et al. *Nature* 448, 318-324 (2007); Maherali, N. et al. *Cell Stem Cell* 1, 55-70 (2007); Meissner, A., Wernig, M. & Jaenisch, R. *Nature Biotechnol.* 25, 1177-1181 (2007); Takahashi, K. et al. *Cell* 131, 861-872 (2007); Yu, J. et al. *Science* 318, 1917-1920 (2007); Nakagawa, M. et al. *Nature Biotechnol.* 26, 101-106 (2007); Wernig, M., Meissner, A., Cassady, J. P. & Jaenisch, R. *Cell Stem Cell.* 2, 10-12 (2008). Such methods can be altered to lack LIF, or otherwise not generate iPS cells (including but not limited to the specific methods for blocking iPS cell generation described herein), and yet be capable of re-differentiation of cells to a second cell fate. As an alternative to omitting LIF, or in combination, to reduce the possible contamination of pluripotent cells, some chemical compounds that inhibit the growth of pluripotent cells can be included in the cell culture media or otherwise contacted to the target cells. Exemplary chemical compounds include, but are not limited to, PI3K inhibitors, CDK2 inhibitors, Wnt inhibitors, or a combination thereof.

In embodiments involving expression in the cell or contact to the cell of one or more reprogramming transcription factors, the methods can involve limiting expression or exposure of the cells to the reprogramming transcription factors. For example, in some embodiments, expression of the factors is induced (e.g., by an inducible promoter) for a limited time that is insufficient to produce iPS cells. For example, in some embodiments, the transcription factor(s) are induced for between 1-9, 2-8, 3-6 days. Expression can subsequently be turned off by changing the media or condition of the cells to remove the inducer. Similarly, in embodiments in which the cells are exposed to protein transcription factors (discussed more below), the cells are contacted to the protein for a limited time, thereby reducing or preventing development of iPS cells.

This invention employs routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)). In some embodiments, expression cassettes for expression of one or more reprogramming transcription factor is introduced into a cell.

In some embodiments, the species of cell and protein to be expressed is the same. For example, if a mouse cell is used, a mouse ortholog or active protein variant thereof is introduced into the cell. If a human cell is used, a human ortholog protein or active variant thereof is introduced into the cell. Alternatively, in some embodiments, the species of cell and protein are not matched.

It will be appreciated that where two or more proteins are to be expressed in a cell (e.g., two or more polypeptides selected from the group consisting of an Oct polypeptide, a Klf polypeptide, a Sox2 polypeptide, and a Myc polypeptide), one or multiple expression cassettes can be used. For example, where one expression cassette expresses multiple polypeptides, a polycistronic expression cassette can be used.

Any type of vector can be used to introduce an expression cassette of the invention into a cell. Exemplary vectors include but are not limited to plasmids and viral vectors. Exemplary viral vectors include, e.g., adenoviral vectors, AAV vectors, and retroviral (e.g., lentiviral) vectors.

Suitable methods for nucleic acid delivery for transformation of a cell, a tissue or an organism for use with the current invention are believed to include virtually any method by which a nucleic acid (e.g., DNA) can be introduced into a cell, a tissue or an organism, as described herein or as would be known to one of ordinary skill in the art (e.g., Stadtfeld and Hochedlinger, *Nature Methods* 6(5):329-330 (2009); Yusa et al., *Nat. Methods* 6:363-369 (2009); Woltjen et al., *Nature* 458, 766-770 (9 Apr. 2009)). Such methods include, but are not limited to, direct delivery of DNA such as by ex vivo transfection (Wilson et al., *Science,* 244:1344-1346, 1989, Nabel and Baltimore, *Nature* 326:711-713, 1987), optionally with Fugene6 (Roche) or Lipofectamine (Invitrogen), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, *J. Cell Biol.,* 101: 1094-1099, 1985; U.S. Pat. No. 5,789,215, incorporated herein by reference); by electroporation (U.S. Pat. No. 5,384,253, incorporated herein by reference; Tur-Kaspa et al., *Mol. Cell Biol.,* 6:716-718, 1986; Potter et al., *Proc. Nat'l Acad. Sci. USA,* 81:7161-7165, 1984); by calcium phosphate precipitation (Graham and Van Der Eb, *Virology,* 52:456-467, 1973; Chen and Okayama, *Mol. Cell Biol.,* 7(8):2745-2752, 1987; Rippe et al., *Mol. Cell Biol.,* 10:689-695, 1990); by using DEAE-dextran followed by polyethylene glycol (Gopal, *Mol. Cell Biol.,* 5:1188-1190, 1985); by direct sonic loading (Fechheimer et al., *Proc. Nat'l Acad. Sci. USA,* 84:8463-8467, 1987); by liposome mediated transfection (Nicolau and Sene, *Biochim. Biophys. Acta,* 721:185-190, 1982; Fraley et al., *Proc. Nat'l Acad. Sci. USA,* 76:3348-3352, 1979; Nicolau et al., *Methods Enzymol.,* 149:157-176, 1987; Wong et al., *Gene,* 10:87-94, 1980; Kaneda et al., *Science,* 243:375-378, 1989; Kato et al., *J Biol. Chem.,* 266: 3361-3364, 1991) and receptor-mediated transfection (Wu and Wu, *Biochemistry,* 27:887-892, 1988; Wu and Wu, *J. Biol. Chem.,* 262:4429-4432, 1987); and any combination of such methods, each of which is incorporated herein by reference.

To address the safety issues that arise from target cell genomes harboring integrated exogenous sequences, a number of modified genetic protocols have been further developed and can be modified according to the present invention. These protocols produce iPS cells with potentially reduced risks, and include non-integrating adenoviruses to deliver reprogramming genes (Stadtfeld, M., et al. (2008) *Science* 322, 945-949), transient transfection of reprogramming plasmids (Okita, K., et al. (2008) *Science* 322, 949-953), piggyBac transposition systems (Woltjen, K., et al. (2009). *Nature* 458, 766-770, Yusa et al. (2009) *Nat. Methods* 6:363-369, Kaji, K., et al. (2009) *Nature* 458, 771-775), Cre-excisable viruses (Soldner, F., et al. (2009) *Cell* 136, 964-977), and oriP/EBNA1-based episomal expression system (Yu, J., et al. (2009) *Science DOI:* 10.1126). Such methods can be modified for example as described herein.

In some embodiments, reprogramming can involve culturing target cells in the presence of one or more proteins under conditions to allow for introduction of the proteins into the cell. See, e.g., Zhou H et al., *Cell Stem Cell.* 2009 May 8; 4(5):381-4; WO/2009/117439. One can introduce an exogenous polypeptide (i.e., a protein provided from outside the cell and/or that is not produced by the cell) into the cell by a number of different methods that do not involve introduction of a polynucleotide encoding the polypeptide. In some embodiments, the exogenous proteins comprise the transcription factor polypeptide of interest linked (e.g., linked as a fusion protein or otherwise covalently or non-covalently linked) to a polypeptide that enhances the ability of the transcription factor to enter the cell (and in some embodiments the cell nucleus).

Examples of polypeptide sequences that enhance transport across membranes include, but are not limited to, the *Drosophila* homeoprotein antennapedia transcription protein (AntHD) (Joliot et al., *New Biol.* 3: 1121-34, 1991; Joliot et al., *Proc. Natl. Acad. Sci. USA,* 88: 1864-8, 1991; Le Roux et al., *Proc. Natl. Acad. Sci. USA,* 90: 9120-4, 1993), the herpes simplex virus structural protein VP22 (Elliott and O'Hare, *Cell* 88: 223-33, 1997); the HIV-1 transcriptional activator TAT protein (Green and Loewenstein, *Cell* 55: 1179-1188, 1988; Frankel and Pabo, *Cell* 55: 1 289-1193, 1988); Kaposi FGF signal sequence (kFGF); protein transduction domain-4 (PTD4); Penetratin, M918, Transportan-10; a nuclear localization sequence, a PEP-I peptide; an amphipathic peptide (e.g., an MPG peptide); delivery enhancing transporters such as described in U.S. Pat. No. 6,730,293 (including but not limited to an peptide sequence comprising at least 5-25 or more contiguous arginines or 5-25 or more arginines in a contiguous set of 30, 40, or 50 amino acids; including but not limited to an peptide having sufficient, e.g., at least 5, guanidino or amidino moieties); and commercially available Penetratin™ 1 peptide, and the Diatos Peptide Vectors ("DPVs") of the Vectocell® platform available from Daitos S.A. of Paris, France. See also, WO/2005/084158 and WO/2007/123667 and additional transporters described therein. Not only can these proteins pass through the plasma membrane but the attachment of other proteins, such as the transcription factors described herein, is sufficient to stimulate the cellular uptake of these complexes. A number of polypeptides capable of mediating introduction of associated molecules into a cell have been described previously and can be adapted to the present invention. See, e.g., Langel (2002) Cell Penetrating Peptides CRC Press, Pharmacology and Toxicology Series.

Exemplary polypeptide sequences that enhance transport across membranes include:

```
VP22:                               (SEQ ID NO.: 1)
G S P P T A P T R S K T P A Q G L A R K L H F S

T A P P N P D A P W T P R V A G F N K R V F R F

S P Q T A R R A T T T R I;

kFGF:                               (SEQ ID NO.: 2)
A G S G G A A V A L L P A V L L A L L A P G G E

F A;

PTD4:                               (SEQ ID NO.: 3)
A G S G G Y A R A A A R Q A R A G G E F A;

PENETRATIN:                         (SEQ ID NO.: 4)
R Q I K I W F Q G R R M K W K K;

TAT:                                (SEQ ID NO.: 5)
Y G R K K R R Q R R R;

M918:                               (SEQ ID NO.: 6)
M V T V L F R R L R I R R A C G P P R V R V;

TRANSPORTAN-10:                     (SEQ ID NO.: 7)
A G Y L L G K I G L K A L A A L A K K I L.
```

In some embodiments, the polypeptide that enhances transport across membranes is a peptide sequence comprising at least 5 or more contiguous or non-contiguous arginines (e.g., a 8-arginine peptide). In some embodiments, the polypeptide that enhances transport across membranes is a peptide sequence comprising at least 7 or more contiguous or non-contiguous arginines. For example, the polypeptide that enhances transport across membranes is a peptide sequence comprising 11 contiguous arginines, e.g., ESGGGGSPGR-RRRRRRRRRR (SEQ ID NO:8). As noted above, the arginines in the transport enhancing sequence need not all be contiguous. In some embodiments, the polyarginine (e.g., the contiguous or non-contiguous) region is at least 5, 8, 10, 12, 15, 20, or more amino acids long and has at least, e.g., 40%, 50%, 60%, 70%, 80%, 90%, or more arginines.

An exogenous polypeptide can be introduced into cells by traditional methods such as lipofection, electroporation, calcium phosphate precipitation, particle bombardment and/or microinjection, or can be introduced into cells by a protein delivery agent. For example, the exogenous polypeptide can be introduced into cells by covalently or noncovalently attached lipids, e.g., by a covalently attached myristoyl group. Lipids used for lipofection are optionally excluded from cellular delivery modules in some embodiments. In some embodiments, the transcription factor polypeptides described herein are exogenously introduced as part of a liposome, or lipid cocktail (such as commercially available Fugene®6 and Lipofectamine™). In another alternative, the transcription factor proteins can be microinjected or otherwise directly introduced into the target cell. In some embodiments, the transcription factor polypeptides are delivered into cells using Profect protein delivery reagents, e.g., Profect-P1 and Profect-P2 (Targeting Systems, El Cajon, Calif.), or using Pro-Ject® transfection reagents (Pierce, Rockford Ill., USA). In some embodiments, the transcription factor polypeptides are delivered into cells using a single-wall nano tube (SWNT).

As discussed in the Examples of WO/2009/117439, incubation of cells with the transcription factor polypeptides of the invention for extended periods can be toxic to the cells. Therefore, in some embodiments of the invention, the non-pluripotent mammalian cells are intermittently incubated with one or more of an Oct polypeptide (including but not limited to Oct 3/4), a Sox polypeptide (including but not limited to Sox2), a Klf polypeptide (including but not limited to Klf4) and/or a Myc polypeptide (including but not limited to c-Myc) with intervening periods of incubation of the cells in the absence of the one or more polypeptides. In some embodiments, the cycle of incubation with and without the polypeptides can be repeated for 2, 3, 4, 5, 6, or more times but is not performed for sufficient lengths of time (i.e., the incubations with and without proteins) to achieve the development of pluripotent cells.

A variety of agents (e.g., HDAC inhibitor, TGFβ receptor/ALK5 inhibitor, MEK/ERK pathway inhibitor, and/or Rho GTPase/ROCK inhibitor, etc.) can be contacted to non-pluripotent cells either prior to, simultaneously with, or after delivery of, programming transcription factors (for example, delivered via expression cassette or as proteins). Exemplary small molecules that can be used are described in, e.g., WO/2009/117439. For convenience, the day the reprogramming factors are delivered is designated "day 1". In some embodiments, the inhibitors are contacted to cells in aggregate (i.e., as a "cocktail") at about days 3-7 and continued for 7-14 days. Alternatively, in some embodiments, the cocktail is contacted to the cells at day 0 (i.e., a day before the pre-programming factors) and incubated for about 14-30 days.

The cell into which a protein of interest is introduced can be a mammalian cell. The cells can be human or non-human (e.g., primate, rat, mouse, rabbit, bovine, dog, cat, pig, etc.). The cell can be, e.g., in culture or in a tissue, fluid, etc. and/or from or in an organism.

Optionally, or in addition, small molecules can "complement" or replace what is generally otherwise understood as a necessary expression of one of these proteins to result in pluripotent cells. By contacting a cell with an agent that functionally replaces one of the transcription factor, it is possible to generate pluripotent cells with all of the above-listed transcription factors except for the transcription factor replaced or complemented by the agent.

III. Limiting the Development or Growth of Pluripotent Cells

Provided herein are methods of transdifferentiating an animal cell from a first non-pluripotent cell fate to a second non-pluripotent cell fate, e.g., by increasing the quantity of at least one reprogramming transcription factor in an animal cell having the first cell fate to generate a cell that differentiates in response to lineage-specific differentiating factors. It was discovered that the methods provided herein do not require the generation of an intermediate, pluripotent cell. In fact, it has been now discovered that limiting the development or growth of pluripotent cells generally improves transdifferentiation efficiency, e.g., from a first non-pluripotent cell fate to a second non-pluripotent cell fate. Thus, in some embodiments, the methods of the present invention comprise limiting the development or growth of pluripotent cells.

The development or growth of pluripotent cells can be limited in several ways. For example, the standard reprogramming protocol can be modified, e.g., by modifying reprogramming media. As described above, reprogramming media can be modified by omitting components that are generally necessary for significant pluripotent cell production, e.g., LIF. In some embodiments, reprogramming media can be modified by omitting feeder MEFs. Alternatively, reprogramming media can be modified by including components that are harmful or detrimental for pluripotent cell production, e.g., FBS.

The development or growth of pluripotent cells can be limited by limited expression of transcription factors. As detailed in the examples herein, limited expression of transcription factors can be achieved by placing reprogramming transcription factors under the control of an inducible promoter (e.g., a doxycycline-inducible promoter). For example, transcription factors can be silenced in the absence of doxycycline. Limited expression of transcription factors can be achieved by transient transfection of reprogramming plasmids or other non-integrating reprogramming plasmids (see, e.g., Okita, K., et al. (2008) *Science* 322, 949-953). Similarly, expression of exogenous transcription factors can be eliminated, i.e., the cells are not transfected with a reprogramming plasmid at all. For example, the transcription factors can be introduced by, e.g., culturing target cells in the presence of one or more proteins under conditions to allow for introduction of the proteins into the cell.

The development or growth of pluripotent cells can be limited by certain inhibitors that inhibit the growth of pluripotent cells. For example, certain inhibitors can be used to selectively inhibit the growth of pluripotent cells, but not the growth of somatic cells. Exemplary selective inhibitors include, but are not limited to, JAK inhibitors, PI3K inhibitors, CDK2 inhibitors, CDK4 inhibitors, and glycolysis inhibitors. These inhibitors can be used individually or in combination, to inhibit the growth of pluripotent cells.

JAK Inhibitors

Inhibitors of Janus Kinase (JAK) suitable for use in the present invention are well known in the art, see for example, U.S. Pat. No. 6,452,005. In addition, bis monocyclic, bicyclic or heterocyclic aryl compounds (PCT Publication No. WO 92/20642), vinylene-azaindole derivatives (PCT Publication No. WO 94/14808) and 1-cyclopropyl-4-pyridyl-quinolones (U.S. Pat. No. 5,330,992) have been described the use of these agents as tyrosine kinase inhibitors. Styryl compounds (U.S. Pat. No. 5,217,999), styryl-substituted pyridyl compounds (U.S. Pat. No. 5,302,606), certain quinazoline derivatives (published EP Application No. 0 566 266 A1), seleoindoles and selenides (PCT Publication No. WO 94/03427), tricyclic polyhydroxylic compounds (PCT Publication No. WO 92/21660) have also been disclosed to be tyrosine kinase inhibitors. An exemplary JAK inhibitor is 2-(1,1-Dimethylethyl)-9-fluoro-3,6-dihydro-7H-benz[h]-imidaz[4,5-f]isoquinolin-7-one ("Ji1").

PI3K Inhibitors

Phosphoinositide 3-kinases (PI 3-kinases or PI3Ks) are a family of related intracellular single transducer enzymes capable of phosphorylating the 3 position hydroxyl group of the inositol ring of phosphatidylinositol (PtdIns or PI). These enzymes are also known as phosphatidylinositol-3-kinases. Based on based on primary structure, regulation, and in vitro lipid substrate specificity, the phosphoinositol-3-kinase family can be divided into three different classes: Class I, Class II and Class III (see Leevers et al., (1999) *Current Op. Cell Biol.* 11:219).

As used herein, the term "PI3K inhibitor" refers to a compound that inhibits at least one activity of a PI3K of Class I, II or III on at least one of its substrates (e.g., phosphorylating phosphatidylinositol to produce phosphatidylinositol 3-phosphate (PI(3)P), phosphatidylinositor (3,4)-bisphosphate (PI (3,4)P.sub.2), or phosphatidylinositol (3,4,5)-trisphosphate (PI(3,4,5)P.sub.3). A person skilled in the art can readily determine whether a compound, such as wortmannin or LY294002, is a PI3K inhibitor. A specific method of identifying such compounds or ligand is disclosed in, for example, U.S. Pat. Nos. 5,858,753; 5,882,910; and 5,985,589, Jackson et al. (2005) *Nat. Med.* 11:507, Pomel et al. (2006) *J. Med. Chem.* 49:3857; Palanki et al. (2007) *J. Med. Chem.* 50:4279), which methods are incorporated by reference herein.

In certain embodiments, a PI3K inhibitor inhibits the activity of a Class I PI3K. For example, a PI3K inhibitor may inhibit p110α, p110β, or p110γ, or p110Δ. In some embodiments, a PI3K inhibitor blocks or reduces the activity of p110γ, or p110Δ as compared to untreated p110γ, or p110Δ. In certain embodiments, a PI3K inhibitor inhibits the activity of a Class II PI3K. For example, a PI3K inhibitor may inhibit PI3K-C2α, PI3K-C2β, or PI3K-C2γ. In certain embodiments, a PI3K inhibitor inhibits the activity of a Class III PI3K, Vps34.

In certain embodiments, a PI3K inhibitor is selective or specific for a particular PI3K isoform. An inhibitor is "selective" or "specific" for a particular PI3K isoform if it inhibits that particular PI3K isoform more effectively than other PI3K isoforms. For example, an inhibitor specific for a particular PI3K isoform may have an $IC_{50}$ for the particular PI3K isoform at most about $\frac{1}{10}$ (e.g., at most about $\frac{1}{20}$, $\frac{1}{30}$, $\frac{1}{40}$, $\frac{1}{50}$, $\frac{1}{60}$, $\frac{1}{80}$, $\frac{1}{100}$, $\frac{1}{200}$, $\frac{1}{300}$, $\frac{1}{400}$, $\frac{1}{500}$, $\frac{1}{600}$, $\frac{1}{800}$, or $\frac{1}{1000}$) of the $IC_{50}$ for other PI3K isoforms. For example, a p110Δ-specific inhibitor may have an $IC_{50}$ value for p110Δ at most about $\frac{1}{10}$ of the $IC_{50}$ for other PI3K isoforms (e.g., p110α, p110β, or p110γ).

In some embodiments, a PI3K inhibitor is specific for p110α, p110β, or p110γ, or p110Δ. In certain embodiments, a PI3K inhibitor inhibits two or more classes or subclasses of PI3Ks. In certain embodiments, a PI3K inhibitor is also an mTOR inhibitor.

Exemplary PI3K inhibitors include LY294002 (2-morpholin-4-yl-8-phenylchromen-4-one) and wortmannin. Both LY294002 and wortmannin are broad inhibitors against PI3K and can also inhibit mTOR. PI3K inhibitors also include wortmannin derivatives, such as PX-866 (see, Ihie et al., *Mol Cancer Ther* 3:763-72, 2004).

Exemplary p110γ-specific inhibitors include furan-2-ylmethylene thiazolidinediones (AS-252424) (see, Pomel et al., 2006, supra) and 3,3'-(2,4-diaminopteridine-6,7-diyl)diphenol (see, Palanki et al., supra). Exemplary p110Δ-specific inhibitors include IC486068 and IC87114 (ICOS Corp., now Eli Lilly and Company) and CAL-101 and CAL-263 (Calistoga Pharmaceuticals). Another PI3K inhibitor with p110Δ and p110β inhibition is CAL-120, a PI3K inhibitor (Calistoga Pharmaceuticals). Another exemplary PI3K inhibitor is GDC-0941 bismesylate (2-(1H-indazol-4-yl)-6-(4-methanesulfonyl-piperazin-1-ylmethyl)-4-morphol-in-4-yl-thieno[3, 2-d]pyrimidine, bimesylate salt), a p110α and P110Δ selective inhibitor.

Additional PI3K inhibitors include pyrazole derivatives disclosed in PCT Publication No. WO 2009/059030, amino triazole derivatives disclosed in WO 2009/068482, an imidazothiadiazole compound disclosed in WO 2009/040552, fused pyrimidin-4-one compounds specific for p110Δ disclosed in WO 2009/064802, morpholino-pyrimidine compounds that inhibit p110α disclosed in WO 2009/066084, a 4-pyrimidin-4-yl-morpholine derivative disclosed in WO 2009/042607, a 4-morpholin-4-yl-thienopyrimidine compound disclosed in WO 2009/036082, a pyridosulphonamide derivative disclosed in WO 2009/055418, pyridopyrimidine derivatives that inhibit p110α and/or p110γ disclosed in WO 2009039140, heterocyclic derivatives that inhibit p110α disclosed in WO 2009046448, furanopyrimidines and zolopyrimidines specific for p110Δ disclosed in WO 2008/152394 and WO 2008/152390, quinazoline compounds specific for p110Δ disclosed in WO 2008/152387, pyrimidine-substituted purine derivatives disclosed in WO 2009/045175, thienopyrimidine and pyrazolopyrimidine compounds disclosed in WO 2009/052145, imidazolopyrimidine, pyrrolopyrimidine and pyrazolopyrimidine analogues disclosed in WO 2009/070524, substituted imidazopyridazine disclosed in WO 2008/138834, thienopyrimidiene derivatives selective for the p110Δ disclosed in WO 2009/053715, purine derivatives selective for the p110Δ disclosed in WO 2009/053716, 2-(morpholin-4-yl)-substituted purine derivatives disclosed in WO 2009/045174, PI3KΔ (p110Δ) inhibitors disclosed in U.S. Pat. Nos. 6,518,277 and 6,800,620 and U.S. Application Publication No. 2005/0261317, and BGT226, XL765 and BEZ235 (Novartis).

CDK2 Inhibitors

Illustrative cyclin-dependent kinase II (CDK2) inhibitors that may be employed in the broad practice of the invention include the cyclin-dependent kinase II inhibitor compounds described in the following references, the disclosures of all of which are hereby incorporated herein by reference in their respective entireties: (A) substituted oxindole derivatives described in International Patent Application No. PCT/EP98/05559 filed Sep. 3, 1998 for "Substituted Oxindole Derivatives," (B) purine derivatives described in International Publication WO97/20842; (C) pyridylpyrimidinamine derivatives described in International Publication WO95/09852; (D) 2,6,9-trisubstituted compounds described in International Publication WO98/05335 of CV Therapeutics; (E) 4H-1-benzopyran-4-one derivatives described in German Patent 3836676; (F) 2-thiol and 2-oxo-flavopiridol analogues described in U.S. Pat. No. 5,705,350, and in U.S. Pat. No. 5,849,733; (G) pyrido[2,3-D]pyrimidines and 4-aminopyrimidines described in International Publication WO98/33798 as well as in U.S. Pat. Nos. 5,776,942; 5,733,913; 5,223,503; 4,628,089; 4,536,575; 4,431,805; and 4,252,946; (H) antiviral CDK2 inhibitor compounds described in International Publication WO98/39007; (I) chimeric CDK2 inhibitors described in International Publication WO97/27297 of Mitotix Inc.; (J) the 2,6,9-trisubstituted purines described in Imbach, P., et al., 2,6,9-Trisubstituted Purines: Optimization Towards Highly Potent and Selective CDK1 Inhibitors, *Bioorganic and Medicinal Chemistry Letters*, 9 (1999), 91-96; (K) the peptide inhibitors described in U.S. Pat. No. 5,625,031 issued Apr. 29, 1997; (L) CDK2 inhibitor antisense sequences described in U.S. Pat. No. 5,821,234 issued Oct. 13, 1998; (M) the C2 alkynylated purines described in Legraverend, M., et al., Synthesis of C2 Alkynylated Purines, a New Family of Potent Inhibitors of Cyclin-Dependent Kinases, *Bioorganic & Medicinal Chemistry Letters* 8 (1998) 793-798; and (N) the tyrphostins described in Kleinberger-Doron, N., et al., Inhibition of Cdk2 Activation by Selected Tyrphostins Causes Cell Cycle Arrest at Late G1 and S Phase, Experimental Cell Research 241, 340-351 (1998).

CDK4 Inhibitors

CDK4 (cyclin dependent kinase 4) inhibitors can, in the broadest sense, be any compound that is capable of inhibiting the activity of CDK4. As such, general CDK inhibitors that can inhibit the activity of two or more different CDKs, e.g., CDK1, CDK2, as well as CDK4, can be used. Alternatively, CDK4 selective inhibitors can be used. It is now understood that CDK4 and CDK6 are closely related kinases with virtually indistinguishable biochemical properties. The amino acid and nucleic acid sequence coding for human CDK4 and CDK6 can be found at Genbank accession numbers $NM_{13}13$ 000075 and $NM_{13}$ 13 001259, respectively. The Genbank accession number U37022 also refers to CDK4. As used herein, CDK4 inhibitor refers to a compound that can be demonstrated to inhibit the activity of CDK4 or of CDK6. A given inhibitor is considered to be selective for CDK4 if its determined inhibitory activity for CDK4 is at least 5-fold, at least 10-fold, or at least 25-fold more potent than its determined inhibitory activity for CDK that is other than CDK4 and CDK6, e.g., CDK1, CDK2, etc.

A number of assays are known in the art for determining CDK4 inhibitory activity of a compound, where representative such assays are described in U.S. Pat. Nos., 6,040,321; 6,569,878; etc., where representative in vitro assays that find use evaluate, in a time dependent manner, a given compound's ability to inhibit the ability of CDK4 to incorporate radiolabeled phosphate donor into a protein substrate.

Representative specific CDK4 inhibitors include, but are not limited to, the following:

(i) naturally occurring indolocarbazole arcyriaflavin A as well as substituted indolocarbazoles (see, e.g., Zhu et al., *J Med. Chem.* 2003, 46, 2027-2030). Other derivatives of interest include those described in U.S. Patent Application Publication Nos. 2003/0229026 and 2004/0048915 (or equivalently, WO 01/44247 and WO 02/28861, respectively) which disclose indolo[6,7-a]pyrrolo[3,4-c]carbazole-6,8-diones as potent CDK4 inhibitors.

(ii) semi-synthetic flavopiridol (also known as alvocidib) disclosed in U.S. Pat. No. 4,900,727; as well as analogs of flavopiridol, such as those reported in U.S. Pat. Nos. 5,733,920 and 5,849,733.

(iii) diarylurea derivatives disclosed in EP 1199306 A1, and structurally related 2(1H)-pyrazinone fused aromatic or heterocyclic derivatives having CDK4 and CDK6 activity described in US 2003/0203907 (or equivalently, EP 1295878 A1).

(iv) diaminothiazoles, e.g., as reported in US 2002/0151554 (now U.S. Pat. No. 6,756,374 B2), where a specific example of such compounds is the compound denoted by the research code Ro-0506220.

(v) napthyridinones disclosed in U.S. Pat. No. 6,150,359, the pyrido[2,3-d]pyrimidines disclosed in U.S. Pat. No. 6,498,163 B1, and the 2-(pyridin-2-ylamino)pyrido[2,3-d]pyrimidin-7-ones disclosed in patent publication US 2003/0149001. In particular, US 2003/0149001 discloses 6-acetyl-8-cyclopentyl-5-methyl-2-[5-(1-piperazinyl)pyridin-2-ylamino]pyr-ido[2,3-d]pyrimidin-7 (8H)-one (7a) denoted by the research code PD-332991.

(vi) the pyrimidine derivatives disclosed in WO 00/12485 and U.S. Pat. No. 6,593,326 B1, the imidazo[1,2-a]pyridine and pyrazolo[2,3-a]pyridine derivatives disclosed in WO 01/14375, the 4-amino-5-cyano-2-anilo-pyrimidine derivatives disclosed in the publication US 2003/0087923 A1, the aminothiazole compounds disclosed in U.S. Pat. Nos. 6,040,321, 6,262,096 B1, and 6,569,878 B1; the acridone and benzothiadiazine derivatives disclosed in U.S. Pat. No. 6,630,464 B1 (or equivalently WO 98/49146); and the oxindole derivatives disclosed in U.S. Pat. No. 6,720,332 B2 (or equivalently WO 02/20524). Yet further examples of CDK4 inhibitors are described in Toogood, *Curr. Opin. Cell. Biol.* 2002, 6, 472-478, Toogood, *Med. Res. Rev.*, 2001, 21, 487-498, and in Carini et al., *Bioorgan. Med. Chem. Lett.*, 2001, 11, 2209-2211.

Glycolysis Inhibitors

Enzymes associated with glycolysis pathway are known in the art and include hexokinase, glucokinase (in tumors or in rapidly proliferating tissues), phosphoglucose isomerase, phosphofructokinase, aldolase, triose phosphate isomerase, glyceraldehydes 3-phosphate dehydrogenase, phosphoglycerate kinase, phosphoglyceromutase, enolase, pyruvate kinase and, indirectly, lactate dehydrogenase (lactate metabolism). It is an aspect of the invention that an inhibitor of anaerobic ATP synthesis is an inhibitor of an enzyme associated with the glycolytic pathway. Inhibitors of the glycolytic pathway are any known in the art.

Inhibitors of hexokinase may be configurational isomers of monosaccharides modified at C-6 by substitution (replacement) or removal of 6-OH (the hydroxyl group). An example of a substituent is a blocking moiety—for example, an atom from the halogen family, such as fluorine (6-fluoro-D-glucose). Another example of a substituent is a thiol group. Monosaccharides modified at C-6 by removal of 6-OH will not be transformed by hexokinase or glucokinase (see below) to glucose-6-phosphate and can potentially block both enzymes.

Inhibitors of hexokinase are any known in the art and may include, but are not limited to any of the following:
  (i) 6-fluoro-D-glucose, 6-bromo-D-glucose, 6-chloro-D-glucose, 6-O-methyl-D-glucose, 6-Thio-D-glucose, 6-deoxy-D-glucose, and any derivative known in the art.
  (ii) C-6 substituted derivatives of other hexose ring pyranoses (mannopyranoses, galactopyranoses). Examples include 6-deoxy-6-fluoro-D-mannose, and any known in the art.
  (iii) Various halogenated (fluoro, bromo, chloro-) C6 sugars derivatives such as gluconolactones, glucuronic acid, glucopyranoside, and their phosphate derivatives, and any known in the art. Halogenated glucosides may also be delivered indirectly to the cell, by compounds such as glucoronides with halogenated glycosides at the C-1 position (once in the cell, glucoronidases will cleave it, and deliver active hexose in the cell). Preferably, an inhibitor of hexokinase is 6-deoxy-6-fluoro-D-glucose and its derivatives.

Inhibitors of glucokinase may be any in the art. They include, but are not limited to mannoheptulose, mannoheptose, glucoheptose, N-acetylglucosamine. Glucokinase is predominantly present in tumours only.

Inhibitors of phosphoglucoisomerase: Phosphoglucoseisomerase transforms glucose 6-phosphate to fructose 6-phosphate. Such transformation requires the presence of an hydroxyl group at C-2. Therefore, analogs without hydroxyl or having the hydroxyl properly blocked will not undergo isomerization by phosphoglucose isomerase.

Another way to inhibit isomerization by phosphoglucose isomerase is by modifying the glucose 6-phosphate at C-1 or C-5 by substituting hydroxyl with a halogenated atom (fluorine, glucosyl fluoride), or by simple deoxygenation to 1-deoxy-D-glucose.

Inhibitors of phosphoglucoisomerase are any known in the art and may include, but are not limited to any of the following:

(i) C2 substituted D-hexoses, such as 2-deoxy-2-halogeno-D-hexoses, such as 2-deoxy-2-fluoro-D-glucose (2FDG), 2-chloro-2-deoxy-D-glucose, 2-bromo-D-glucose, 2-iodo-D-glucose, 2-deoxy-2,2-difluoro-D-arabino-hexose, 2-deoxy-2-fluoro-D-mannose, 2-deoxy-D-arabino-hexose, 2-Deoxy-2-fluoro-D-galactose, 1,6-anhydro-2-deoxy-2-fluoro-beta-D-glucopyranose (1-6-anhydrosugar), 2-amino-2-deoxy-D-glucose (glucose amine), 2-amino-2-deoxy D galactose (galactosamine), 2-amino-2-deoxy-D-mannose (mannosamine), 2-deoxy-2-fluoro-D-mannose, 2-deoxy-2-fluoro-D-galactose, 2-deoxy-D-arabino-hexose, 2-deoxy-2,2-difluoro-D-arabino-hexose, 2-deoxy-2-fluoro-D-glucose 1-Phosphate, 2-deoxy-2-fluoro-D-glucose 6-P, 2-deoxy-2-fluoro-D-glucose 1,6 biphosphate, 2-deoxy-2-fluoro-D-mannose 1-P, 2-deoxy-2-fluoro-D-mannose 6-P, 2-deoxy-2-fluoro-D-mannose 1,6-biphosphate, nucleotide diphosphate (for example uridine di-P)-2deoxy-2-fluoro-D-glucose, mannose.
  (ii) C-2-halogen substituted, and NH3 substituted derivatives of D-Glucose 6-phosphate, 2-deoxy-2-fluoro-2-D-glucose-6-phosphate, 2-chloro-2-deoxy-D-glucose-6-phosphate, 2-deoxy-D-arabino-hexose-6-phosphate, D-glucosamine-6-phosphate, 2-deoxy-2-fluoro-2-D-manose-6-P, and any known derivatives.
  (iii) C-2 halogenated derivatives of hexose ring pyranoses (mannopyranoses, galactopyranoses), for instance C-2-deoxy-2-fluoro-D-pyranoses, and any known in the art.
  (iv) Halogenated (fluoro, bromo, chloro, iodo) C2 sugars derivatives such as gluconolactones, glucuronic acid, glucopyranoside, and their phosphate derivatives.
  (v) Modification at C-1 or C-5: replacement of hydroxyl by fluorine or deoxygenation or replacement by a sulfur group in C-5, such as but not limited to glucosyl fluoride, 1-deoxy-D-glucose, 5-thio-D-glucose.
  (vi) 6-aminonicotinamide (6AN), indirectly by the inhibition of the PPP.

Inhibitors of phosphofructokinase (or fructose-6-P kinase) are any known in the art and may include, but are not limited to any of the following: Acidosis-inducing agents, 2-deoxy-2-fluoro-D-glucose, citrate and halogenated derivatives of citrate, fructose 2,6-bisphosphate, bromoacetylethanolamine phosphate analogues (N-(2-methoxyethyl)-bromoacetamide, N-(2-ethoxyethyl)-bromoacetamide, N-(3-methoxypropyl)-bromoacetamide).

Inhibitors of aldolase: Analogs blocking the aldolase cleavage, thus blocking formation of trioses from fructose 1,6-bisphosphate require the presence of hydroxyl groups at C-3 and C-4. Thus, for example, 3-deoxy or 3-fluoro-D-glucose or 4-deoxy or 4-fluoro-D-glucose can be transformed to 4-fluoro-D-fructose 1,6-bisphosphate, which will not be cleaved by aldolase but will block it.

Inhibitors of glyceraldehyde 3P deshydrogenase are any known in the art and may include, but are not limited to any of the following: Iodoacetate, pentalenolactone, arsenic, 1,1-difluoro-3-phosphate-glycerol.

Inhibitors of the transformation chain of glyceraldehyde (glyceraldehyde 3P deshydrogenase, phosphoglycerate kinase, phosphoglycerate mutase, enolase) are any which act at any step where phosphorylation is involved. Such inhibitors are any known in the art and may include, but are not limited to any of the following: either 2-fluoro (or iodo, or thio, or methoxy) or 3-fluoro (or 3,3 difluoro, 3-iodo, 3-carboxylo-, 3-thio)-glyceraldehydes or glycerates, 3-fluoro-2-phosphoglycerate, also, phosphothioesters or other phosphorous-modified analogs can block the transformations of glyceraldehyde.

Inhibitors of pyruvate kinase are any known in the art. Alternatively, a composition comprising serine or fructose 1,6-diP shifts the glycolytic pathway towards the TCA cycle; thus a composition of the invention comprises serine and an inhibitor of the TCA such as fluoroacetate or an inhibitor of the oxidative phosphorilation such as rhodamine.

Inhibitors of pyruvate carboxylase and PEP carboxylase, triose phosphate isomerase, phosphoglycerate kinase, enolase, phosphoglycerate mutase and triose phosphate isomerase are any known in the art.

Inhibitors of lactate deshydrogenase are any known in the art and may include, but are not limited to oxamate, 2-fluoropropionic acid or its salts; 2,2-difluoro-propionic acid, pyruvate modified at C-3 such as, but not limited to 3-halo-pyruvate, 3-halopropionic acid and 2-thiomethylacetic acid.

In some embodiments, an inhibitor of glycolysis is any of 2FDG, oxamate and iodoacetate.

Glycolysis is the main pathway for anaerobic ATP synthesis. Tumours switch to anaerobic ATP synthesis by metabolizing the well-distributed glucose among others in order to provide nucleotides through the PPP pathway. It is known that proliferating masses which are partly under anaerobic type respiration are more resistant to radiation or chemotherapy. Therefore, by locally inhibiting the glycolysis pathway, anaerobic respiration which is the principal energy pathway of poorly oxygenated cells is inhibited, leading to increased cell death of hypoxic proliferating cells. The proliferation of non-hypoxic cells is slowed as well owing to the shutdown of this primary energy pathway.

IV. Generation of Cells Having a Second Cell Fate

In one aspect, the present invention provides methods for differentiating cells into a desired cell fate. As shown in the Examples, the inventors can generate differentiated cells, i.e., cells having a second cell fate, of any of the three major lineages (endoderm, mesoderm, ectoderm). A number of differentiation protocols (i.e., protocols comprising contacting cells with lineage-specific differentiation factors) are known for differentiating cells into cell fates and it is believed that such protocols can generally be applied to cells generated as described above in sections II and III to generate differentiated cells. In some embodiments, the differentiation protocol includes only chemically defined media.

In some embodiments, the methods of sections II and III are performed continuously, i.e., without significant intervening steps. For example, in some embodiments, transition between steps simply involves a change of media.

A. Mesodermal Differentiation

In some embodiments, cells are differentiated into mesodermal cells. In some embodiments, cells are differentiated into cardiac cells (e.g., cardiomyocytes). In combination with the methods described above in sections II and III, it is believed that one can use any method for inducing cardiomyocytes as desired. In some embodiments, the conditions include a chemically defined medium. In some embodiments, non-mesodermal cells (e.g., ectodermal cells, e.g., fibroblasts) are exposed (e.g., via expression or protein contact) to reprogramming transcription factors for, e.g., 3-10, 3-6 days, etc., optionally in the presence of a JAK inhibitor (e.g., at a sufficient concentration to prevent development of iPS cells). At the end of this period, cells can be (e.g., directly) moved to conditioning media to convert the cells to mesodermal cells as described herein.

In some embodiments, the cardiomyocytes are induced by contacting a cell (for example, a cell as generated in section II and/or III above, or if desired, an induced pluripotent cell or other pluripotent or progenitor cell) with a BMP protein, a calcium channel agonist, a Gαs activating agent, a cAMP analog, and/or a GSK-3 inhibitor under conditions to generate cardiomyocytes. In some embodiments, the cardiomyocytes are induced by contacting a cell (for example, a cell as generated in section II and/or III above, or if desired, an induced pluripotent cell, other pluripotent or progenitor cell) with bone morphogenic protein-4 (BMP4) and/or an GSK-3 inhibitor under conditions to generate cardiomyocytes. In some embodiments, the conditions include a chemically defined medium. In some embodiments, for example, a chemically defined medium includes RPMI-1640 supplemented with 0.5×N2, 1× B27 (without vitamin A), 0.05% BSA fraction V, 0.5% Glutamax, and 0.1 mM β-mercaptoethanol (Invitrogen).

The BMP protein (e.g., BMP4) applied to the cells can be from any of a number of organisms, though in many embodiments, the species origin of the BMP protein (e.g., BMP4) will match the species of cell used. Thus for example, in some embodiments, a human cell is contacted with human BMP protein (e.g., BMP4), a mouse cell is contacted with mouse BMP protein (e.g., BMP4), etc. It will be appreciated that active mutants and fragments of BMP protein (e.g., BMP4) can also be used.

In some embodiments, the cardiomyocytes can be induced by contacting a cell (for example, a cell as generated in section II and/or III above, or if desired an induced pluripotent cell or other pluripotent or progenitor cell) with bone morphogenic protein-4 (BMP4) without an GSK-3 inhibitor under conditions to generate cardiomyocytes. In some embodiments, the cardiomyocytes can also be induced by contacting a cell with a GSK-3 inhibitor without BMP4.

In some embodiments, the cardiomyocytes are induced by contacting a cell (for example, a cell as generated in section II and/or III above, or if desired an induced pluripotent cell or other pluripotent or progenitor cell) with a L-type calcium channel agonist. Exemplary L-type calcium channel agonists include, but are not limited to, BayK8644 (see, e.g., Schramm, et al., *Nature* 303:535-537 (1983)), Dehydrodidemnin B (see, e.g., U.S. Pat. No. 6,030,943), FPL 64176 (FPL) (see, e.g., Liwang, et al., *Neuropharmacology* 45:281-292 (2003)), S(+)-PN 202-791 (see, e.g., Kennedy, et al., *Neuroscience* 49:937-44 (1992)) and CGP 48506 (see, e.g., Chahine, et al., *Canadian Journal of Physiology and Pharmacology* 81:135-141 (2003)).

In some embodiments, the cardiomyocytes are induced by contacting a cell (for example, a cell as generated in section II and/or III above, or if desired an induced pluripotent cell or other pluripotent or progenitor cell) with a Gαs activating agent. Exemplary Gαs activating agents include, but are not limited to, isoproterenol, epinephrine, cimaterol, clenbuterol, dobutamine, alprenolol, cyanopindolol, propanolol, sotalol, timolol, and ICI-118,551 (3-isoprophylamino)-1-[(7-methyl-4-indanyl)oxy]butan-2-ol (see, e.g., Uğur et al., *Mol Pharmacol* 68:720-28 (2005)).

In some embodiments, the cardiomyocytes are induced by contacting a cell (for example, a cell as generated in section II and/or III above, or if desired an induced pluripotent cell or other pluripotent or progenitor cell) with a cAMP analog. Exemplary cAMP analogs include, but are not limited to, dibutyryl cAMP, 8-Bromo-cAMP, and Sp-8-Br-cAMPS (8-bromoadenosine-3',5'-cyclic monophosphorothioate, Sp-isomer) (see, e.g., Ferrier and Howlett, *J. Pharmacol. Exp. Ther.* 306:166-76 (2003)).

The GSK-3 inhibitor used in the methods of mesodermal differentiation described herein can be a GSK-3 isoform specific inhibitor, e.g., a GSK-3β or a GSK-3α inhibitor, or a isoform non-specific inhibitor. In some embodiments, the GSK-3 inhibitor can be substituted with a GSK inhibitor. In some embodiments, the GSK-3 inhibitor can be substituted with a Wnt inhibitor or a Wnt pathway inhibitor.

Wnt Inhibitors

By "Wnt pathway" is meant to include any of the proteins downstream or upstream of Wnt protein activity. For example, this could include LRP5, LRP6, Dkk, GSK-3, Wnt10B, Wnt6, Wnt3 (e.g., Wnt 3A), Wnt1 or any of the other proteins discussed herein, and the genes that encode these proteins. Discussion of the Wnt pathway also is meant to include all of the pathways downstream of Wnt, such as the LRP5 or HBM pathways, the Dkk pathway, the β-catenin pathway, the MAPKAPK2 pathway, the OPG/RANK pathway, and the like. By "LRP5 pathway" and "IBM pathway" is meant any proteins/genes including LRP5 or the HBM mutant and proteins downstream of LRP5 or the HBM mutant. By "β-catenin pathway" is meant any proteins/genes including β-catenin and proteins downstream of β-catenin. By "MAPKAPK2 pathway" is meant any proteins/genes including MAPKAPK2 and proteins downstream of MAPKAPK2. By "OPG/RANKL pathway" is meant any proteins/genes including OPG/RANKL and proteins downstream of OPG and RANKL. By "Dkk pathway" is meant to include any proteins/genes involved in Dkk-1 and LRP5 and/or LRP6 interaction that is part of the Wnt pathway. Dkk-1 inhibits LRP5 activity.

Exemplary Wnt inhibitors include, but are not limited to, e.g., IWP-2 (2-(3,4,6,7-tetrahydro-4-oxo-3-phenylthieno[3,2-d]pyrimidin-2-ylthio)-N-(6-methylbenzo[d]thiazol-2-yl) acetamide), DKK1 (Dickkopf protein 1), and IWR1

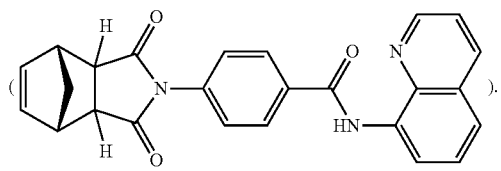 [SMILES: O=C(Nc1cccc2cccnc12)c1ccc(N2C(=O)C3C(C2=O)[C@H]2C=C[C@@H]3C2)cc1]

IWP-2 was identified in a high throughput screen for antagonists of the Wnt/β-catenin pathway (Chen, et al., *Nat Chem Biol* 5: 100-7, 2009). Wnt Inhibitor IWP-2 prevents palmitylation of Wnt proteins by Porcupine (Porcn), a membrane-bound O-acyltransferase, thereby blocking Wnt secretion and activity. It has an $IC_{50}$ of 27 nM and blocks phosphorylation of the Lrp6 receptor and accumulation of both Dvl2 and β-catenin (Chen, et al., *Nat Chem Biol* 5: 100-7, 2009). Wnt inhibitor IWR1 induces an increase in Axin2 protein levels; promotes β-catenin phosphorylation by stabilizing Axin-scaffolded destruction complexes (Chen, et al., *Nat Chem Biol* 5: 100-7, 2009; Lu et al., *Bioorg. Med. Chem. Lett.* 19:3825, 2009). Additional Wnt inhibitors include, but are not limited to, IWR compounds, IWP compounds and other Wnt inhibitors described in WO09155001 and Chen, et al., *Nat Chem Biol* 5: 100-7, 2009.

Known antagonists of Wnt signaling also include Dickkopf proteins, secreted Frizzled-related proteins (sFRP), Wnt Inhibitory Factor 1 (WIF-1), and Soggy. Members of the Dickkopf-related protein family (Dkk-1 to -4) are secreted proteins with two cysteine-rich domains, separated by a linker region. Dkk-3 and -4 also have one prokineticin domain. Dkk-1, -2, and -4 function as antagonists of canonical Wnt signaling by binding to LRP5/6, preventing LRP5/6 interaction with Wnt-Frizzled complexes. Dkk-1, -2, and -4 also bind cell surface Kremen-1 or -2 and promote the internalization of LRP5/6. Antagonistic activity of Dkk-3 has not been demonstrated. Dkk proteins have distinct patterns of expression in adult and embryonic tissues and have a wide range of effects on tissue development and morphogenesis. The Dkk family also includes Soggy, which is homologous to Dkk-3 but not to the other family members. The sFRPs are a family of five Wnt-binding glycoproteins that resemble the membrane-bound Frizzleds. The largest family of Wnt inhibitors, they contain two groups, the first consisting of sFRP-1, 2, and 5, and the second including sFRP-3 and 4. All are secreted and derived from unique genes, none are alternate splice forms of the Frizzled family. Each sFRP contains an N-terminal cysteine-rich domain (CRD). Other antagonists of Wnt signaling include WIF-1 (Wnt Inhibitory Factor 1), a secreted protein that binds to Wnt proteins and inhibits their activity.

GSK Inhibitor

By "GSK inhibitor" is meant any agent which inhibits GSK activity. These can include non-selective GSK inhibitors, such as LiCl or other lithium salts, as well as selective GSK inhibitors. In some embodiments, GSK inhibitors are GSK-3 inhibitors. In some embodiments, GSK inhibitors are GSK-3 isoform specific inhibitors, such as GSK-3β or GSK-3α inhibitors. Additional inhibitors include but are not limited to monoclonal or polyclonal antibodies or immunogenically active fragments thereof, peptide aptamers, a GSK binding protein, an antisense molecule to a GSK nucleic acid, an RNA interference molecule, a morpholino oligonucleotide, a peptide nucleic acid (PNA), a ribozyme, and a peptide.

As noted in the example, in some embodiments, the GSK-3 inhibitor is BIO (6-bromoindirubin-3'-oxime) as follows:

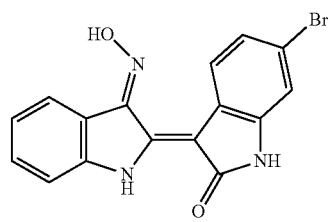 [SMILES: O=C1Nc2cc(Br)ccc2/C1=C1/Nc2ccccc2/C1=N\O]

In some embodiments, the GSK-3 inhibitor is a BIO derivative having general formula:

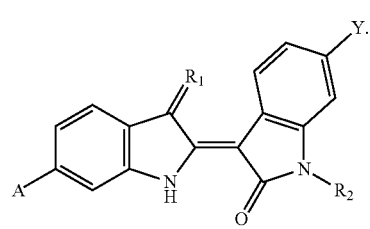

In the Formula (I), —X and —Y is —H or a halogen, e.g., —Br. $R_1$ is selected from the group consisting of oxo,

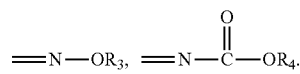

$R_2$, $R_3$, $R_4$ are independently hydrogen, substituted or unsubstituted alkyl (e.g., substituted or unsubstituted $C_1$ to $C_{20}$ alkyl), substituted or unsubstituted heteroalkyl (e.g., substituted or unsubstituted 2 to 20 membered heteroalkyl), substituted or unsubstituted cycloalkyl (e.g., $C_3$ to $C_{14}$ cycloalkyl including fused ring structures), substituted or unsubstituted heterocycloalkyl (e.g., 3 to 14 membered heterocycloalkyl including fused ring structures), substituted or unsubstituted aryl (e.g., a $C_6$ to $C_{14}$ aryl including fused ring structures), or substituted or unsubstituted heteroaryl (e.g., 5 to 14 membered heteroaryl including fused rings structures). Additional BIO derivatives include, but are not limited to, those described in U.S. Publication No. 2007/0276025. In some embodiments, the GSK-3 inhibitor is an indirubin molecule substituted with a halogen at position C6 of the indirubin molecule. In some embodiments, the GSK-3 inhibitor is selected from the group consisting of 6-bromoindirubin, 6,6'-dibromoindimibin, 6-bromoindirubin-3'-oxime ("BIO"), 6,6'-dibromnoindirubin-3'-oxime, 6-bromoindirubin-3'-methoxime, 6-bromo-5-methylindirubin and 6-bromoindirubin-3'-acetoxime, 6-bromo-5-aminoindirubin and 6-bromo-5-amino-3'-oxime-indirubin, 6-bromoindirubin, 6,6'-dibromoindirubin, 6-bromoindirubin-3'-oxime ("BIO"), 6,6'-dibromoindirubin-3'-oxime, 6-bromoindirubin-3'-methoxime, 6-bromo-5-methylindirubin, 6-bromo-5-aminoindirubin, 6-bromo-5-amino-3'-oxime-indirubin, 6-bromoindirubin-3'-acetoxime, 5-amino-indirubin, 5-amino-3'-oxime-indirubin, and pharmaceutically acceptable salts thereof.

Other possible inhibitors of GSK-3 can include antibodies that bind, dominant negative variants of, and siRNA, microRNA, antisense nucleic acids, and other polynucleotides that target GSK-3. Specific examples of GSK-3 inhibitors include, but are not limited to, Kenpaullone, 1-Azakenpaullone, CHIR99021, CHIR98014, AR-A014418 (see, e.g., Gould, et al., *The International Journal of Neuropsychopharmacology* 7:387-390 (2004)), CT 99021 (see, e.g., Wagman, *Current Pharmaceutical Design* 10:1105-1137 (2004)), CT 20026 (see, Wagman, supra), SB216763 (see, e.g., Martin, et al., *Nature Immunology* 6:777-784 (2005)), AR-A014418 (see, e.g., Noble, et al., *PNAS* 102:6990-6995 (2005)), lithium (see, e.g., Gould, et al., *Pharmacological Research* 48: 49-53 (2003)), SB 415286 (see, e.g., Frame, et al., *Biochemical Journal* 359:1-16 (2001)) and TDZD-8 (see, e.g., Chin, et al., Molecular Brain Research, 137(1-2):193-201 (2005)). Further exemplary GSK-3 inhibitors available from Calbiochem (see, e.g., Dalton, et al., WO2008/094597, herein incorporated by reference), include but are not limited to BIO (2'Z,3'£)-6-Bromoindirubin-3'-oxime (GSK-3 Inhibitor IX); BIO-Acetoxime (2'Z,3'E)-6-Bromoindirubin-3'-acetoxime (GSK-3 Inhibitor X); (5-Methyl-1H-pyrazol-3-yl)-(2-phenylquinazolin-4-yl)amine (GSK-3-Inhibitor XIII); Pyridocarbazole-cyclopenadienylruthenium complex (GSK-3 Inhibitor XV); TDZD-8 4-Benzyl-2-methyl-1,2,4-thiadiazolidine-3,5-dione (GSK-3β Inhibitor I); 2-Thio(3-iodobenzyl)-5-(1-pyridyl)-[1,3,4]-oxadiazole (GSK-3β Inhibitor II); OTDZT 2,4-Dibenzyl-5-oxothiadiazolidine-3-thione (GSK-3β Inhibitor III); alpha-4-Dibromoacetophenone (GSK-3β Inhibitor VII); AR-AO 14418 N-(4-Methoxybenzyl)-N'-(5-nitro-1,3-thiazol-2-yl)urea (GSK-3β Inhibitor VIII); 3-(1-(3-Hydroxypropyl)-1H-pyrrolo[2,3-b]pyridin-3-yl]-4-pyrazin-2-yl-pyrrole-2,5-dione (GSK-3β Inhibitor XI); TWS1 19 pyrrolopyrimidine compound (GSK-3β Inhibitor XII); L803 H-KEAPPAPPQSpP-NH2 (SEQ ID NO:9) or its Myristoylated form (GSK-3β Inhibitor XIII); 2-Chloro-1-(4,5-dibromo-thiophen-2-yl)-ethanone (GSK-3β Inhibitor VI); AR-AO144-18; SB216763; and SB415286. Residues of GSK-3β that interact with inhibitors have been identified. See, e.g., Bertrand et al., *J. Mol Biol.* 333(2): 393-407 (2003).

Those of skill will appreciate that the concentration of the GSK-3 inhibitor will depend on which specific inhibitor is used. In certain embodiments, a combination of two or more different GSK-3 inhibitors can be used.

B. Ectodermal Differentiation

In some embodiments, cells are differentiated into ectodermal cells. In some embodiments, cells are differentiated into neural cells. In some embodiments, cells are differentiated into neural progenitor cells. In some embodiments, cells are differentiated into tyrosine hydroxylase (TH)-positive neuronal cells. In some embodiments, cells are differentiated into retinal pigmented epithelium cells. In combination with the methods described above in sections II and III, it is believed that one can use any method for inducing differentiation into ectodermal cells as desired. In some embodiments, the conditions include a chemically defined medium. In some embodiments, non-ectodermal cells are exposed (e.g., via expression or protein contact) to reprogramming transcription factors for, e.g., 3-10, 3-6 days, etc., optionally in the presence of a JAK inhibitor (e.g., at a sufficient concentration to prevent development of iPS cells). At the end of this period, cells can be (e.g., directly) moved to conditioning media to convert the cells to ectodermal cells as described herein.

In some embodiments, differentiation into neural cells is induced by contacting a cell (for example, a cell as generated in section II and/or III above, or if desired an induced pluripotent cell or other pluripotent or progenitor cell) with a Wnt inhibitor or a Wnt pathway inhibitor as used in the methods of mesodermal differentiation (e.g., IWP-2, DKK1, and IWR1) under conditions to generate neural cells. In some embodiments, neural cells (e.g., neural progenitor cells) are induced by contacting a cell (for example, a cell as generated in section II and/or III above, or if desired an induced pluripotent cell or other pluripotent or progenitor cell) with FGF2, FGF4, and EGF under conditions to generate neural cells (e.g., neural progenitor cells). In some embodiments, neural cells (e.g., TH-positive neuronal cells) are induced by contacting a cell (for example, a cell as generated in section II and/or III above, or if desired an induced pluripotent cell or other pluripotent or progenitor cell) with FGF8 and SHH under conditions to generate neural cells (e.g., TH-positive neuronal cells). In some embodiments, the conditions include a chemically defined medium. In some embodiments, a chemically defined medium includes an Advanced DMEM/F12 and Neurobasal 1:1 mixture supplemented with 0.05% bovine serum albumin, 1×N2, 1× B27, 2 mM Glutamax, and 0.11 mM β-mercaptoethanol.

In some embodiments, differentiation into retinal pigmented epithelium cells is induced by contacting a cell (for example, a cell as generated in section II and/or III above, or if desired an induced pluripotent cell or other pluripotent or progenitor cell) with FGF2, FGF4, and EGF under conditions to generate a neural progenitor cell (e.g., as described above), and contacting the neural progenitor cell with a TGFβ inhibitor and a GSK-3 inhibitor under conditions to generate the retinal pigmented epithelium cell. In some embodiments, the conditions include a chemically defined medium.

In some embodiments, growth factors generally known and used in cell differentiation, e.g., neural cell differentiation, can be used for ectodermal differentiation according to the present invention. In some embodiments, the method involves contacting cells with FGF2, FGF4 and/or EGF to generate neural cells. In some embodiments, the method involves contacting cells with FGF8 and SHH to generate neural cells.

In some embodiments, GSK-3 inhibitors, for example a GSK-3 isoform specific inhibitor, e.g., a GSK-3β or a GSK-3α inhibitor, or a isoform non-specific inhibitor, can be used for ectodermal differentiation (e.g., retinal pigmented epithelium cell differentiation) according to the present invention. In some embodiments, the GSK-3 inhibitor can be substituted with a GSK inhibitor. In some embodiments, the GSK-3 inhibitor can be substituted with a Wnt inhibitor or a Wnt pathway inhibitor. Suitable GSK-3 inhibitors and/or Wnt inhibitors and/or Wnt pathway inhibitors are described above. In some embodiments, a TGFβ inhibitor can be used for ectodermal differentiation (e.g., retinal pigmented epithelium cell differentiation) according to the present invention. Suitable TGFβ inhibitors are described infra.

C. Endodermal Differentiation

In some embodiments, cells are differentiated into endodermal cells. In some embodiments, cells are differentiated into pancreatic cells (e.g., pancreatic lineage cells or pancreatic beta cells). In some embodiments, cells are differentiated into induced definitive endoderm (iDE) cells. In combination with the methods described above in sections II and III, it is believed that one can use any method for inducing differentiation into endodermal cells as desired. In some embodiments, the conditions include a chemically defined medium. In some embodiments, non-endodermal cells (e.g., ectodermal cells, e.g., fibroblasts) are exposed (e.g., via expression or protein contact) to reprogramming transcription factors for, e.g., 3-10, 3-6 days, etc., optionally in the presence of a JAK inhibitor (e.g., at a sufficient concentration to prevent development of iPS cells). At the end of this period, cells can be (e.g., directly) moved to conditioning media to convert the cells to endodermal cells as described herein.

In some embodiments, differentiation into pancreatic cells is induced by contacting a cell (for example, a cell as generated in section II and/or III above, or if desired an induced pluripotent cell or other pluripotent or progenitor cell) with a TGFβ/Activin/Nodal pathway inhibitor (e.g., A-83-01 or SB431542) under conditions to generate pancreatic cells. In some embodiments, differentiation into pancreatic lineage cells is induced by contacting a cell (for example, a cell as generated in section II and/or III above, or if desired an induced pluripotent cell or other pluripotent or progenitor cell) with a TGFβ/Activin/Nodal family member optionally in the presence of a JAK inhibitor, then contacting the cell with a TGFβ/ALK5 inhibitor (e.g., SB431542), then contacting the cell with nicotinamide under conditions to generate the pancreatic lineage cell.

In some embodiments, differentiation into an induced definitive endoderm (iDE) cell is induced by contacting a cell (for example, a cell as generated in section II and/or III above, or if desired an induced pluripotent cell or other pluripotent or progenitor cell) with a TGFβ/Activin/Nodal pathway inhibitor (e.g., A-83-01 or SB431542), an HDAC inhibitor (e.g., NaB), and/or a GSK-3 inhibitor (e.g., CHIR99021) under conditions to generate the iDE cell. In some embodiments, differentiation into a pancreatic beta cell is induced by contacting a cell (for example, a cell as generated in section II and/or III above, or if desired an induced pluripotent cell or other pluripotent or progenitor cell) with a TGFβ/Activin/Nodal pathway inhibitor (e.g., A-83-01 or SB431542), an HDAC inhibitor (e.g., NaB), and/or a GSK-3 inhibitor (e.g., CHIR99021) under conditions to generate the iDE cell, then under conditions to generate pancreatic beta cells, contacting the cell with FGF7, retinoic acid (RA), a Hedgehog pathway inhibitor (e.g., GDN-0449), a BMP inhibitor (e.g., LDN-193189), and/or a TGFβ/ALK5 inhibitor (e.g., SB431542), then contacting the cell with EGF and/or a Notch inhibitor (e.g., DAPT), then contacting the cell with bFGF, nicotinamide, and/or extendin-4.

In some embodiments, the conditions include a chemically defined medium. In some embodiments, for example, a chemically defined medium includes RPMI-1640 supplemented with 0.5×N2, 1× B27 (without vitamin A), 0.05% BSA fraction V, 0.5% Glutamax, and 0.1 mM β-mercaptoethanol (Invitrogen).

Growth factors generally known and used in cell differentiation, e.g., pancreatic cell differentiation, can be used for endodermal differentiation accordingly to the present invention. In some embodiments, the method involves contacting cells with bFGF, BMP4, EGF, and/or FGF7 to generate endodermal cells.

Small molecules generally known and used in cell differentiation, e.g., pancreatic cell differentiation, can be used for endodermal differentiation accordingly to the present invention. In some embodiments, pancreatic cell differentiation is induced by incubating the cells (for example, a cell as generated in section II and/or III above, or if desired an induced pluripotent cell, other pluripotent or progenitor cell) with a sufficient amount of a GSK inhibitor, an HDAC inhibitor and/or a TGFβ/activin pathway inhibitor (e.g., A-83-01).

TGFβ/Activin/Nodal Pathway Inhibitors

Exemplary TGFβ/activin pathway inhibitors include but are not limited to: TGF beta receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described below are merely for organizational purposes and one of skill in the art would know that compounds can affect one or more points within a pathway, and thus compounds may function in more than one of the defined categories.

Inhibitors of SMAD 2/3 phosphorylation can include antibodies to, dominant negative variants of and antisense nucleic acids that target SMAD2 or SMAD3. Specific examples of inhibitors include PD169316; SB203580; SB-431542; LY364947; A77-01; and 3,5,7,2',4'-pentahydroxyflavone (Morin). (See, e.g., Wrzesinski, supra; Kaminska, supra; Shimanuki, et al., *Oncogene* 26:3311-3320 (2007); and Kataoka, et al., EP1992360, incorporated herein by reference.)

Inhibitors of the interaction of SMAD 2/3 and SMAD 4 can include antibodies to, dominant negative variants of and antisense nucleic acids that target SMAD2, SMAD3 and/or smad4. Specific examples of inhibitors of the interaction of SMAD 2/3 and SMAD4 include but are not limited to Trx-SARA, Trx-xFoxH1b and Trx-Lef1. (See, e.g., Cui, et al., *Oncogene* 24:3864-3874 (2005) and Zhao, et al., *Molecular Biology of the Cell,* 17:3819-3831 (2006).)

Activators/agonists of SMAD 6 and SMAD 7 include but are not limited to nucleic acids encoding SMAD 6 or SMAD 7 proteins or fragments thereof and polypeptides and fragments encoded by said nucleic acids. (See, e.g., Miyazono, et al., U.S. Pat. No. 6,534,476, incorporated herein by reference.)

In other embodiments, the differentiation into pancreatic cells are induced by contacting a cell (for example, a cell as generated in section II and/or III above, or if desired an induced pluripotent cell, other pluripotent or progenitor cell) with a TGFβ receptor/ALK5 inhibitor under conditions to generate pancreatic cells. TGF beta receptor (e.g., ALK5) inhibitors can include antibodies to, dominant negative variants of, and antisense nucleic acids that suppress expression of, TGF beta receptors (e.g., ALK5). Exemplary TGFβ receptor/ALK5 inhibitors include, but are not limited to, SB431542 (see, e.g., Inman, et al., *Molecular Pharmacology* 62(1):65-74 (2002)), A-83-01, also known as 3-(6-Methyl-2-pyridinyl)-N-phenyl-4-(4-quinolinyl)-1H-pyrazole-1-carbothioamide (see, e.g., Tojo, et al., *Cancer Science* 96(11): 791-800 (2005), and commercially available from, e.g., Toicris Bioscience); 2-(3-(6-Methylpyridin-2-yl)-1H-pyrazol-4-yl)-1,5-naphthyridine, Wnt3a/BIO (see, e.g., Dalton, et al., WO2008/094597, herein incorporated by reference), BMP4 (see, Dalton, supra), GW788388 (-{4-[3-(pyridin-2-yl)-1H-pyrazol-4-yl]pyridin-2-yl}-N-(tetrahydro-2H-pyran-4-yl)benzamide) (see, e.g., Gellibert, et al., *Journal of Medicinal Chemistry* 49(7):2210-2221 (2006)), SM16 (see, e.g., Suzuki, et al., *Cancer Research* 67(5):2351-2359 (2007)), IN-1130 (3-((5-(6-methylpyridin-2-yl)-4-(quinoxalin-6-yl)-1H-imidazol-2-yl)methyl)benzamide) (see, e.g., Kim, et al., *Xenobiotica* 38(3):325-339 (2008)), GW6604 (2-phenyl-4-(3-pyridin-2-yl-1H-pyrazol-4-yl)pyridine) (see, e.g., de Gouville, et al., *Drug News Perspective* 19(2):85-90 (2006)), SB-505124 (2-(5-benzo[1,3]dioxol-5-yl-2-tert-butyl-3H-imidazol-4-yl)-6-methylpyridine hydrochloride) (see, e.g., DaCosta, et al., *Molecular Pharmacology* 65(3): 744-752 (2004)) and pyrimidine derivatives (see, e.g., those listed in Stiefl, et al., WO2008/006583, herein incorporated by reference). Further, while "an ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman, et al., *J, Mol. Phamacol.* 62(1): 65-74 (2002). Without intending to limit the scope of the invention, it is believed that ALK5 inhibitors affect the mesenchymal to epithelial conversion/transition (MET) process. TGFβ/activin pathway is a driver for epithelial to mesenchymal transition (EMT). Therefore, inhibiting the TGFβ/activin pathway can facilitate MET (i.e., reprogramming) process.

TGF beta receptor inhibitors can include antibodies to, dominant negative variants of and siRNA or antisense nucleic acids that target TGF beta receptors. Specific examples of inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID11; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyflavone (Morin); activin-M108A; P144; soluble TBR2-Fc; and antisense transfected tumor cells that target TGF beta receptors. (See, e.g., Wrzesinski, et al., *Clinical Cancer Research* 13(18):5262-5270 (2007); Kaminska, et al., *Acta Biochimica Polonica* 52(2):329-337 (2005); and Chang, et al., *Frontiers in Bioscience* 12:4393-4401 (2007).)

BMP Inhibitors

Exemplary BMP pathway inhibitors include, but are not limited to: Noggin, BMP receptor inhibitors, inhibitors of SMAD 1/5/8 phosphorylation, inhibitors of the interaction of SMAD 1/5/8 and SMAD 4, and activators/agonists of SMAD 6 and SMAD 7. The categorizations described below are merely for organizational purposes and one of skill in the art would know that compounds can affect one or more points within a pathway, and thus compounds may function in more than one of the defined categories.

Inhibitors of SMAD 1/5/8 phosphorylation include, but are not limited to, antibodies to, dominant negative variants, antisense nucleic acids, and small molecules that target SMAD 1, SMAD 5, or SMAD 8. Specific examples of inhibitors include LDN-193189 and Dorsomorphin (commercially available from, e.g., Stemgent).

Activators/agonists of SMAD 6 and SMAD 7 include, but are not limited to, nucleic acids encoding SMAD 6 or SMAD 7 proteins or fragments thereof and polypeptides and fragments encoded by said nucleic acids. (See, e.g., Miyazono, et al., U.S. Pat. No. 6,534,476, incorporated herein by reference.)

BMP receptor inhibitors include, but are not limited to, antibodies to, dominant negative variants of, siRNA or antisense nucleic acids, or small molecules that target BMP receptors. Specific examples of inhibitors include, but are not limited to, DMH-1, Dorsomorphin dihydrochloride, and LDN-193189 (commercially available, from, e.g., Tocris Biosciences).

Hedgehog Pathway Inhibitors

Exemplary Hedgehog pathway inhibitors include, but are not limited to: inhibitors of Hedgehog binding to its receptor and inhibitors of signaling proteins downstream of Hedgehog (e.g., Patched or Smoothened). Specific examples of Hedgehog pathway inhibitors include cyclopamine, KAAD-Cyclopamine, SANT-1, SANT-2, U18666A, JK184, GANT 58, GANT 61, and GDC-0449 (commercially available from, e.g., Stemgent and Tocris Biosciences). Hedgehog pathway inhibitors are also described in Wu et al., WO 2006/050351, incorporated herein by reference. Additional inhibitors include but are not limited to monoclonal or polyclonal antibodies or immunogenically active fragments thereof, peptide aptamers, a Hedgehog binding protein or protein that binds to a signaling protein downstream of Hedgehog, an antisense molecule to a Hedgehog nucleic acid or a nucleic acid encoding signaling protein downstream of Hedgehog, an RNA interference molecule, a morpholino oligonucleotide, a peptide nucleic acid (PNA), a ribozyme, and a peptide.

Notch Inhibitors

Exemplary Notch inhibitors include, but are not limited to: inhibitors of Notch ligands, inhibitors of Notch activation, and inhibitors of gamma-secretase. Specific examples of Notch pathway inhibitors include DAPT, LY411575, L-685458, RO429097, MK-0752, MRK-003, and [11-endo]-N-(5,6,7,8,9,10-hexahydro-6,9-methanobenzo[a][8]annulen-11-yl)-thiophene-2-sulfonamide. (See, e.g., Fan et al., *Cancer Res.*, 66:7445-52 (2006)). Additional inhibitors include but are not limited to monoclonal or polyclonal antibodies (e.g., against Notch or against Notch ligands) or immunogenically active fragments thereof, peptide aptamers, an antisense molecule to Notch, an RNA interference molecule, a morpholino oligonucleotide, a peptide nucleic acid (PNA), a ribozyme, and a peptide.

D. Markers

Differentiation can be monitored by the expression of differentiation markers. Typical differentiation markers can be used for characterization of the cells of the invention. For example, cardiac differentiation markers include, e.g., early-stage cardiac markers Brachyury (T) and Mesp1; mid-stage cardiac markers Flk1, Nkx2.5, Isl1, and Gata-4; late-stage cardiac markers Mlc2a, myosin (sarcomeric and MHCb), and cTroponin T. Neural stem cells markers include Sox1 Pax6, PLZF, Sox2, and Dach1. Markers for differentiated neurons include Tuj1, MAP2, Dcx, Neurofilament, NenN, and Synapsin. Markers for subtypes of differentiated neurons include TH, AchE, ChAT, Serotonin, VGluT, Nurr1, and GABA. Astrocyte (astroglial cells) markers include GFAP. Oligodendrocyte markers include CNPase, O1, and O4. Pancreatic differentiation markers include, e.g., early- or mid-stage pancreatic markers: Sox17, Foxa2, HNF4a, HNF1b, HNF6, Pax6, Sox9; and late-stage pancreatic markers: Pdx1, Nkx6.1, Nkx2.2, Isl1, MafA, c-peptide, and Insulin.

Methods known in the art can be used to characterize the cells of the invention. Gene expression levels can be detected by, e.g., real-time PCR or real-time RT-PCR (e.g., to detect mRNA), and/or by western blot or other protein detection technique. Other cell differentiation characteristics such as cell morphologies associated with differentiated stem cells can also be used for characterization of the cells of the invention. For example, in some embodiments, the cell has a neuron morphology, i.e., a round cell body having projections (axons/dendrites) greater than 2 times the diameter of the cell body. In some embodiments, the cell has a cardiomyocyte morphology, i.e., cells having cross striations formed by alternating segments of actin and myosin.

E. Administration

Any of the differentiated cells (allogenic or autologous) as described herein can be introduced into a subject. For example, the cells can be delivered to a particular tissue or organ of a subject in need thereof, to ameliorate or treat a disease or condition.

In some embodiments, when cardiac cells (e.g., cardiomyocytes) are generated, the cells can be useful for generating artificial heart tissue, e.g., for implanting into a mammalian subject. In some embodiments, the method is useful for replacing damaged heart tissue (e.g., ischemic heart tissue) and/or for stimulating endogenous stem cells or non-cardiomyocyte somatic cells resident in the heart to undergo cardiomyogenesis. Where a subject method involves introducing (implanting) a cardiomyocyte into an individual, allogenic or autologous transplantation can be carried out.

Individuals in need of treatment with cardiac cells (e.g., cardiomyocytes) generated as described herein include, but are not limited to, individuals having a congenital heart defect; individuals suffering from a condition that results in ischemic heart tissue, e.g., individuals with coronary artery disease; and the like. A subject method is useful to treat degenerative muscle disease, e.g., familial cardiomyopathy, dilated cardiomyopathy, hypertrophic cardiomyopathy, restrictive cardiomyopathy, or coronary artery disease with resultant ischemic cardiomyopathy.

Individuals in need of treatment with pancreatic cells generated as described herein include, but are not limited to, individuals having Type I or Type II diabetes or who are pre-diabetic or insulin resistant.

Individuals in need of treatment with neural cells generated as described herein include, but are not limited to, individuals having nerve damage, paralysis, etc.

Individuals in need of treatment with retinal pigmented epithelium cells generated as described herein include, but are not limited to, individuals having macular degeneration (e.g., age-related macular degeneration), photoreceptor dystrophy, or merTK dystrophy.

For administration to a mammalian host, a cardiomyocyte, pancreatic, or neuronal (or other cell having a second cell fate as described herein) population generated using a subject method can be formulated as a pharmaceutical composition. A pharmaceutical composition can be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in a subject pharmaceutical composition. The selection of a carrier will depend, in part, on the nature of the substance (i.e., cells or chemical compounds) being administered. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, antioxidants, chelating agents and/or inert gases, and/or other active ingredients.

In some embodiments, a population of cells having the second cell fate is encapsulated, according to known encapsulation technologies, including microencapsulation (see, e.g., U.S. Pat. Nos. 4,352,883; 4,353,888; and 5,084,350). Where the cell are encapsulated, in some embodiments the cells are encapsulated by macroencapsulation, as described in, e.g., U.S. Pat. Nos. 5,284,761; 5,158,881; 4,976,859; 4,968,733; 5,800,828 and published PCT patent application WO 95/05452. In some embodiments, a cell population having a second cell fate is present in a matrix.

The methods described herein can be applied in vitro (e.g., in culture) or partly or completely in vivo. In in vivo applications, in some embodiments, vectors, proteins and/or small molecules are targeted to one or more target cell in the body such that one or more reprogramming factors are increased in the target cells to generate a less differentiated cell. Alternatively, such less differentiated cells can be generated in vitro and then delivered to a target tissue or organ. In some embodiments, the resulting less differentiated cell is present in a tissue or organ and is induced to differentiate into the second cell fate due at least in part to endogenous signals from the tissue or organ itself. Alternatively, the less differentiated cells can be differentiated into the cells having the second cell fate, for example as described herein, albeit in vivo.

EXAMPLES

The following examples are offered to illustrate, but not to limit the claimed invention.

Example 1

Direct Reprogramming of Fibroblasts to a Cardiac Fate

Abstract

Here we show that conventional reprogramming towards pluripotency—overexpresssing Oct4, Sox2, Klf4, and c-Myc—can be shortcut and directed towards cardiogenesis in a fast and efficient manner. With as little as four days of transgene expression, mouse embryonic fibroblasts (MEFs) can be directly reprogrammed to spontaneously contracting patches of differentiated cardiomyocytes over a period of 11-12 days. Several lines of evidence suggest that a pluripotent intermediate is not involved. Our method represents a unique strategy that allows a transient, plastic developmental state established early in reprogramming to effectively serve as a cellular transdifferentiation platform, the utility of which likely extends beyond cardiogenesis. Our study has potentially wide-ranging implications for iPSC factor-based reprogramming and broadens the existing paradigm.

Introduction

The mammalian heart lacks significant regenerative capacity. In vitro generation of autologous cardiac cells for transplantation is a key area of study for the effective treatment of heart disease. A recent report of successful transdifferentiation of somatic cells to a cardiac fate in vitro (Ieda, M. et al., *Cell* 142, 375-86 (2010)) has raised the possibility that this process might eventually be used for cell-based cardiac therapy. However, speed and efficiency must first be improved, especially if the ultimate goal is to provide a faster and safer alternative to the re-differentiation of autologous induced pluripotent stem cells (iPSCs) (Schenke-Layland, K. et al., *Stem Cells* 26, 1537-46 (2008)).

We and others in the reprogramming field have often noted the very rare but generally reproducible appearance of various terminally differentiated cell types—including spontaneously contracting cardiac colonies—during the later stages of iPSC formation. In light of these observations, and because induced pluripotency is established in a step-wise and stochastic fashion (Hanna, J. et al., *Nature* 462, 595-601 (2009); Stadtfeld, M. et al., *Cell Stem Cell* 2, 230-40 (2008)), we hypothesized that it might be possible to modify the reprogramming process to favour such alternative outcomes. We reasoned that providing the appropriate developmental cues after an initial epigenetic "activation phase" may allow us to hijack conventional reprogramming at this early, unstable stage, and specifically shift the outcome towards cardiogenesis.

Results

Three-factor Reprogramming is Sufficient to Activate the Early Cardiac Program

To test the validity of our hypothesis and gauge technical feasibility, we virally transduced MEFs harbouring a Nebulette-LacZ reporter expressed only in nascent myocardium (Cai, C. L. et al., *Development* 132, 2475-87 (2005)) with the four Yamanaka factors (Takahashi, K. and Yamanaka, S., *Cell* 126, 663-76 (2006)) and colorimetrically monitored early cardiogenesis. We modified standard reprogramming medium by removing leukaemia inhibitory factor (LIF) to avoid the generation and/or maintenance of pluripotent cells. We also tried different basement membranes (gelatin, fibronectin, Matrigel, or Geltrex) and the addition of foetal bovine serum (FBS) at concentrations of 1-15% to increase cell viability and/or the cardio-inductive properties of the medium. When cells were cultured on Matrigel or Geltrex in LIF-free medium containing 5% FBS, we observed transient (≤2 days) but wide-spread (approx. 50%) β-galactosidase expression in nascent colonies after a week. Importantly, systematic omission of factors from the viral cocktail revealed that c-Myc was dispensable, i.e., three-factor transduction worked equally well (FIG. 1a).

Induction of Spontaneous Contraction Requires Growth Factor Signalling and is Enhanced by a Small Molecule Having successfully initiated the early cardiogenic program in MEFs, we next sought to induce robust activation of mid-stage cardiac gene expression and to ultimately generate spontaneously contracting patches of cardiac cells, a hallmark of terminal differentiation that is easily observed and quantified. To this end, we treated three-factor transduced MEFs with chemically defined media (CDM) as well as cytokines and small molecules that might enhance cardiogenesis by regulating TGFβ, bone morphogenetic protein (BMP), Hedgehog, Wnt, or Notch pathway activity. Treatments were done individually and in combination, and at different times during the reprogramming process. Despite the general unsuitability of the resulting protocol for iPSC generation, we also explored whether small-molecule inhibition of JAK-STAT (Janus kinase-signal transducer and activator of transcription), PI3K (phosphatidylinositol 3-kinase), or Wnt signalling during the early stages of the protocol might boost the effectiveness of cardiomyogenesis by preventing even a small number of iPSC intermediates from forming. Finally, we experimented with a more gradual transition between different media by lowering FBS concentration stepwise in increments of 1-4% over 3-6 days (immediately prior to switching to CDM). After several rounds of experimentation employing many different combinations, we determined the following conditions to be the most effective: cells are first exposed to reprogramming media containing 15% FBS and 5% knockout serum replacer (KSR) for six days, followed by a switch to 1% FBS and 14% KSR for three days. During this initial nine-day period, the small-molecule JAK inhibitor JI1 is continuously kept in the media at a concentration of 0.5 μM. From day nine onwards, the cells are cultured in CDM, with the cardioinductive growth factor BMP4 (Snyder, A. et al., *J Cell Biochem* 93, 224-32 (2004)) being added at 20 ng/ml for the first five days (FIG. 1b).

Using three-factor transduction with the above conditions, we observed robust expression of the mid-stage cardiac markers (Martin-Puig, S. et al., *Cell Stem Cell* 2, 320-31 (2008)) Flk1, Nkx2.5, and Gata-4 starting on days 9-10 (FIG. 1c). Late-stage markers including cardiac troponin T, sarcomeric myosin heavy chain, and α-actinin were observed from day 11 onwards. Simultaneously, Connexin-43 staining became apparent along many cells' periphery. Interestingly, regardless of the time point at which ICC was performed, we only detected the atrial isoform of myosin light chain (Mlc-2a), indicating that the cardiomyocytes being generated were mostly, if not exclusively, of the atrial subtype (FIG. 1d).

Figure 2:
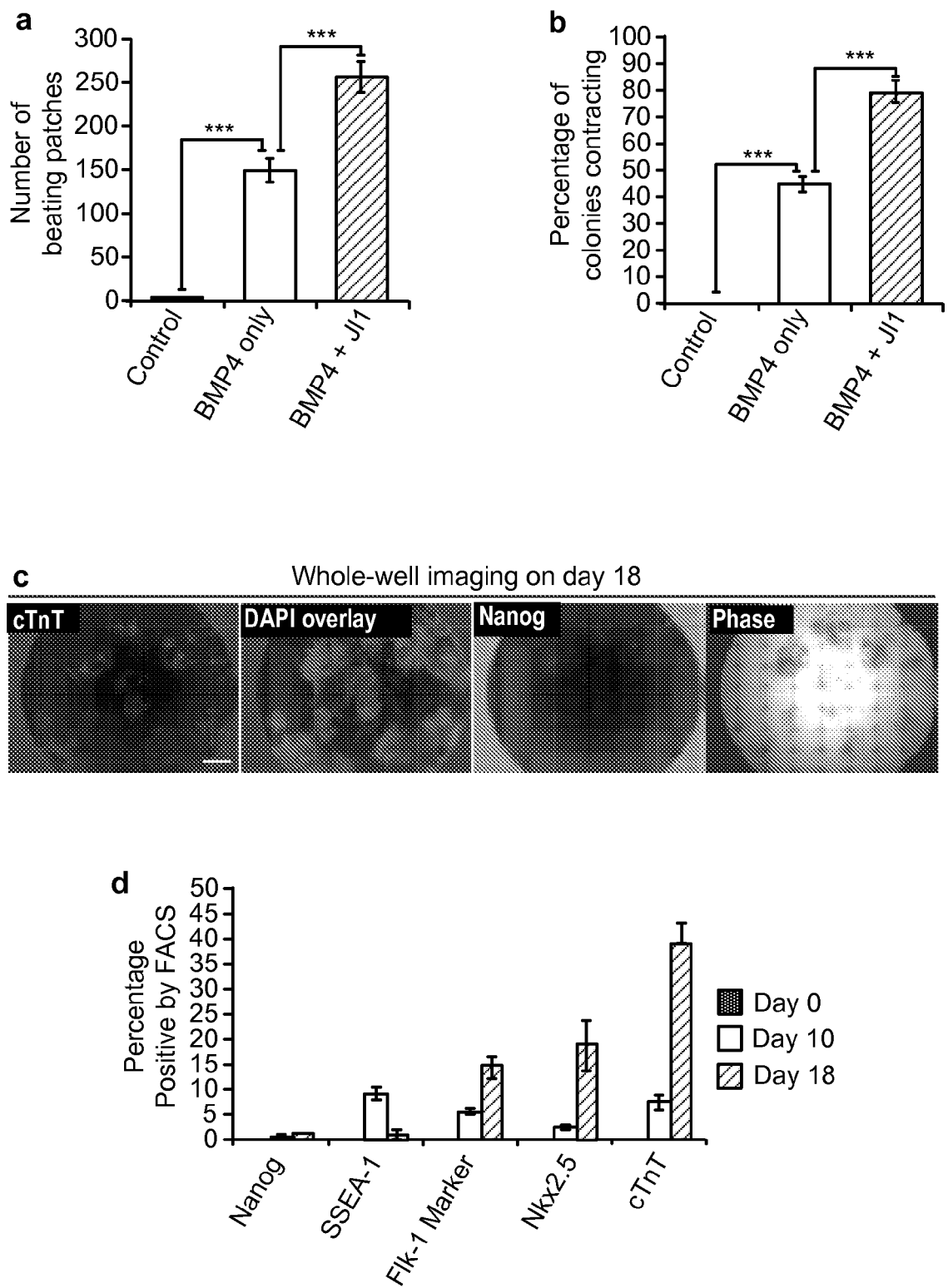
FIG. 2: Gauging reprogramming efficiency and success by incidence of beating and marker expression. (A, B) Changes in contracting colony number and percentage, respectively, upon culture treatment with BMP4 alone or in combination with the JAK inhibitor JI1. (C) Whole-well imaging (96-well plate format) depicting the relative expression of cTnT and Nanog on day 18. (D) FACS counts of cells positive for the indicated markers at three different timepoints. Scale bar in (C) is 900 µm.

The earliest wave-like spontaneous contractions also began on day 11, and many colonies were seen forcefully contracting in their entirety by day 15. Although not absolutely required, BMP4 appears to be the major driving force behind the robust development of beating: on average, its addition increased the formation of contracting patches nearly 150-fold (149±13 patches per 100,000 MEFs plated, n=6). Strikingly, sequential application of the JAK inhibitor JI1 and BMP4 can even further increase the number of contracting patches: we have obtained as many as 317 independently contracting patches per 100,000 MEFs plated by day 21 (mean=257±17, n=6; FIG. 2a). Under these conditions, the incidence of beating in terms of total colony number could be as high as 90% (mean=79±4%, n=5; FIG. 2b). The dramatic nature of this shift and the pervasiveness of the cardiogenic outcome were especially evident in whole-well microscopic analyses, in which all large colonies in a well could be seen expressing high levels of cTnT and spontaneously contracting by day 18. Conversely, they did not express above-background levels of Nanog-GFP at the same time point (FIG. 2c).

JI1 was most effective when applied continuously for the first nine days—the period during which there might be a remote possibility of generating iPSC intermediates due to the use of Yamanaka factors (FIG. 1b). Accordingly, its effectiveness declines with shorter treatment periods; however, extending JI1 treatment beyond nine days to overlap with CDM and BMP4 application also appears to be counterproductive (data not shown). This latter observation is supported by a recently reported requirement for JAK-STAT signalling in cardiomyogenesis (Snyder, M. et al., *J Biol Chem* 285, 23639-46 (2010)). In the case of BMP4, five days of treatment was optimal (FIG. 1b); both shorter and longer periods of treatment proved detrimental to the development of beating cardiac colonies (data not shown). While its precise role in direct cardiac differentiation remains to be clarified, BMP4 is most likely driving cardiac induction from nascent precursors during a critical developmental window (Cohen, E. D. et al., *Development* 135, 789-98 (2008); Klaus, A. and Birchmeier, W., *Pediatr Cardiol* 30, 609-16 (2009)). It could further be speculated that the cardioinductive effect of JI1 treatment might result from an indirect expansion of this precursor pool: by preventing cells from becoming primed for induced pluripotency, a larger number may ultimately become available for BMP4 to act upon and prime for cardiogenesis instead.

Transdifferentiation Yields a Substantial Number of Highly Differentiated and Functionally Responsive Cardiomyocytes Although contracting colony number serves as a very convenient metric for inter-sample comparisons of reprogramming success and efficiency, it does not allow for a quantification of the individual cardiomyocyte yield. To this end, we utilized fluorescence-activated cell sorting (FACS) on days 0, 10, and 18, examining both precursor (Isl1$^+$, Nkx2.5$^+$) and more mature (cTnT$^+$) cardiac populations. A modest increase was observed for all three markers by day 10, with significant increases by day 18. Isl1$^+$ and Nkx2.5$^+$ cells did not increase to the same extent as cTnT$^+$ cells, presumably because the former are more strongly expressed during the earlier stages of cardiac development (Qyang, Y. et al., *Cell Stem Cell* 1, 165-79 (2007)). Remarkably, nearly 40% (39±2%, n=5) of cells had become cTnT$^+$ at the later time point (FIG. 2d). Based on these data, the final yield of cTroponin T$^+$ cells was conservatively estimated to be 120,000 per 100,000 MEFs plated or 1.2 cardiomyocytes per fibroblast (100,000 starting MEFs reproducibly translated into a day 18 harvest of approximately 300,000-350,000 total cells).

Figure 3:
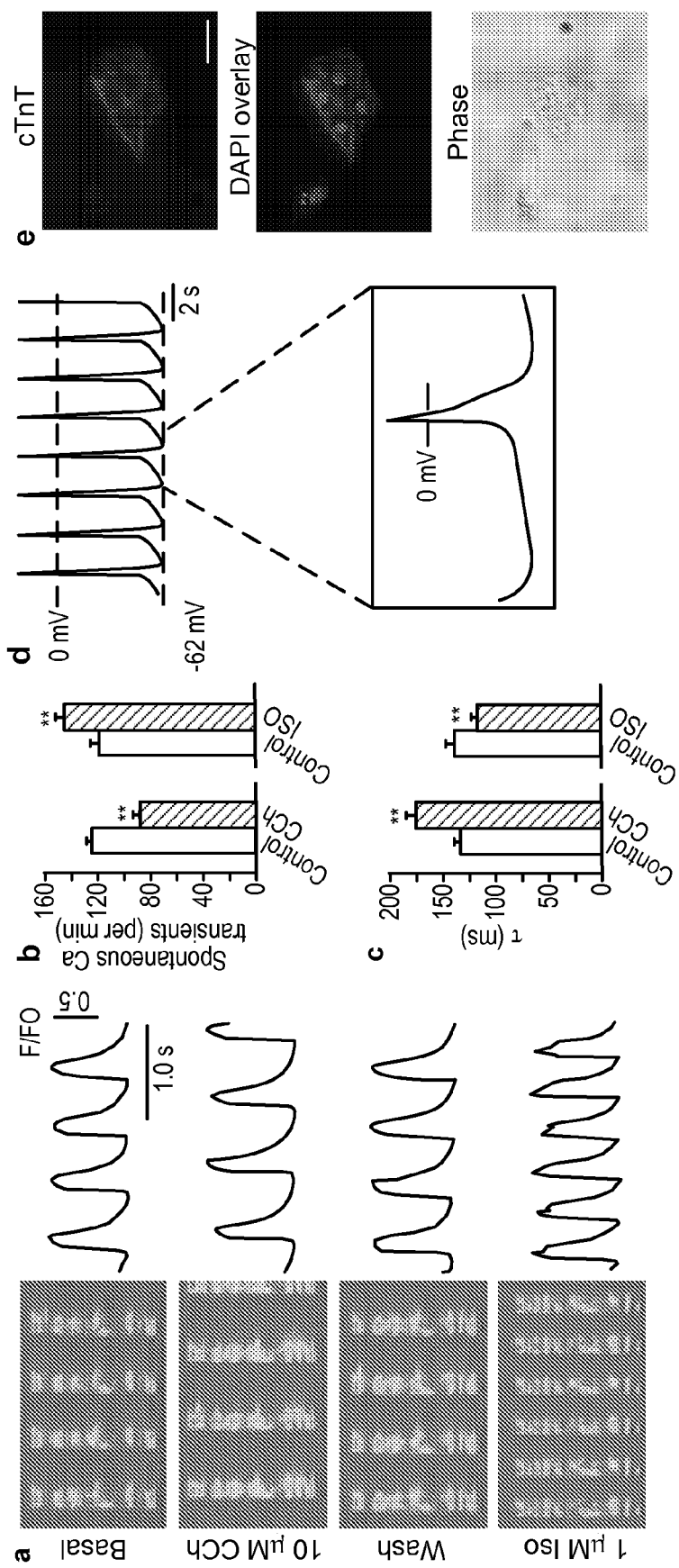
FIG. 3: Calcium flux and electrophysiological characterization of contracting cardiomyocytes. (A) Calcium transients recorded in spontaneously contracting colonies, before and after isoproterenol (Iso) and carbachol (CCh) treatment at the indicated concentrations. Quantification of the effect of treatment on transient frequency (B) and decay rate (C). (D) Spontaneous action potentials recorded from an individual cardiomyocyte at 20-22° C. The waveform of a single action potential is shown in the lower inset using an expanded time scale. Dashed lines indicate resting potential (−62 mV) and 0 mV, respectively. Colony numbers in a and b correspond to incidence per 100,000 MEFs plated and were recorded on day 18; error bars indicate s.e.m, n=6. The demarcations  and * indicate p values of >0.01 and >0.001, respectively. (E) Immunostaining of individually contracting cells isolated from a large colony arising from fibroblasts treated with cardiac reprogramming conditions.

To more closely examine the degree of differentiation among the population of contracting cells, we examined their beating frequency, calcium flux patterns, and response to chronotropic agents. Contraction frequency of cardiomyocytes on day 18 varied from a minimum of 4 beats per minute (BPMs) (data not shown) to a maximum of 130 BPMs. While this pattern implied a wide range of development/differentiation, the latter observation suggested that at least a subset of cardiomyocytes were acquiring highly differentiated traits (Kuzmenkin, A. et al., *FASEB J* 23, 4168-80 (2009)). Accordingly, many contracting patches exhibited characteristic calcium transients (Ieda, M. et al., *Cell* 142, 375-86 (2010); Shah, A. P. et al., *Cardiovasc Res* 87, 683-93 (2010)) (FIG. 3a) (Stieber, J. et al., *Proc Natl Acad Sci USA* 100, 15235-40 (2003)), the frequency of which could be reversibly modulated with 1 μM isoproterenol or 10 μM carbachol, indicating proper responsiveness to β-adrenergic and muscarinic signalling, respectively (Kuzmenkin, A. et al., *FASEB J* 23, 4168-80 (2009)) (FIG. 3b). Addition of isoproterenol significantly increased the frequency of spontaneous calcium transients and shortened the decay period (τ), while carbachol had the opposite effects (FIG. 3c). Total contracting colony number consistently levelled off beyond day 18, but most colonies continued to contract well beyond the end point of our assays (day 21), with some patches still contracting after five weeks (data not shown).

Next, we enzymatically dissociated contracting patches into individual cardiomyocytes and carried out electrophysiological measurements (FIG. 3d). The spontaneous action potentials (APs) generated in these cells closely resembled "atrial-like" (and to a lesser extent "pacemaker-like") APs reported elsewhere (Stieber, J. et al., *Proc Natl Acad Sci USA* 100, 15235-40 (2003)), with a mean diastolic potential (MDP) of −61.0±1.2 mV and a mean overshoot of 13.9±4.9 mV (n=3). As such, these data corroborate immunocytochemistry results suggesting a mostly atrial phenotype for the cardiomyocytes being generated (FIG. 1d).

Of note, we have repeatedly observed a small number of contracting single cells exhibiting characteristic cardiac troponin T staining even prior to enzymatic dissociation, indicating that nascent cardiomyocytes can differentiate, and perhaps even arise, outside of the context or "niche" of a developing colony (FIG. 1e). Such a phenomenon would suggest that a subset of cells might be taking a more direct transdifferentiation path (i.e., perhaps not having to rely on extracellular cues from neighbouring cells in colony), a hypothesis consistent with the stochastic nature of Yamanaka factor-induced reprogramming.

Figure 4:
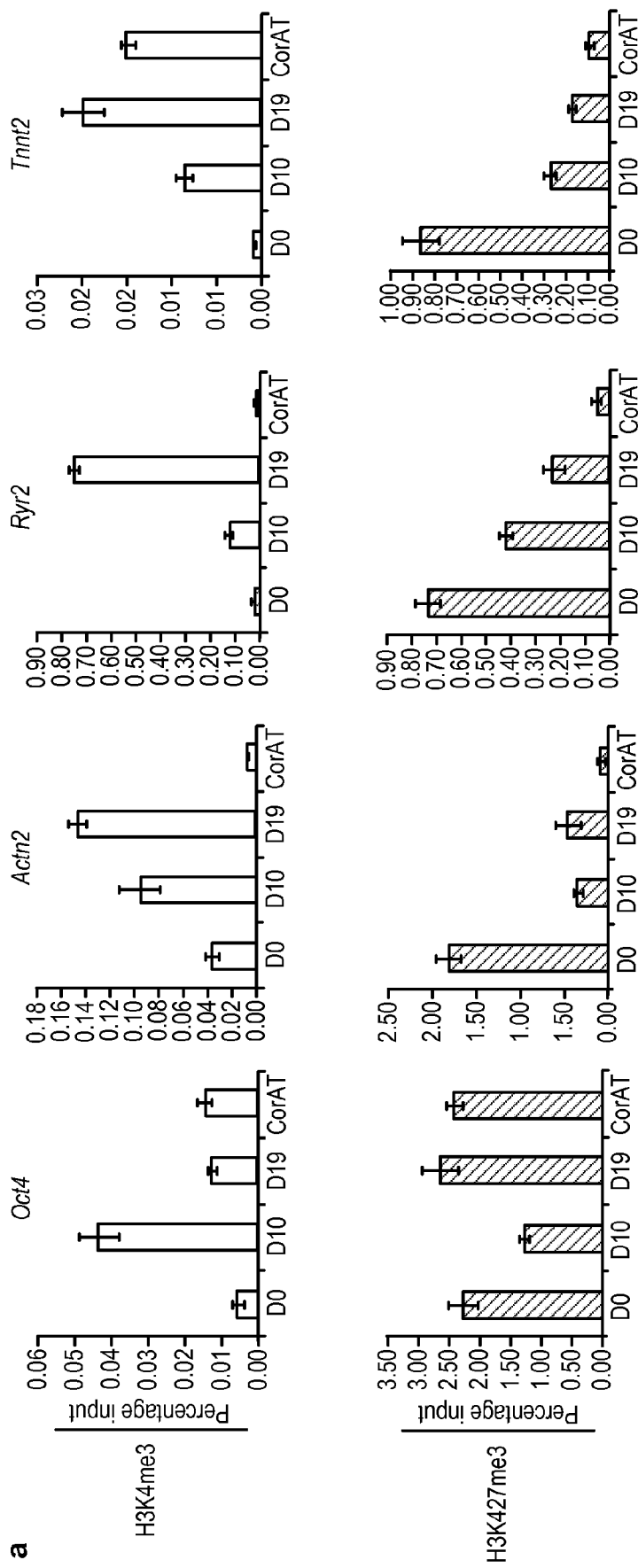
FIG. 4: Development of pluripotency is detrimental to cardiogenesis. (A) ChIP assays examining epigenetic modifications at four relevant loci during reprogramming, as indicated by changes in K4 and K27 trimethylation levels of histone H3. CorAT denotes commercially available pure cardiomyocytes. (B) Effect of conditions promoting iPSC generation on cardiac reprogramming. Schematic depiction of modifications to conditions (left) with corresponding relative efficiencies (right). (C) Testing of our protocol (and portions thereof, indicated by grey arrows) on mESCs to ascertain potential cardiogenic effects on pluripotent cells. (D) Differential effects of prolonged transgene expression on beating vs. total colony number.
Figure 4:
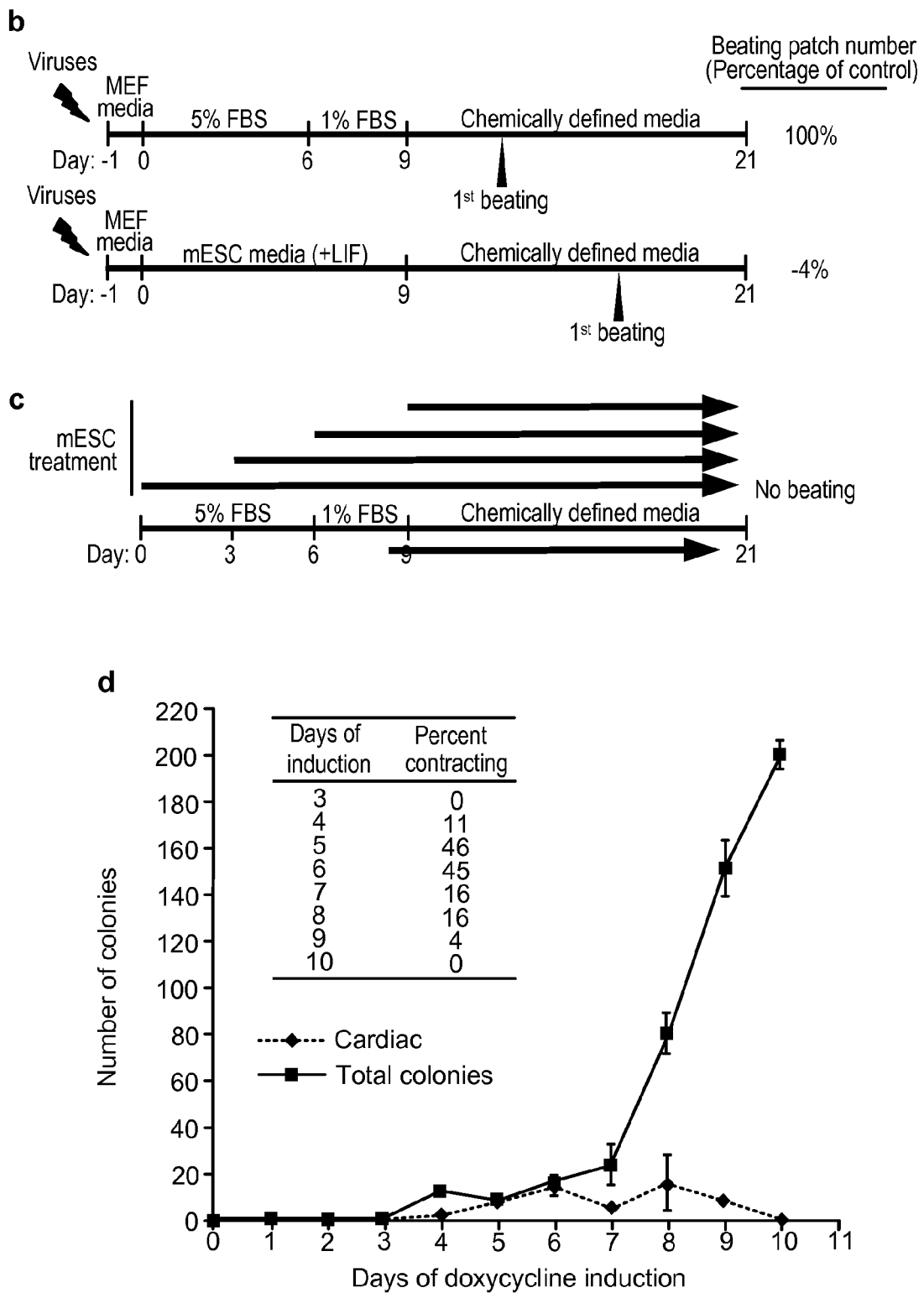

Next, we conducted chromatin immunoprecipitation (ChIP) assays to ascertain the nature and extent of certain epigenetic changes taking place at four loci: Oct4, Actn2 (encoding α-actinin), Ryr2 (encoding the cardiac ryanodine receptor), and Tnnt2 (encoding cardiac Troponin T). Relative levels of trimethylation at histone H3 lysine 4 (H3K4me3) and lysine 27 (H3K27me3) in the promoter regions of these genes were examined. As expected, due to strong exogenous expression of the Yamanaka factors during the initial part of the protocol, we observed an initial burst of activating H3K4me3 (with a concomitant decrease in H3K27 m3) at the Oct4 promoter by day 10, followed by a return to the H3K27me3-dominated, repressed state seen in the starting MEFs by day 19 (FIG. 4a). The promoters of the three cardiac genes, all of which are expressed at the later stages of cardiomyogenesis, also exhibited enrichment in H3K4me3 by day 10, but unlike Oct4, this trend did not stop or reverse; by day 19, H3K4me3 enrichment was extensive compared to the starting MEFs. Strikingly, it even exceeded levels found in cardiomyocytes derived from mESCs (FIG. 4a). Concurrently, levels of repressive H3K27me3 at the cardiac loci had fallen far below the starting fibroblasts' levels, and were approaching those of the control cardiomyocytes.

Transdifferentiated Cardiomyocytes Most Likely do not Arise from Contaminating Cardiac Precursors or iPSC Intermediates To rule out the possibility that beating patches might be arising from rare multipotent cardiac precursor cells in our MEF cultures, we tested our method on tail-tip fibroblasts (TTFs), a much more homogenous source of fibroblasts that does not contain any cardiac cells. As postnatal and adult cells are more refractory to reprogramming (Markoulaki, S. et al., *Nat Biotechnol* 27, 169-71 (2009)), it was necessary to use all four reprogramming factors, including c-Myc, to induce cardiac colony formation. Surprisingly, on day 12—only a day later than when MEFs were used—we observed a small number of colonies beginning to contract. Despite this striking similarity in timing, the number of beating patches generated per 100,000 cells plated (115±7, n=6) was lower than the yield from MEFs reprogrammed under the same conditions (145±6, n=6; p<0.01).

The conditions utilized in our protocol are not conducive to the establishment or maintenance of iPSCs (Blelloch, R. et al., M., *Cell Stem Cell* 1, 245-7 (2007)). We do not utilize feeder cells or LIF, and switch to chemically defined media containing cardiogenic molecules early in the protocol. Most importantly, even with three-factor transduction, the first contracting patches emerge within 12 days, a much shorter period than the approximately three-week minimum required to generate iPSCs with three factors (Nakagawa, M. et al., *Nat Biotechnol* 26, 101-6 (2008); Wernig, M. et al., *Cell Stem Cell* 2, 10-2 (2008)). Strikingly, cardiac reprogramming of TTFs also proceeds at the same pace, even though such postnatally derived cells would normally be expected to reprogram more slowly (Okada, M. et al., *Biochim Biophys Acta* 1800, 956-63 (2010)). Despite these considerations, we sought to more rigorously rule out the possibility that our method might depend on the generation of a transient pluripotent intermediate, the re-differentiation of which could conceivably give rise to cardiomyocytes.

First, we reasoned that if generation of iPSCs prior to the switch to CDM were critical, using standard reprogramming media with LIF for the first nine days should yield a greater number of contracting colonies. However, this substitution actually resulted in a four-day delay in the onset of beating and a ~25-fold decline in beating colony number (FIG. 4b). A critical implication of this result is that early reprogramming events—brought about primarily by the overexpression of the Yamanaka factors—appear to be generating a heterogeneous population of cells with diverse developmental potential, as even standard reprogramming media allows for the generation of a very small number of cardiac progenitors. Further, conditions that favour the development of iPSCs must do so at the expense of other potential outcomes of the reprogramming process: although marginally permissive, standard reprogramming media is a very poor choice for the initiation of direct cardiac reprogramming.

Prolonged Induction of the Pluripotency Program Inhibits Transdifferentiation

Second, the rapid induction of beating suggests that lineage commitment decisions are made quite early. We speculate that the reprogramming factors (especially Oct4) mostly function to "erase" cell identity by epigenetic mechanisms, and do not directly activate lineage-specific genes. Conversely, exposure to external, cardiac-specific signals (in this case BMP4 treatment) likely has role(s) in early lineage specification and/or the induction of terminal differentiation. In any case, overexpression of reprogramming factors should be only transiently required to allow for activation of lineage-specific gene networks, with prolonged expression likely to be detrimental. To test this hypothesis, we generated secondary MEFs harbouring doxycycline-inducible transgenes (Wernig, M. et al., Nat Biotechnol 26, 916-24 (2008)) and a Nanog-GFP reporter (Hanna, J. et al., Cell 133, 250-64 (2008)) to monitor establishment of pluripotency (Silva, J. et al., Cell 138, 722-37 (2009)). Strikingly, a mere four days of doxycycline treatment was sufficient to induce beating on day 11. The optimal duration of drug treatment was between five and six days, with treatment longer than nine days not producing any contracting cardiac cells at all (FIG. 4d). Conversely, generation of iPSC colonies using this particular system requires a minimum of 12 days of transgene induction (Wernig, M. et al., Nat Biotechnol 26, 916-24 (2008); Brambrink, T. et al., Cell Stem Cell 2, 151-9 (2008)). Even the shortest transgene expression requirement reported to date is seven to eight days (Stadtfeld, M. et al., Nat Methods 7, 53-5 (2010)). In short, optimal cardiac reprogramming requires transgenes to be inactivated well before pluripotency can be endogenously established.

We also tested our protocol on mESCs to establish whether it had a cardiogenic effect on pluripotent cells. Substituting mESCs for day 0, 3, 6, or 9 cultures in our protocol did not produce any contracting patches by day 21 or beyond, indicating that our protocol could not bring about the development of cardiac colonies from iPSCs, even if they were arising during the direct reprogramming process (FIG. 4c). In summary, these results demonstrate the establishment of bona fide pluripotency during our protocol would in fact constitute a strong barrier to successful cardiac reprogramming.

Figure 5:
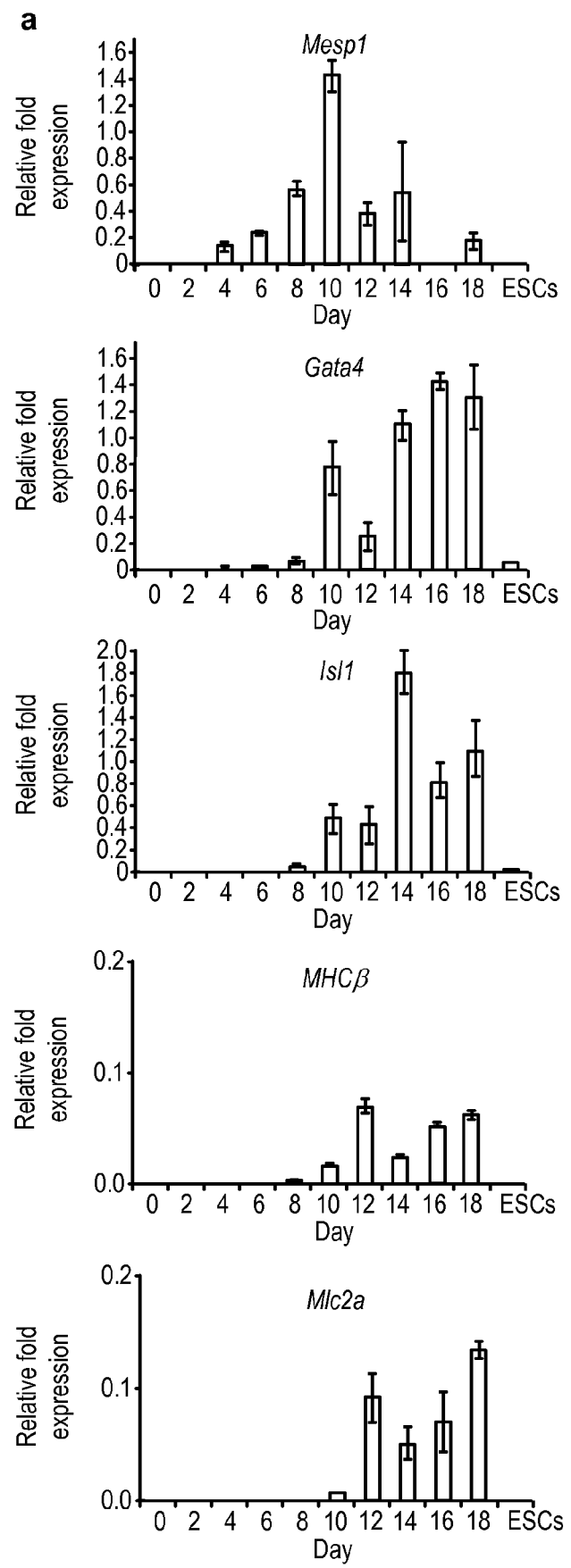
FIG. 5: Direct cardiac reprogramming represents a parallel process that occurs in the absence of iPSC generation. Time course analysis of cardiac lineage (A) and pluripotency (B) marker expression by quantitative RT-PCR. (C) Phase-contrast and FITC-channel images depicting cardiac colony formation and maturation in Nanog-GFP reporter MEFs. Spontaneous contraction was first detected on day 12 in the encircled portion of the colony. Robust early activation of the Nanog-GFP marker using standard reprogramming methods is provided as a positive control. Error bars in (A) and (B) indicate standard deviation, n=3. Scale bars in (C) are 100 μm.
Figure 5:
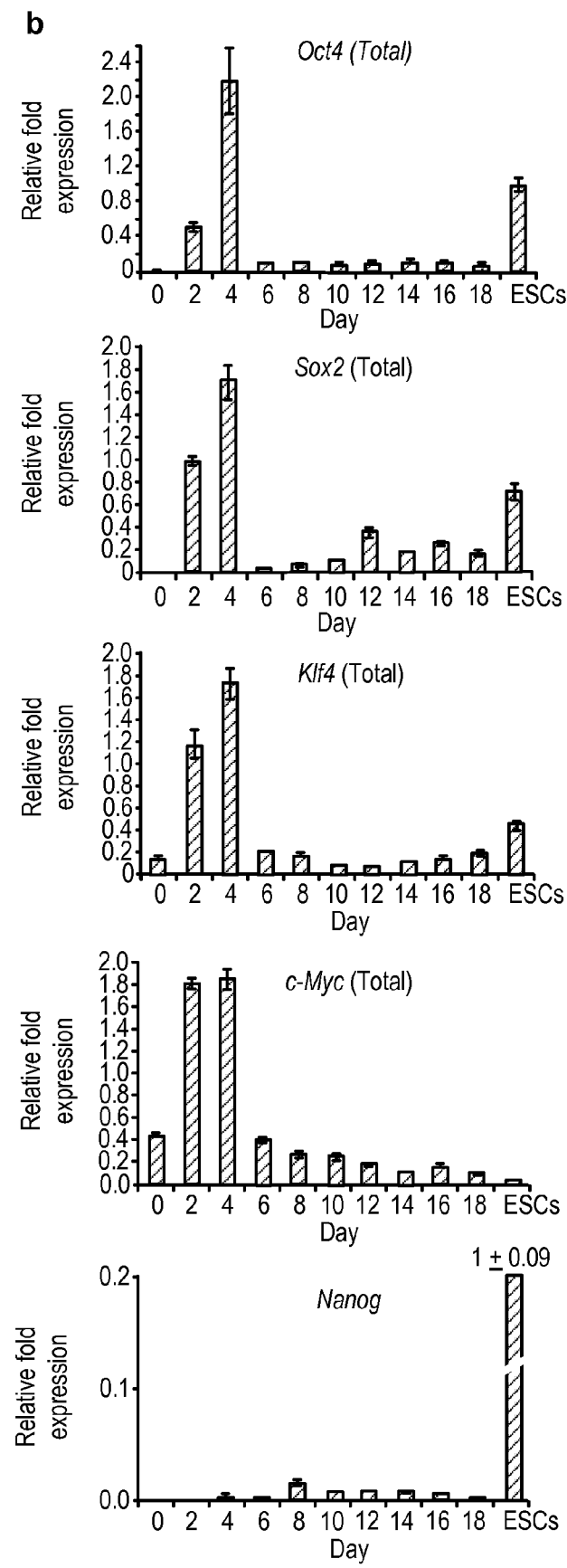
Figure 5:
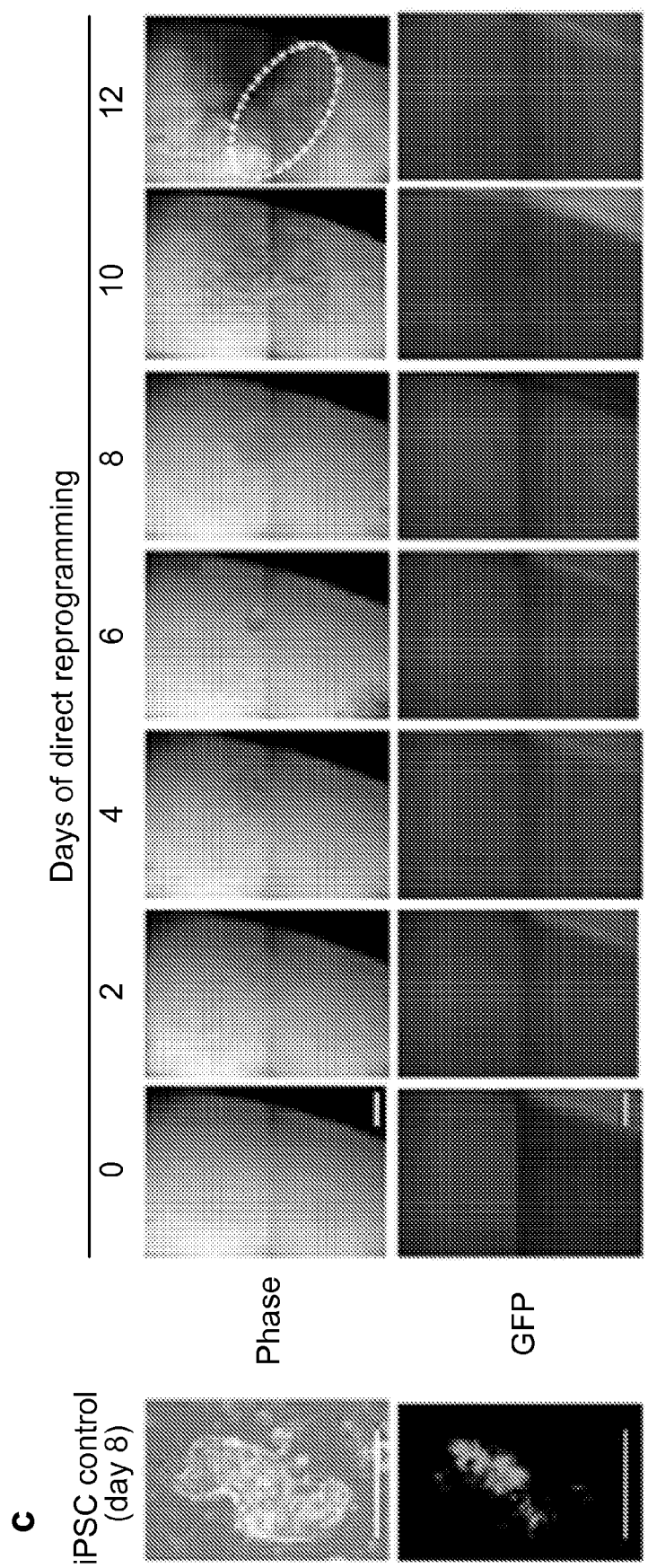

Cardiac Transdifferentiation and iPSC Generation Represent Parallel, Non-overlapping Processes Third, quantitative RT-PCR results show that the cardiogenic program is already underway by days 4-6, as indicated by the robust expression of Mesp1 and GATA4 transcripts (FIG. 5a). We did note that the randomness and asynchrony inherent in reprogramming perhaps resulted in a heterogeneous population of cardiac mesoderm cells and, in turn, higher inter-sample variation. Conversely, levels of reprogramming factor transcripts decrease precipitously following doxycycline withdrawal and generally remain very low. Endogenous Nanog transcripts are not detectable until days 8-9, and at very low levels (FIG. 5b). Consequently, most colonies do not express any Nanog-GFP at all; only a small subset show levels of fluorescence scarcely above background, starting on days 9-12 (data not shown). Thus, any low-level activation of Nanog coincides with early expression of mature cardiac markers such as the βisoform of myosin heavy chain (MHCβ) and the initiation of spontaneous contraction on day 11 (FIG. 5a). Although this concurrent activation of late-stage iPSC and cardiomyocyte markers effectively rules out the possibility that the former could somehow give rise to the latter, we sought to definitively show that the development of spontaneous contraction does not require activation of the endogenous pluripotency network. To accomplish this, we took daily photographs of large numbers of cells undergoing direct reprogramming and retrospectively evaluated Nanog-GFP expression in colonies that eventually began contracting. Not surprisingly, we found that these colonies had not expressed even minute amounts of Nanog-GFP at any time during their formation or differentiation (FIG. 5c).

FACS analyses of SSEA-1$^+$ and Nanog$^+$ cells on days 0, 10, and 18 corroborated the above results: even on day 18, Nanog$^+$ cells only comprised 1% of the population. SSEA-1$^+$ cells made up a similarly small fraction of the cells on day 18. On day 10, these latter cells represented close to 10% of the population (FIG. 2d). However, since SSEA-1 is one of the earliest markers induced upon Yamanaka factor overexpression (Stadtfeld, M. et al., Cell Stem Cell 2, 230-40 (2008))— and is in fact expressed in a range of differentiated precursor cells (Anjos-Afonso, F. and Bonnet, D., Blood 109, 1298-306 (2007); Koso, H. et al., Dev Biol 292, 265-76 (2006))—it is not a marker of bona fide pluripotency. This notion is especially valid given the lack of concomitant Nanog expression (Silva, J. et al., Cell 138, 722-37 (2009)) and the precipitous decline of the SSEA-1$^+$ population by day 18. We surmise that the higher levels on day 10 may result from a delayed downregulation of exogenously induced SSEA-1 following dox withdrawal.

Taken together, these results indicate that any iPSC-like cells generated in our protocol are a minor by-product and most likely do not contribute to cardiomyocyte formation. The observation that JAK-STAT pathway inhibition by JI1 can shift the balance considerably in favour of cardiomyogenesis constitutes strong evidence that the relationship between iPSC and cardiomyocyte formation is zero-sum in nature, i.e., that they represent mutually exclusive outcomes.

Discussion

We have shown that brief reactivation of reprogramming factors in embryonic and adult fibroblasts can be used to rapidly generate contracting cardiomyocytes—almost certainly without going through a pluripotent intermediate. Compared to transdifferentiation by lineage-specific factor overexpression, our protocol is nearly three times as fast: the first spontaneous contractions begin after 11 days vs. 4-5 weeks (Ieda, M. et al., Cell 142, 375-86 (2010)). Moreover, the efficiency in terms of cTnT$^+$ cardiomyocyte yield is several fold higher: we have obtained approximately 1.2 cTnT$^+$ cells for each fibroblast plated (vs. an estimated maximum of 0.2) (Ieda, M. et al., Cell 142, 375-86 (2010)). This latter feat is most likely made possible by the generation of mitotically active precursor cells akin to multipotent/s/1$^+$ cardiovascular progenitors (MICPs) (Qyang, Y. et al., Cell Stem Cell 1, 165-79 (2007)), as suggested by gene expression data. It is tempting to speculate that these intermediate cells, if successfully isolated and stabilized in culture, could eventually become an expandable and renewable source for not just cardiomyocytes, but many other terminally differentiated cardiovascular cells as well.

Figure 6:
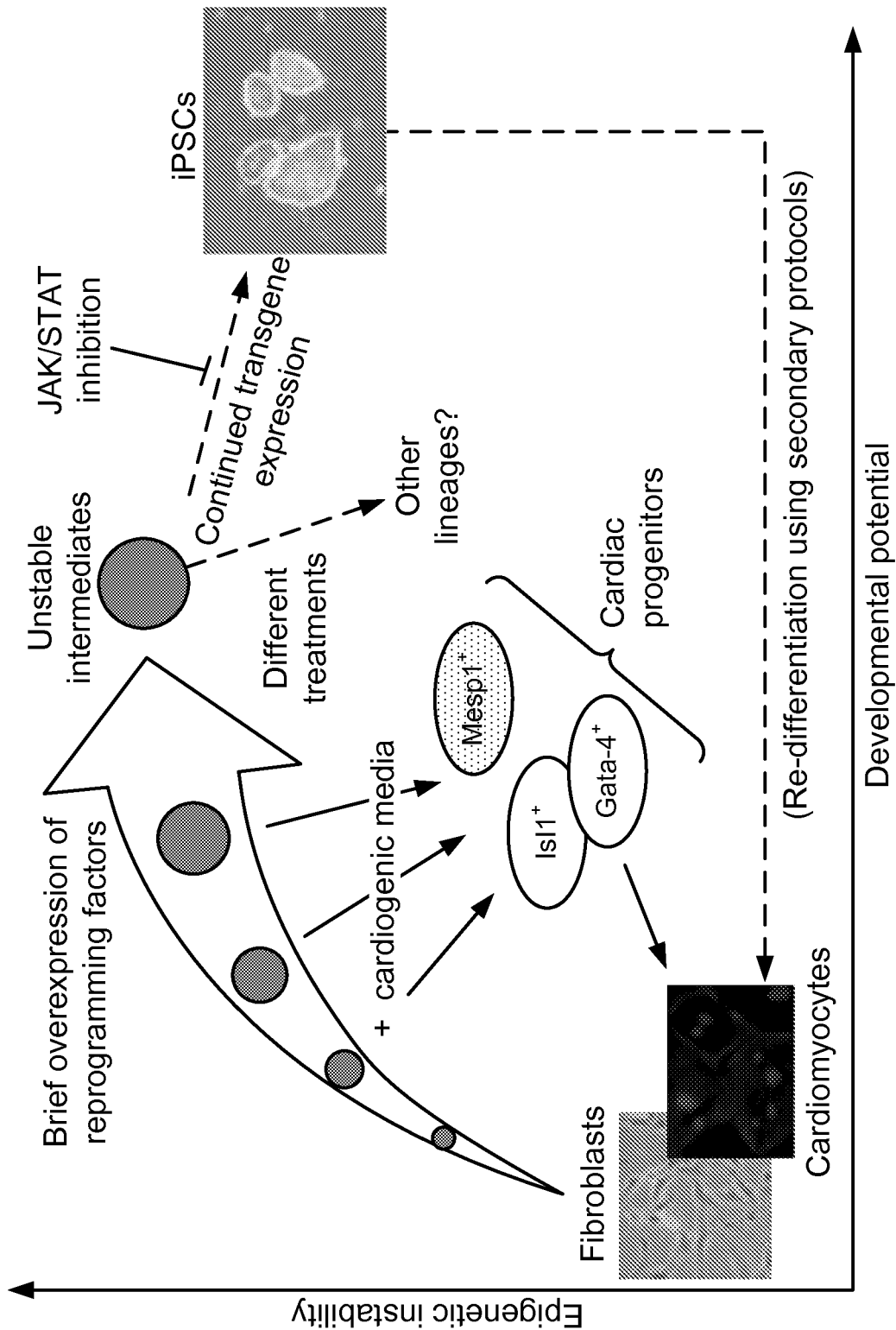
FIG. 6: A model for direct reprogramming to alternative fates. A brief burst of reprogramming factor overexpression leads to the formation of various highly transient and epigenetically unstable (i.e., less restricted, more naïve) intermediates. These cells then spontaneously "relax" back into more stable state(s). Due to the very complex nature of complete dedifferentiation, the generation of iPSCs is not a likely outcome of this process, and requires continued overexpression of exogenous pluripotency factors. Conversely, a direct switch to multipotent lineage progenitors—or even terminally differentiated cells—represents the path of least resistance, especially under culture conditions that (a) allow and/or promote their genesis and proliferation and (b) simultaneously inhibit establishment of pluripotency (JAK/STAT inhibition).

The process we have discovered bears a striking resemblance to regeneration blastema formation in zebrafish and frogs, during which the stage is set for transdifferentiation by transient low-level expression of pluripotency factors (esp. Oct4 and Sox2) rather than a re-establishment of pluripotency (Christen, B. et al., BMC Biol 8, 5 (2010)). While this suggests that the two processes could share a common mechanism, confirmation of this hypothesis will require a more detailed understanding of the molecular underpinnings of reprogramming and its various intermediate stages (Stadtfeld, M. et al., *Cell Stem Cell* 2, 230-40 (2008)). The key role here for reprogramming factors is likely the induction of a developmentally more naïve, open-chromatin state marked by high epigenetic instability (Meshorer, E. et al., *Dev Cell* 10, 105-16 (2006); Hochedlinger, K. and Plath, K., *Development* 136, 509-23 (2009); Artyomov, M. N. et al., *PLoS Comput Biol* 6, e1000785). Highly unstable intermediate populations may give rise to a multitude of cell types as they rapidly "relax" back into epigenetically more stable states, among which pluripotency is one of many possible outcomes (FIG. 6). This model underscores the unique versatility and potential of our transdifferentiation scheme as compared to lineage-specific transcription factor ovexpression, namely the likelihood that precursors and/or fully differentiated cell types from many different lineages could be derived simply by using different inductive signals. Thus, for the generation of autologous tissue, transdifferentiation offers a potentially very attractive alternative to the rather circuitous iPSC methodology.

Material and Methods

Cell culture and media: All MEFs (129S2/SvPasCrlf) were derived according to WiCell protocols (https://www.wicell.org/index.php?option=com_docman&task=doc_download&gid=687). TTFs were a kind gift of Dr. Hans Schöler. Secondary MEFs were derived as previously described (Wernig, M. et al., *Nat Biotechnol* 26, 916-24 (2008)). All results were initially obtained and confirmed with the Nebulette-LacZ MEFs; to ensure reproducibility and minimize inter-experimental variation, reported results almost exclusively derive from experiments utilizing secondary dox-inducible MEFs using the optimum induction period. MEFs were initially passaged on gelatin-coated (0.1% for 2 hours at 37° C.) tissue culture dishes in DMEM supplemented with 10% FBS, 2 mM Glutamax and 0.1 mM NEAA (all components from Invitrogen, Carlsbad, Calif.). Prior to viral transduction, cells were seeded onto Matrigel (BD Biosciences, Franklin Lakes, N.J.) or Geltrex (Invitrogen)-coated plates (1:40, overnight at 4° C.) at $3.5 \times 10^4$ cells per well of a six well plate ($7 \times 10^4$ cells for TTFs) in the same media. 12-24 hours after the addition of virus, cells were washed with PBS and switched to reprogramming media: knockout DMEM with 1-15% knockout serum replacement, 1-15% ES-qualified FBS, 1% Glutamax, 1% nonessential amino acids, 0.1 mM β-mercaptoethanol, and 1% ESC-qualified nucleosides (all components from Invitrogen except nucleosides, Millipore, Billerica, Mass.). When required for a control experiment, LIF (Millipore) was also added at $10^3$ units ml$^{-1}$. At the indicated times, cells were again washed with PBS and switched to CDM: RPMI-1640 supplemented with 0.5×N2, 1× B27 (without vitamin A), 0.05% BSA fraction V, 0.5% Glutamax, and 0.1 mM β-mercaptoethanol (all components from Invitrogen). BMP4 (Stemgent, San Diego, Calif.) and/or JI1 (EMD, San Diego, Calif.) were added at multiple timepoints for different durations. Fresh media was added at least once every 48 hours throughout all experiments. For the inducible reprogramming of secondary MEFs, 2 μg/ml dox was used, with the exception of four-day induction experiments, where the first two days of treatment were done at 4 μg/ml.

Retroviral packaging and transduction: Retroviruses encoding Oct4, Sox2, Klf4, and c-Myc were individually packaged in PLAT-E cells using pMXs-based vectors (Addgene, Cambridge, Mass.) and infections were carried out as previously described (Takahashi, K. et al., *Nat Protoc* 2, 3081-9 (2007)).

LacZ assays: Nebulette-LacZ expression was detected in situ using a beta-galactosidase staining kit (Stratagene, San Diego, Calif.).

Immunocytochemistry and fluorescence microscopy: Cells were fixed in 4% paraformaldehyde (Sigma-Aldrich, St. Louis, Mo.) for 15 minutes, washed three times with PBS (phosphate-buffered saline), and incubated in PBS containing 0.3% Triton X-100 (Sigma-Aldrich) and 5% donkey serum (Jackson ImmunoResearch, West Grove, Pa.) for 1 hour at room temperature. All primary antibody incubations were done overnight at 4° C.: cardiac troponin T (CT3, Developmental Studies Hybridoma Bank, Iowa City, Iowa; 1:1,000); Flk1 (AF-644, R&D Systems; Minneapolis, Minn.; 1:100); Gata4 (sc-25310, Santa Cruz Biotechnology, Santa Cruz, Calif.; 1:200); Myosin heavy chain (MF20, Developmental Studies Hybridoma Bank, 1:200); Nkx2.5 (sc-8697, Santa Cruz, 1:200); Mlc2v (aka My17; sc-34488, Santa Cruz, 1:50); Connexin-43 (610061, BD Biosciences, 1:100), and α-actinin (NBP1-40428, Novus, Littleton, Colo.; 1:100). Following three PBS washes, cells were incubated with the appropriate Alexa Fluor-conjugated secondary antibodies (Invitrogen) for 1 hour at room temperature and nuclei were stained with DAPI (Sigma-Aldrich). Images were captured using a Zeiss AX10 microscope equipped with an Axiocam HRm camera and processed using Axiovision 4.7.1 software. Colony tracking experiments and whole-well microscopic imaging were done on a Pathway 435 system (BD Biosciences).

Quantitative PCR: For each sample/timepoint, total RNA from two wells of a six-well plate was extracted using the RNeasy Plus Mini Kit with Qiashredder columns (Qiagen, Germany), after which 1 μg of RNA was reverse transcribed with the iScript cDNA Synthesis Kit (Bio-Rad, Hercules, Calif.). All quantitative PCR reactions were done in duplicate on a CFX96 system with iQ SYBR Green Supermix (Bio-Rad), using one twentieth of a cDNA reaction per replicate. Expression data were normalized relative to ribosomal protein L7 transcript levels. Each set of reactions was repeated using cDNA from at least three independent experiments. Primer sequences and details of amplification conditions are available upon request.

Chromatin immunoprecipitation quantitative PCR (ChIP-qPCR): ChIP was performed using a commercially available Magna ChIP G kit (Millipore). Briefly, histones and DNA were cross-linked by incubation in 1% formaldehyde. The chromatin was then sonicated to an average DNA fragment length of 200 to 500 bp. Equal amounts of soluble chromatin were incubated with and without anti-normal rabbit IgG, anti-trimethyl-histone H3 lysine 4 (#17-614, Millipore; 3 ul/reaction) or anti-trimethyl-histone H3 lysine 27 (#17-622, Millipore; 4 ug/reaction) that had been pre-incubated with secondary antibodies conjugated to magnetic beads. After overnight antibody incubations, DNA-histone cross-linking was reversed and DNA fragments were purified. DNA fragments obtained without antibody were used as the input controls, whereas DNA fragments obtained with normal rabbit IgG were applied as negative controls. One microliter of the resulting DNA solution from each condition was subject to real-time PCR reaction. Error bars represent standard deviation. Primer sequences used are available upon request.

Flow cytometry: Adherent cells on plates were washed with PBS and dissociated with trypsin (Invitrogen), Accutase (Innovative Cell Technologies, San Diego, Calif.), or collagenase II (Invitrogen) for 10-45 minutes at 37° C. Cells were washed twice with ice-cold staining buffer (HBSS [Invitrogen] with 10 mM HEPES [Sigma], 2% FBS [Invitrogen], and 0.1% azide [Sigma]) and put through single-cell strainers (BD Biosciences) both times. Incubation with antibodies was done at 4° C. for 30 minutes at the volume and concentrations suggested by the manufacturer. Cells were washed three times with staining buffer and fixed in high-grade 4% paraformaldehyde (Electron Microscopy Sciences, Hatfield, Pa.) for 15 minutes at 4° C. Cells were washed again with staining buffer and counted using a FACSCalibur flow cytometer and CellQuest software (BD Biosciences). Final analysis was later done with FlowJo software (Tree Star, Ashland, Oreg.). Antibodies used were as follows: APC-conjugated anti-Flk1 (560070, BD Biosciences), PE-conjugated anti-SSEA1 (560142, BD Biosciences), Alexa647-conjugated anti-Nanog (560279, BD Biosciences), anti-cTnT (ab10214, Abcam, Cambridge, Mass.), and anti-Nkx2.5 (sc-8697x, Santa Cruz). Unlabelled antibodies were conjugated to PE or APC using the appropriate LYNX rapid conjugation kit (AbD Serotec, Germany). All experiments included the appropriate isotype controls, conjugated using the same kits as above when necessary.

Calcium imaging and testing of chronotropic agents: Cells were loaded with Fluo-4-AM (5 µM, 30 min, 37° C.) (F14201, Invitrogen), and imaged with an Olympus Fluoview 1000 inverted confocal microscope with a 40× oil immersion lens (numerical aperture 1.3). Line scan imaging mode was used to measure spontaneous $Ca2^+$ transients at 37° C. Image processing and data analysis were performed as previously described (Ouyang, K. et al., J Biol Chem 280, 15898-902 (2005)). For drug testing, all measurements were repeated 10 minutes after the addition of isoproterenol (1 µM; Sigma) or Carbachol (10 µM; Sigma-Aldrich).

Electrophysiology: Contracting cell clusters were dissociated at 37° C. for 30-45 minutes using 1 mg/ml Collagenase type II in RPMI-1640 media supplemented with 10 mM HEPES and 5 mM sodium pyruvate (all reagents from Invitrogen). Following repeated pipetting to ensure complete dissociation, cells were allowed to adhere to fibronectin-coated Biocoat coverslips (BD Biosciences) overnight in Cor.At media (Lonza, Germany). Single-cell patch clamp recordings were performed using an Axopatch 200B amplifier and pClamp 10.0 software (HEKA Elektronik, Germany), as described previously (Ouyang, K. et al., J Biol Chem 280, 15898-902 (2005)). Spontaneous action potentials were recorded under whole-cell current-clamp conditions with a patch pipette resistance of 4-6 MΩ. Standard external solution contained (in mM): NaCl 150, KCl 5.0, CaCl2 2.0, MgCl 2 1.0, HEPES 10, and glucose 10 (pH 7.4 adjusted with NaOH). Intracellular pipette solution contained (in mM): 150 KCl, 5.0 NaCl, 1.0 MgCl2, 2.0 EGTA, 1.0 MgATP, 10 HEPES (pH 7.2 adjusted with KOH). All experiments were performed at room temperature (20-22° C.).

Videos: All videos were recorded using a Canon A65015 digital camera custom-mounted to a Zeiss Axiovert 40C microscope.

Statistics: P values for the purpose of group comparisons were calculated using Student's t test. Differences where $p<0.05$ were regarded as significant.

Example 2

Direct Reprogramming of Neural Precursor Cells to a Cardiac Fate

Neural precursor cells (NPCs) transduced with four factors (Oct4, Sox2, Klf4, and c-Myc) can give rise to a small number of beating colonies within 18 days. On average, six beating colonies/50 k cells plated were obtained when they were switched directly into reprogramming media following viral transduction (i.e. without overnight incubation in NPC media). Keeping the cells in NPC media for the first 24 hours after transduction only resulted in half the number of colonies, and they beat more slowly. Interestingly, NPCs transduced with three factors only (Oct4, Sox2, and Klf4) gave rise to many pink colonies, presumably hematopoietic blood islands.

Example 3

Direct Reprogramming of Fibroblasts to a Neural Fate

The simple yet powerful technique of induced pluripotency may eventually supply a wide range of differentiated cells for cell therapy and drug development. However, making the appropriate cells via induced pluripotent stem cells (iPSCs) requires reprogramming of somatic cells and subsequent re-differentiation. Given how arduous and lengthy this process can be, we sought to determine whether it might be possible to convert somatic cells into lineage-specific stem/progenitor cells of another germ layer in one step, bypassing the intermediate pluripotent stage. Here we show that transient induction of the four reprogramming factors (Oct4, Sox2, Klf4, and c-Myc) can efficiently transdifferentiate fibroblasts into functional neural stem/progenitor cells (NPCs) with appropriate signalling inputs. Compared to "iN cells" (induced neuronal cells), transdifferentiated NPCs have the distinct advantage of being expandable in vitro and retaining the ability to give rise to multiple neuronal subtypes and glial cells. Our results provide a new paradigm for iPSCfactor-based reprogramming by demonstrating that it can be readily modified to serve as a platform for transdifferentiation.

Introduction

Although successful transdifferentiation from one cell type to another by overexpressing lineage-specific genes in vivo (Takeuchi, J. K. et al., Nature 459(7247):708-711 (2009), Zhou, Q. et al., Nature 455(7213):627-632 (2008)) and in vitro (Graf, T. et al., Nature 462(7273):587-594 (2009); Ieda M. et al., Cell 142(3):375-386 (2010)) has been reported, these methods are typically only effective when developmentally closely related cell types are used. While the generation of iN cells (Vierbuchen, T. et al., Nature 463(7284):1035-1041 (2010)) using neural-specific transcription factors has established that inter-lineage transdifferentiation is also possible in vitro, all transdifferentiation schemes to date entail overexpression of different sets of lineage-specific transcription factors. Intriguingly, a recent study reporting single-factor transdifferentiation of fibroblasts into blood precursors using OCT4 (Szabo, E. et al., Nature 468(7323):521-526 (2010)) is no exception: by virtue of its long-term ectopic expression and extensive binding to the regulatory regions of key hematopoietic genes, OCT4 also appears to be participating in regulating hematopoietic programs acting as a lineage-specific transcription factor in this context. The exceptional aspect of this study is rather the ability to generate a mitotically active progenitor population that can be further differentiated into a variety of blood cells a critical feat that has yet to be accomplished in transdifferentiation to cardiac and neural lineages.

In an effort to devise a more general transdifferentiation strategy that might give rise to a broad array of unrelated cell types—including lineage-specific precursors—we attempted to direct the conventional four iPSC-factor-based reprogramming (Takahashi, K., et al., Cell 126(4):663-676 (2006);

Takahashi K. et al., *Cell* 131(5):861-872 (2007)) toward alternative outcomes. Specifically, studies indicating that iPSCs are generated in a sequential and stochastic manner (Stadtfeld, M. et al., *Cell Stem Cell* 2(3):230-240 (2008); Brambrink, T. et al., *Cell Stem Cell* 2(2):151-159 (2008); Hanna J. et al., *Nature* (2009)) led us to hypothesize that we might be able to manipulate cells at an early and epigenetically highly unstable state induced by the reprogramming factors. Different conditions could potentially give rise to a multitude of cell types (Artyomov, M. N. et al., *PLoS Comput Biol* 6(5): e1000785 (2010)) with more stable epigenetic profiles. In this context, induced pluripotency is only one—and perhaps among the less likely—of many possible outcomes. Indeed, studies have found partially or incompletely reprogrammed cells expressing multiple lineage-specific markers (Takahashi, K., et al., *Cell* 126(4):663-676 (2006); Mikkelsen, T. S. et al., *Nature* 454(7200):49-55 (2008); Meissner, A. et al., *Nat Biotechnol* 25(10):1177-1181 (2007); Silva, J. et al., *PLoS Biol* 6(10):e253 (2008); Maherali, N. et al., *Cell Stem Cell* 1(1):55-70 (2007); Sridharan, R. et al., *Cell* 136(2):364-377 (2009)), although these cells did not appear to represent physiologically relevant cell types. Accordingly, we hypothesized that it might be possible to deliberately bias the early reprogramming process toward a defined precursor cell type by employing inductive and/or permissive signalling conditions, after which the desired cells could be selected and expanded.

In the present study, we have directly reprogrammed fibroblasts to functional neural stem/progenitor cells (NPCs) over an abbreviated period of four-factor induction. This direct reprogramming process is clearly distinct from conventional reprogramming to iPSCs or forward differentiation of pluripotent cells. Our findings not only represent the first successful transdifferentiation of somatic cells into proliferating NPCs, but also form the basis of a new methodology for inter-lineage transdifferentiation into multi- or oligopotent cells.

Results

Figure 7:
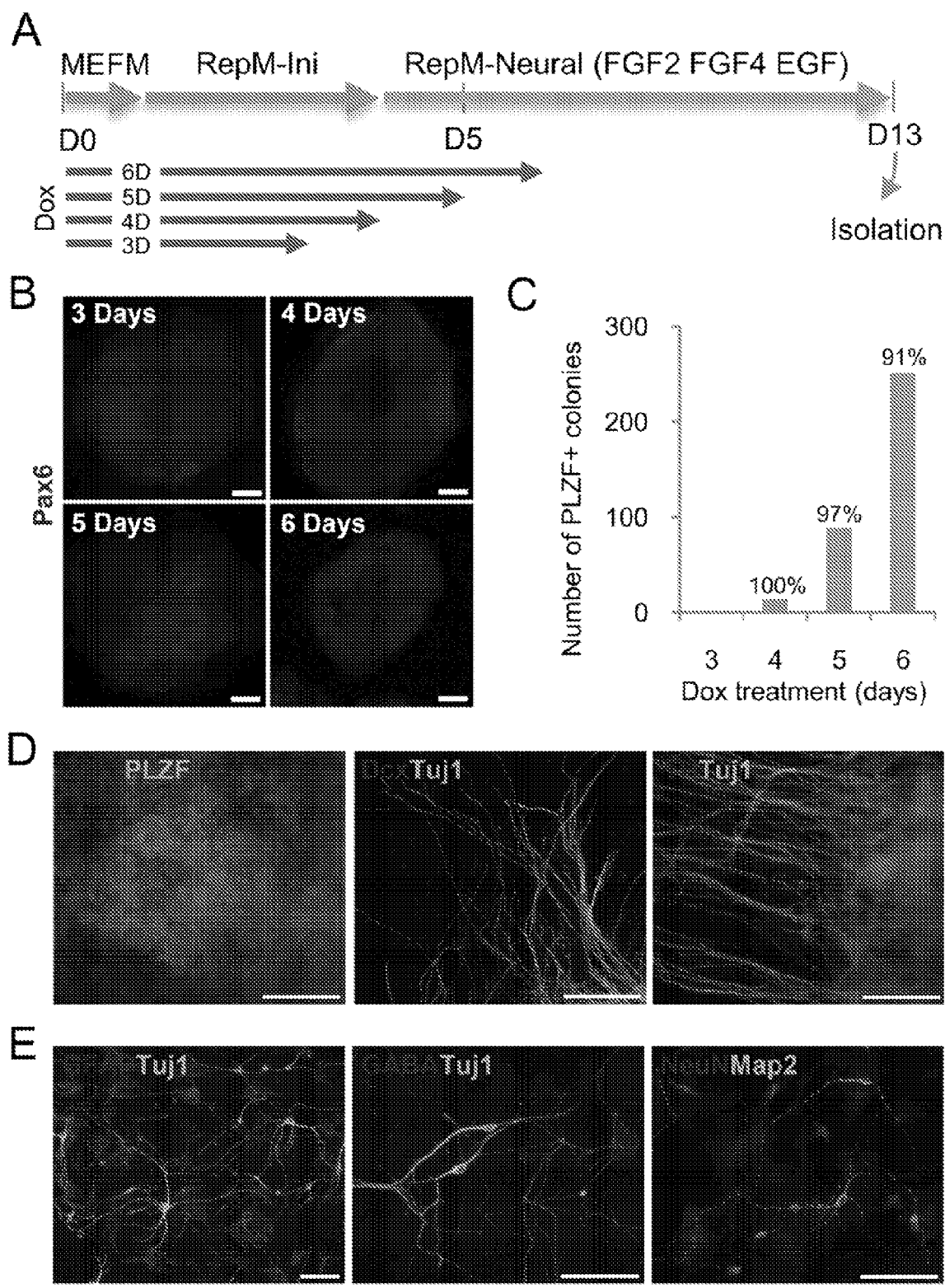
FIG. 7: Transdifferentiation by transient expression of the conventional four reprogramming factors generates functional neural stem/progenitor cells. (A) Scheme for the transdifferentiation of Dox-inducible secondary MEF cells into neural stem/progenitor cells (NPCs). Duration of dox (4 μg/ml) treatment is for the indicated number of days. Different media were added sequentially as described in Methods. (B) Pax6 immunostaining on day 13 of colonies arising from the indicated durations of dox treatment. 8 μg/ml dox was used for the three-day treatment. (C) Number of PLZF expressing colonies generated with different durations of dox treatment, as analyzed on day 13. (D) Immunostaining of colonies on day 13 with various neural or neuronal markers. (E) Immunostaining of spontaneously differentiated cells from isolated colonies on day 13 with various mature neuronal or glial markers. All scale bars represent 100 μm.

To rigorously test our hypothesis, we attempted an inter-lineage transdifferentiation from fibroblasts to NPCs using the doxycycline (dox)-inducible secondary MEF system (Hanna J. et al., *Nature* (2009); Wernig, M. et al., *Nat Biotechnol* 26(8):916-924 (2008); Hanna, J. et al., *Cell* 133(2): 250-264 (2008)). Inducible overexpression allows precise temporal control over the expression of the conventional iPSC-reprogramming factors, avoiding potentially detrimental effects arising from their constitutive overexpression. To ensure the survival of MEFs during the beginning of the reprogramming procedure, they were kept in MEF and reprogramming initiation medium (RepM-Ini; without LIF) for the first 3-6 days of dox treatment. Thereafter, neural reprogramming medium (RepM-Neural) was applied to induce the generation and/or proliferation of nascent NPCs. RepM-Neural contains FGF2, EGF and FGF4 to support NPCs (Ying, Q. L. et al., *Nat Biotechnol* 21(2):183-186 (2003); Hitoshi, S. et al., *Genes Dev* 18(15):1806-1811 (2004)). We tried dox treatments between three and six days to determine the optimal duration of reprogramming factors expression (FIG. 7A). We initially found that a minimum of three days of dox treatment was sufficient to obtain Pax6-positive colonies after additional 8-9 days in culture in RepM-Neural (FIG. 7B). These colonies typically contained several hundred cells that nearly homogenously expressed PLZF, a rosette NSC marker (Elkabetz et al., *Genes Dev.*, 22(2):152-165 (2008)), and Pax6, an early neural transcription factor (Walther, C and Gruss, P, *Development*, 113(4), 1435-1449 (1991) (FIG. 7B,C,D). Extending dox treatment to six days increased the number of colonies (0.59%±0.01, n=2, colony generation efficiency). Surprisingly, we found that almost 100% of colonies showed neural transdifferentation regardless of the tested duration of dox treatment (95.9%±4.6, n=3, FIG. 7C).

Figure 11:
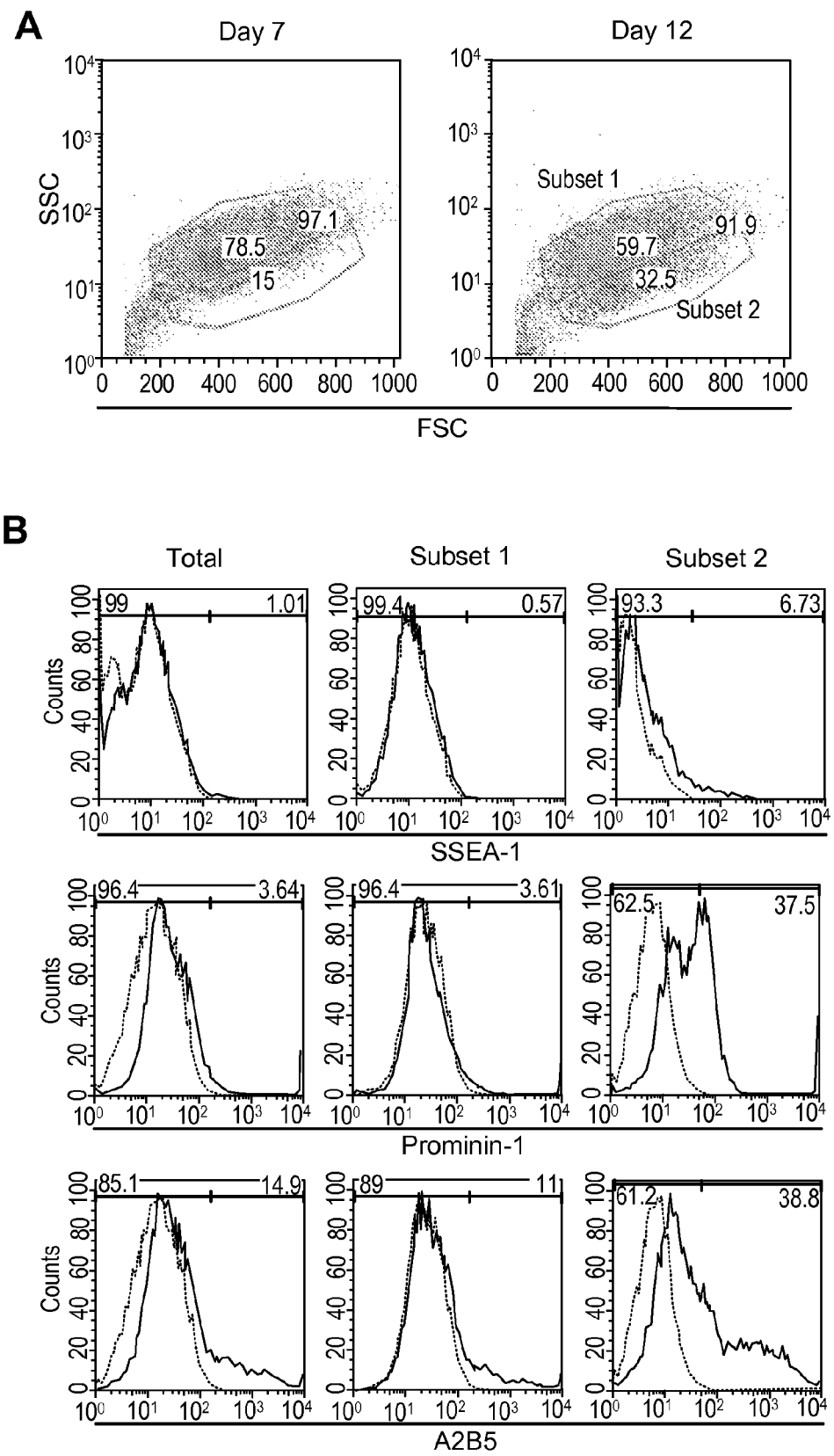
FIG. 11: Flow cytometric analysis of the transdifferentiated NSCs. (A) Forward-and side-scatter FACS plots of day 7 and day 12 samples. In the day 12 sample, cells were divided into two subsets based on gross distribution. Subset 2 is not as prominent on day 7 as on day 12. Subsets 1 and 2 most likely represent the populations of unchanged fibroblasts and colony-forming transdifferentiated cells, respectively. (B) Histograms of cells from day 12 stained with anti-SSEA1, Prominin-1 and A2B5 antibodies. Differently gated (total, subset 1 or subset 2) cells were analyzed separately. (C) Histograms of cells from day 7 and day 12 stained with PSA-NCAM antibody.
Figure 11:
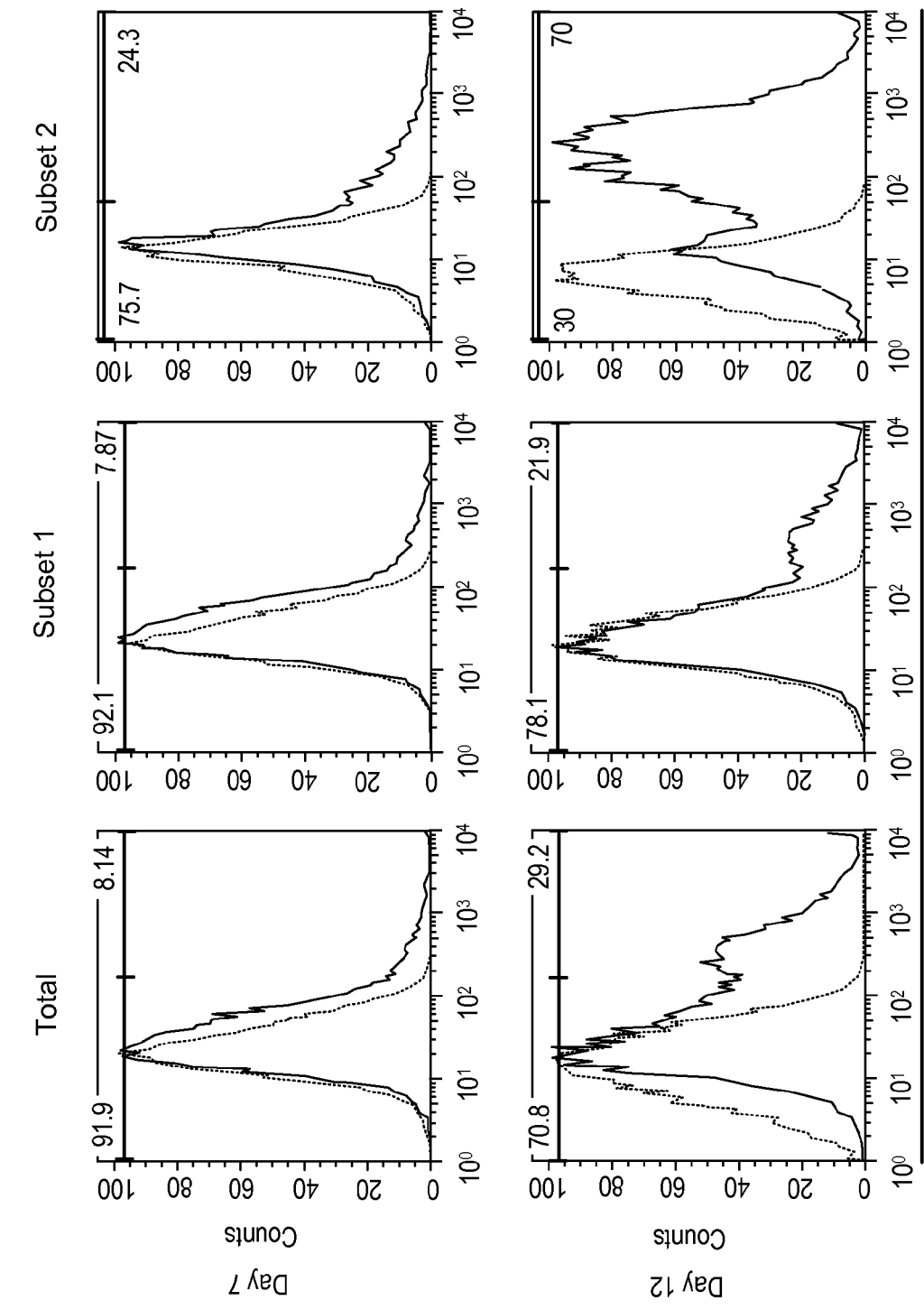

We found typical neural rosette structures, PLZF expression, and luminal expression of ZO-1 (Elkabetz, Y. et al., *Genes Dev* 22(2):152-165 (2008)) in the transdifferentiated colonies (FIG. 7D). In many colonies, we also found Tuj1-positive neurons, some of which co-express the early cortical neuronal marker Dcx, and even the dopaminergic neuronal marker tyrosine-hydroxylase (FIG. 7D). Importantly, these expression profiles are not observed in iN cells (Vierbuchen, T. et al., *Nature* 463(7284):1035-1041 (2010)). Flow cytometry analysis of the transdifferentiated cells revealed that a population of cells expressing Prominin-1, PSA-NCAM, and A2B5 began to emerge after day seven (FIG. 11B,C). This population, in which various neural progenitors (Alcock, J. et al., *Cell Res* 19(12):1324-1333 (2009)) appear to coexist, likely represents the colony-forming cells (subset 2 in FIG. 11A). Notably, this population did not contain a significant number of cells expressing SSEA-1, a pluripotent stem cell marker (FIG. 11B). The heterogeneity of the reprogrammed cells (FIG. 7D) probably reflects parallel paths of reprogramming, some of which result in a more direct transdifferentiation to mature neuronal fates—e.g. because mature neuronal cells coexist with transdifferentiated NPCs (FIG. 7D) and PSA-NCAM-expressing cells were generated as early as day seven in the newly emerging population (FIG. 11C).

Following transdifferentiation, mitotically active neural colonies—which have typically been found to express Pax6 (Walther, C. et al., *Development* 113(4):1435-1449 (1991))—were isolated by manual picking and subcultured en bloc in conventional NPC medium containing FGF2 and EGF for expansion of NPCs (FIG. 7B). Each small cluster could form a colony within several days after isolation; however, despite mild enzymatic passaging and the avoidance of single cell dissociation, the NPCs appeared to lose their ability to form colonies within 3-5 passages. At this point, the NPCs were dissociated into single cells then cultured in N2 medium without any cytokines for further differentiation. After 1-2 weeks of spontaneous differentiation, we observed NeuN and Map2-expressing mature neurons, GABAnergic neurons and GFAP-expressing astrocytes (FIG. 7E). These results collectively suggested that the Pax6- and PLZF-expressing NPCs are functional NPCs that can be differentiated into mature neurons and glial cells. Compared to the circuitous process of reprogramming to iPSCs and subsequent re-differentiation to NPCs, our induced transdifferentiation method—requiring only a single step that is complete within 13 days and showing almost 100% newly generated colonies that are mostly comprised of NPCs—is a highly efficient, direct and rapid process for generating NPCs.

Importantly, the Nanog-GFP marker harboured by the secondary MEF cells was never expressed during transdifferentiation. Indeed, its activation was found to require at least nine days of dox treatment followed by a week of subsequent culture (Wernig, M. et al. *Nat Biotechnol* 26(8):916-924 (2008)). Thus, we concluded that no fully reprogrammed iPSCs were generated within the time span of our experiment, and that the Pax6 and PLZF expressing cells were directly reprogrammed from fibroblasts instead of re-differentiation from intermediate pluripotent cells. To better understand and characterize this transdifferentiation process, we performed additional analyses.

Figure 8:
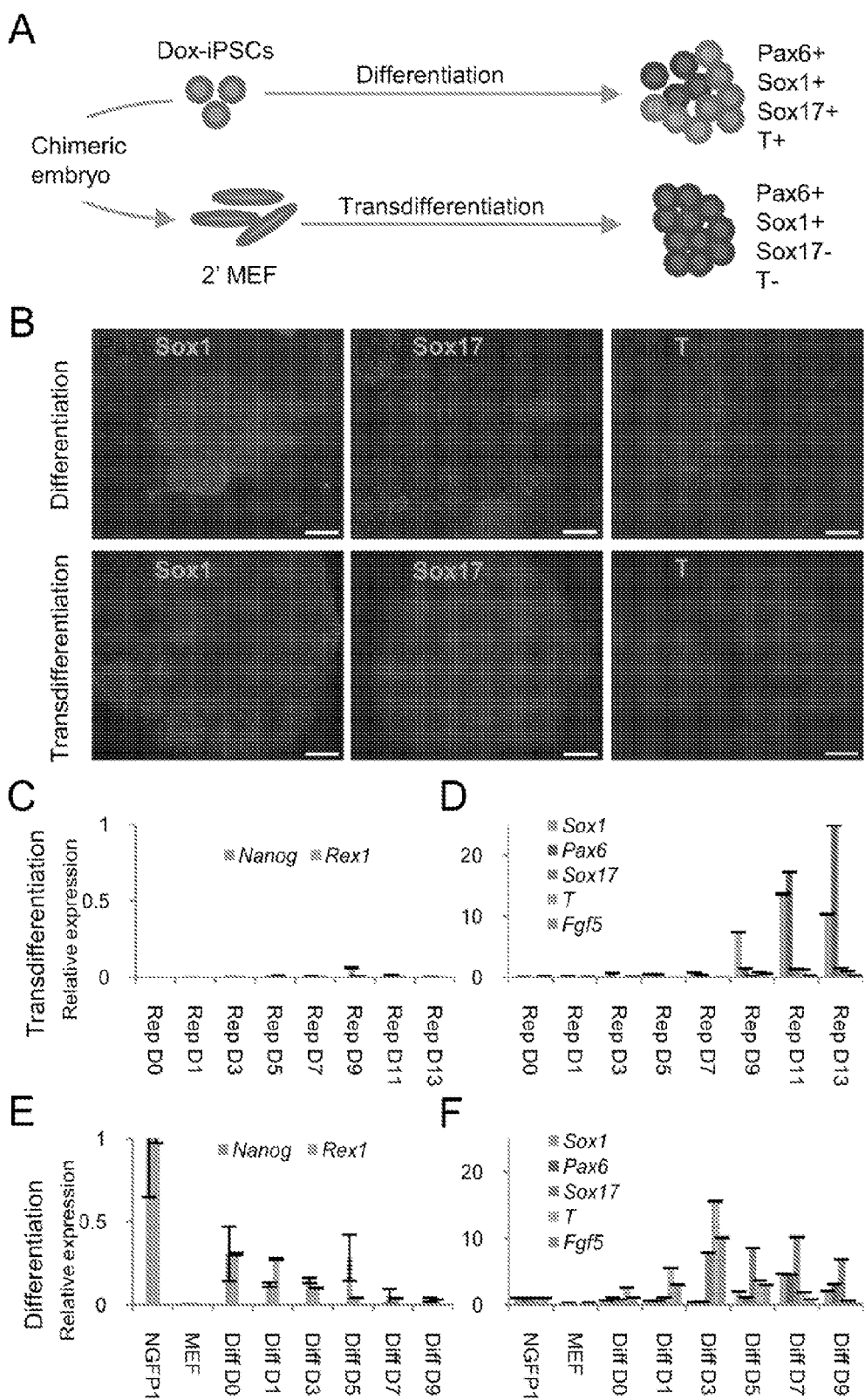
FIG. 8: Direct reprogramming is a highly efficient method of deriving pure neural stem/progenitor cells. (A) Experimental overview and cartoon representation of results from panels B, D, and F. Cells after nine days of differentiation from iPSCs, or after 13 days of transdifferentiation, show the indicated marker expression profiles. (B) Day 9 immunostaining of cells differentiated from iPSCs, or transdifferentiated NPCs on day 13, with antibodies against the indicated markers. Pax6 and Sox1 demarcate early neuroectoderm. Sox17 is indicative of endoderm. T expression is early mesodermal. All scale bars represent 100 μm. (C-F) qRT-PCR analysis of the indicated markers' expression in cells harvested at multiple timepoints during the direct reprogramming process (C,D) and differentiation from iPSCs (E,F). Pluripotency genes (C,E) and lineage-specific genes (D,F) are shown in separate graphs. All values are relative to expression in iPSCs.

First, we sought to more definitively rule out the possibility that the generation of NPCs might first require the formation of transient pluripotent intermediates. To this end, we tested RepM-Neural treatment directly on the iPSCs (NGFP1) which were used in blastocyst injections to make the secondary MEF cells, hypothesizing that we would get results similar to MEFs if the generation of NPCs relied on the generation of a small number of pluripotent cells early in the transdifferentiation process. However, we found that using iPSCs as a starting population resulted in a highly complex mixture of neuroectodermal (Sox1- and Pax6-positive), endodermal (Sox17-positive), and mesodermal (T-positive) cells (FIG. 8A,B). On the contrary, most colonies transdifferentiated from MEFs were almost entirely comprised of cells expressing Sox1, the earliest neuroectodermal marker (Ying, Q. L. et al., *Nat Biotechnol* 21(2):183-186 (2003)), and Pax6 (FIG. 8A,B). RT-PCR analysis corroborated these results, as Sox1 and Pax6 expression was exclusive in transdifferentiation (FIG. 8D). As above, cells generated from iPSCs displayed a much more arbitrary profile of lineage-specific marker gene expression (FIG. 8E, F). Although conventional neural differentiation does not rely on NPC-supporting cytokines, we could not do a comparison in their absence because no cell growth of transdifferentiated cells was ever observed without these cytokines. These results show that transdifferentiated NPCs arise directly from fibroblasts without any dependence on the generation of pluripotent intermediates.

Second, we analyzed neural marker expression over time to pinpoint the onset of neural specification during transdifferentiation. As early as day three, Pax6 expression was increased by 5.6-fold compared to D0 MEFs. Sox1 expression started on day five and increased dramatically thereafter (FIG. 8D). Critically, during iPSC differentiation, Sox1 expression also begins on day five (FIG. 8F). This latter finding implies that if transdifferentiation relied on the generation of a pluripotent intermediate, this intermediate would have to arise at least five days before initial Sox1 expression. Since Sox1 expression commences on day five during transdifferentiation, this leaves no time for the reprogramming of MEFs to pluripotency. Further, even minute amounts of Nanog gene expression are not detected until much later in the transdifferentiation process (FIG. 8C). In short, Sox1$^{30}$ NPCs cannot be arising from putative pluripotent intermediates generated during transdifferentiation.

We also investigated the possible generation of epiblast stem cells (EpiSCs) during the transdifferentiation because FGF2 supports self-renewal of EpiSCs, but could not detect any FGF5 expression (Greber, B. et al., *Cell Stem Cell* 6(3): 215-226 (2010)) at any point in the process (FIG. 8D). In addition, Sox17 and Brachyury (T), which are not only lineage markers but are also highly expressed in EpiSCs (Tesar, P. J. et al., *Nature* 448(7150):196-199 (2007)), were not detected either (FIG. 8D). Collectively, our results strongly support the notion that transdifferentiated NPCs are derived from non-pluripotent intermediate cells arising during the early phase of the process.

Figure 9:
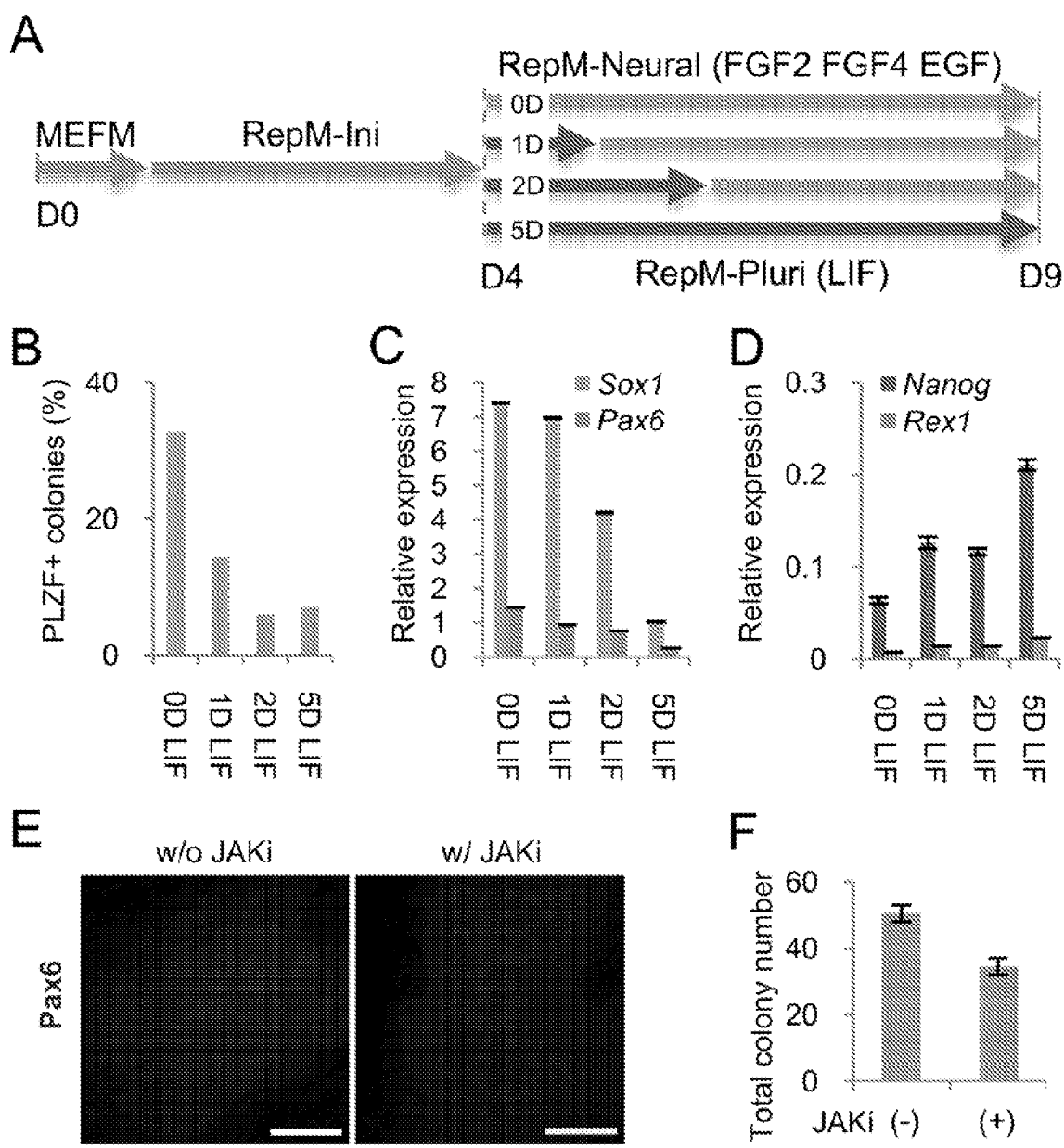
FIG. 9: Fate choice is dictated early during the transdifferentiation process by different environmental cues. (A) Schematic of experiments involving differential exposure to LIF-containing medium (RepM-Pluri) from day 4 onwards for the indicated number of days. Dox treatment was for five days, beginning on day 0 (D0). (B) PLZF-positive colony number expressed as a percentage of the total from each indicated sample on day 9. (C,D) Quantitative analysis of mRNA levels of indicated marker genes in each sample (harvested on day 9). All values are relative to expression in iPSCs. Pax6 immunostaining (E) and total colony number (F) of TTFs transdifferentiated in the presence or absence of JAK inhibitor.
Figure 12:
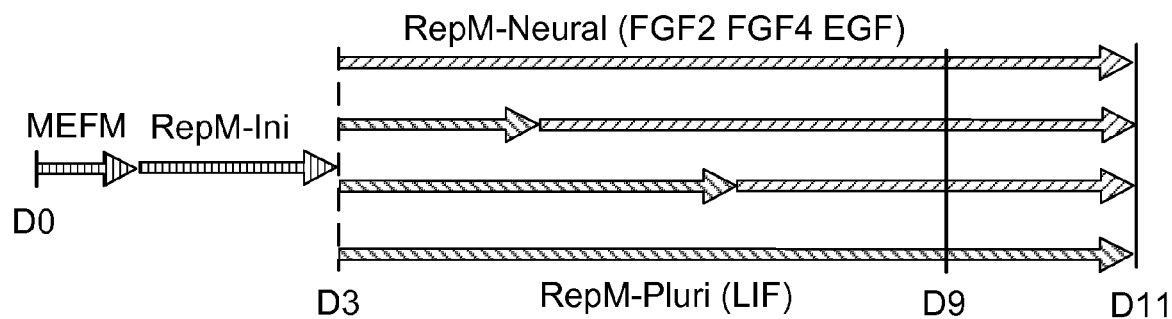
FIG. 12: Flow cytometric analysis of cells temporarily exposed to LIF. (A) Schematic of experiments with differential exposure to LIF-containing medium (RepM-Pluri) from day 3 onwards for 0, 2, 4, and 8 days, respectively. Dox treatment was for five days, beginning on day 0 (D0). (B) Percentage of SSEA1-expressing cells on days 9 and 11. (C) Histograms of SSEA1-expressing cells, as analyzed by flow cytometry.
Figure 12:
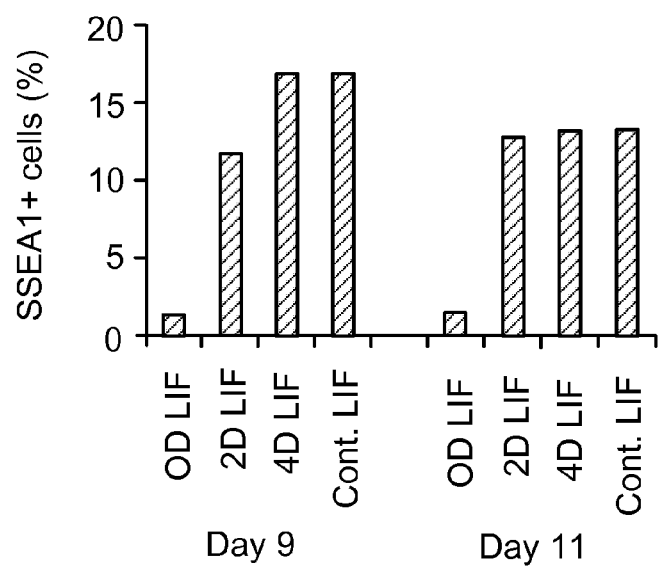
Figure 12:
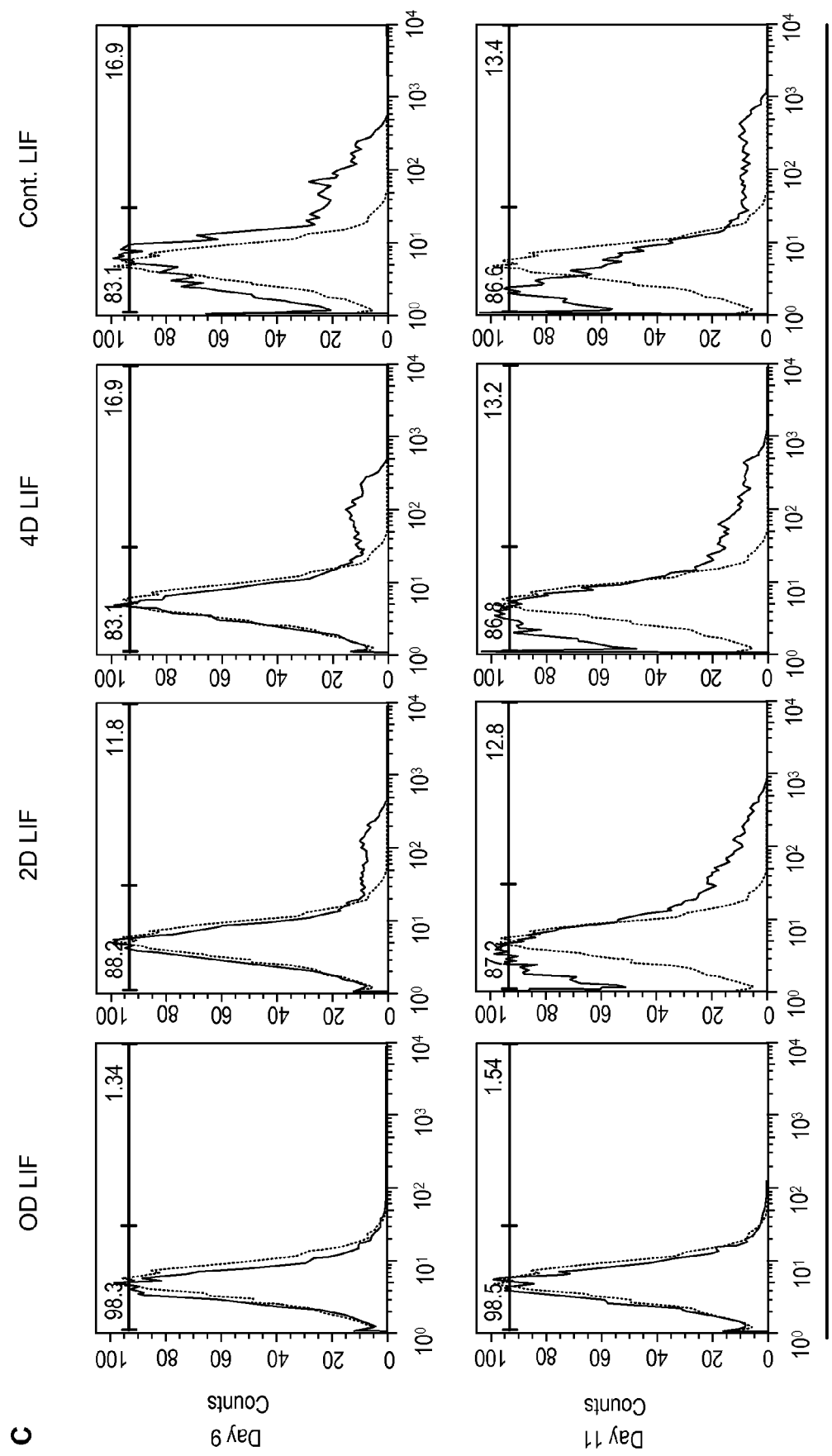

Third, we surmised that the fate choice between NPCs and iPSCs is determined by exposure to signalling specific to each cell type. To test this hypothesis, we examined the effects of using LIF-containing medium (FIG. 9A). Strikingly, even brief exposure (as little as one day) to LIF clearly decreased the number of PLZF-expressing colonies on day nine (FIG. 9B). Conversely, flow cytometric analysis showed that LIF exposure increases the number of SSEA1-expressing cells (FIG. 12B,C). Gene expression analysis also showed down-regulation of Sox1 and Pax6 with concomitant up-regulation of Nanog and Rex1 under the same conditions (FIG. 9C,D). The correlated expression between SSEA1 and Nanog as well as Rex1 implies an overall increase in pluripotent character by extended LIF treatment. Accordingly, we observed that small clusters of Nanog-GFP expressing cells were generated when we used RepM-Pluri throughout (essentially ESC maintenance medium) instead of RepM-Neural. Interestingly, Sox17, T, and FGF5 expression on days 9, 11, and 13 was also increased by LIF exposure (FIG. 13B). This increase in expression of genes specific to other lineages might result from the spontaneous re-differentiation of Nanog-GFP expressing cells generated by LIF exposure or perhaps from an induction of EpiSC-like cells. These results imply that intermediate cells may embark on the path towards becoming iPSCs or NPCs by responding to LIF or NPC-supporting medium, respectively. This cytokine-dependent cell-type specification during direct reprogramming has also been shown in other recent studies (Szabo, E. et al., *Nature* 468 (7323):521-526 (2010); Han, D. W. et al., *Nat Cell Biol* (2010)). Thus, it is clear that the choice between conversion to NPCs and complete reprogramming to iPSCs could be influenced at a very early point during the transdifferentiation process.

Finally, we did not observe any expression of pluripotency (Oct4), neural (Sox1, Pax6), or neuronal (Tuj1) markers in the starting cells or in the cells cultured in RepM-Neural media without dox induction, strongly suggesting an absence of contaminating neural cells in the starting MEF population. Nonetheless, to rigorously rule out any contribution from contaminating neural crest cells and mesenchymal stem cells that might exist in rather heterogeneous MEF populations (Weston, J. A. et al., *Dev Dyn* 229(1):118-130 (2004)), we reprogrammed adult tail-tip fibroblasts (TTFs) using the Dox-inducible STEMCCA system (Sommer, C. A. et al., *Stem Cells* 27(3):543-549 (2009)) following the same method described above. We successfully transdifferentiated TTFs into Pax6-expressing NPCs in 13 days (FIG. 9E) with an efficiency of 0.07% (±0.006% s.e.m.) using just six days of induction—shorter than the eight days required for the generation of pluripotent cells from TTF with this system (Sommer, C. A. et al., *Stem Cells* 27(3):543-549 (2009)).

Because short-term LIF treatment seems to increase the pluripotent character of the reprogrammed cells—although levels of Nanog and Rex1 expression are still quite low compared to iPSCs (FIG. 9D)—a small number of LIF-responsive cells might exist in our cultures. To strictly eliminate the possibility of these cells, we inhibited JAK/Stat3 signalling which is directly involved in pluripotent reprogramming (Yang, J. et al., *Cell Stem Cell* 7(3):319-328 (2010)) by treating small molecular inhibitor of JAK. Although this inhibition decreased the number of colonies by around 30% (FIG. 9F), all remaining colonies homogeneously expressed Pax6 (FIG. 9E). These results imply that our transdifferentiation strictly takes independent path from the pluripotent reprogramming which can be blocked by JAK inhibitor) treatment.

In summary, we have successfully transdifferentiated fibroblasts into functional and proliferating NPCs. Such four iPSC-factors-based transdifferentiation can be guided by modulating transgene expression time and the culture environment (such as specific cytokines) and will prove useful for transdifferentiation to other lineages as well.

Discussion

Figure 10:
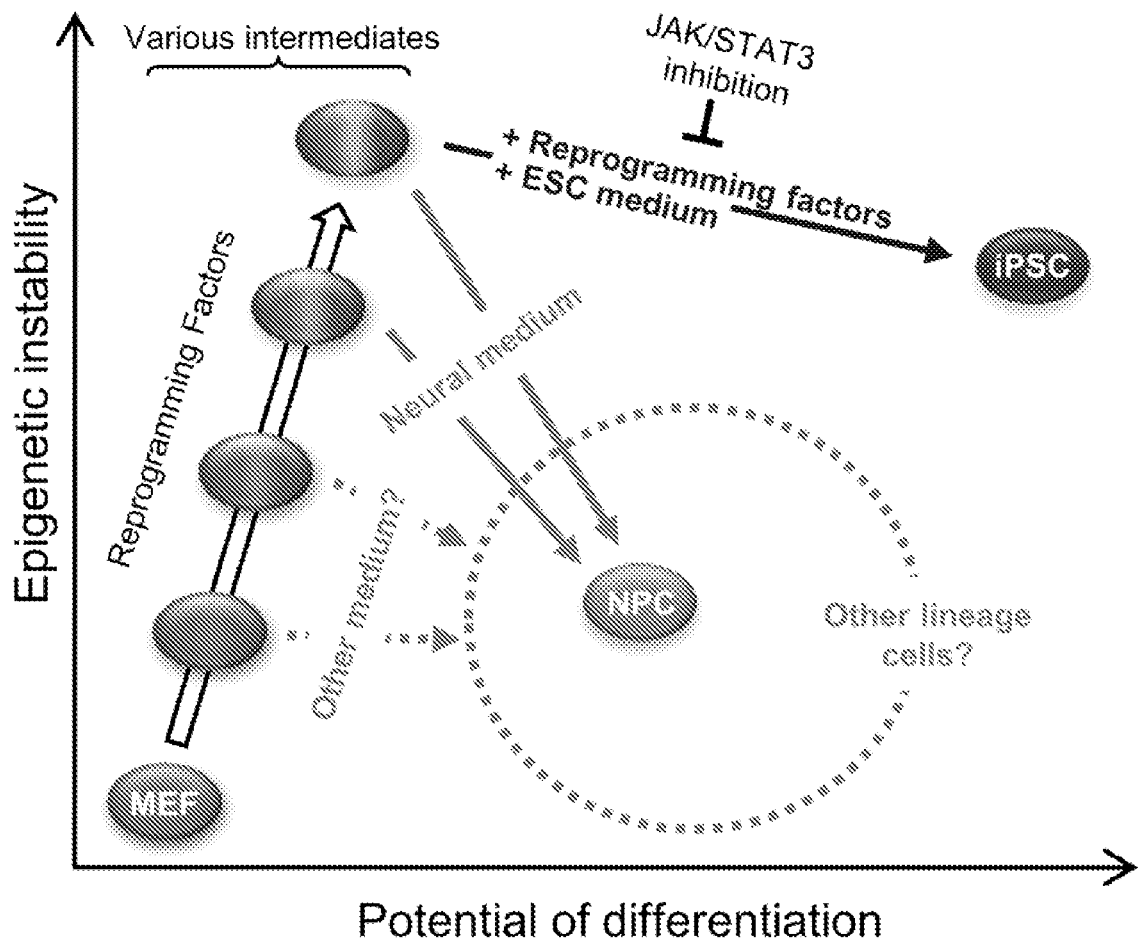
FIG. 10: A model for direct reprogramming of MEFs to neural stem/progenitor cells. By adding neural medium to four factor-induced intermediate cells comprising various epigenetic states, a fate switch to neural stem/progenitor cells (NPCs) can be achieved. Alternatively, iPSCs can be generated by prolonged expression of the four factors with concomitant incubation in ESC medium. Cells belonging to other lineages could likely also be isolated, depending on the type of medium used.

We have shown a direct cell type switch from fibroblasts to functional NPCs by transient expression of the four reprogramming factors, whereby the process is clearly distinct from and does not depend on the generation of iPSCs. This transdifferentiation process is highly specific and efficient, reaching completion within 9-13 days. Our method achieves an inter-lineage cell type change much like that of iN cells (Vierbuchen, T. et al., *Nature* 463(7284):1035-1041 (2010)), with one critical advantage: the resulting cells are expandable progenitor cells. Another advantage of our method is the use of general reprogramming factors instead of lineage-specific transcription factors. Because the four Yamanaka factors were chosen for pluripotent cell generation (Takahashi, K., et al., Cell 126(4):663-676 (2006)), they are generally only considered useful for the derivation of iPSCs. However, our results suggest a different paradigm in which various developmentally plastic intermediate cells may be generated in the process, and that iPSCs are perhaps only one of many possible outcomes of the four-factor reprogramming. The ultimate result may depend largely on extrinsic signalling inputs (FIG. 10). Interestingly, in the newt, Sox2, Klf4, and c-Myc are temporarily up-regulated after lens removal or limb amputation to initiate the regeneration process (Maki, N. et al., Dev Dyn 238(6):1613-1616 (2009)). This observation lends supports to our hypothesis that the four conventional iPSC-factors not only induce reprogramming to iPSCs, but may also be capable of mediating direct fate switching between differentiated cells. Indeed, we have also found that fibroblasts can be transdifferentiated into spontaneously contracting cardiac cells by temporary expression of the same four reprogramming factors under different culture condition within 11 days (Efe et al., in press). These results collectively imply a generally non-specific/undirected reprogramming process induced by the four iPSC-factors (i.e. not specifically directed toward the pluripotent state as it has been regarded), and suggest a new strategy/paradigm to significantly expand and exploit iPSC-factor-based reprogramming. Different transgene expression time and culture conditions may allow a transient, plastic developmental state established early to effectively serve as a cellular platform for transdifferentiation toward various lineages.

Although iN cells are functional neurons (Vierbuchen, T. et al., Nature 463(7284):1035-1041 (2010)), they lack the potential to generate the diverse neuronal subtypes that can be derived from iPSCs. Furthermore, these post-mitotic neurons may not be very suitable to the study of certain neurological diseases, due not only to their non-proliferative state (which severely limits their numbers), but also to their inability to recapitulate disease phenotypes occurring at the neural progenitor stage (Marchetto, M. C. et al., Hum Mol Genet (2010)). Currently, iPSCs derived from patients with late-onset neurological diseases (e.g. those with Parkinson's and amyotrophic lateral sclerosis) do not readily recapitulate disease phenotypes when re-differentiated (Soldner, F. et al., Cell 136(5):964-977 (2009) Dimos, J. T. et al., Science 321 (5893):1218-1221 (2008)), although some patients' iPSCs with genetic defects show their symptoms (Lee, G. et al., Nature (2009); Ebert, A. D. et al., Nature 457(7227):277-280 (2009)). These findings imply that complete reprogramming to a pluripotent state may reset certain epigenetic hallmarks of the disease state, thereby necessitating long-term aging under conditions of stress for its repeated manifestation. Considering this negative correlation between the degree of reprogramming and the manifestation of a particular disease phenotype, we think that the transdifferentiated NPCs—which are derived with limited reprogramming—may prove to be a superior disease model system to iPSCs when studying such late-onset diseases.

Although we used secondary MEF cells, the transdifferentiation process may at first glance seem inefficient compared to iPSC reprogramming using the same cells (Wernig, M. et al., Nat Biotechnol 26(8):916-924 (2008)). However, considering the abbreviated induction period, the efficiency is reasonable, i.e. comparable to initial reprogramming as confirmed by retrospective analyses (Smith, Z. D. et al., Nat Biotechnol 28(5): 521-526 (2010)).

Figure 13:
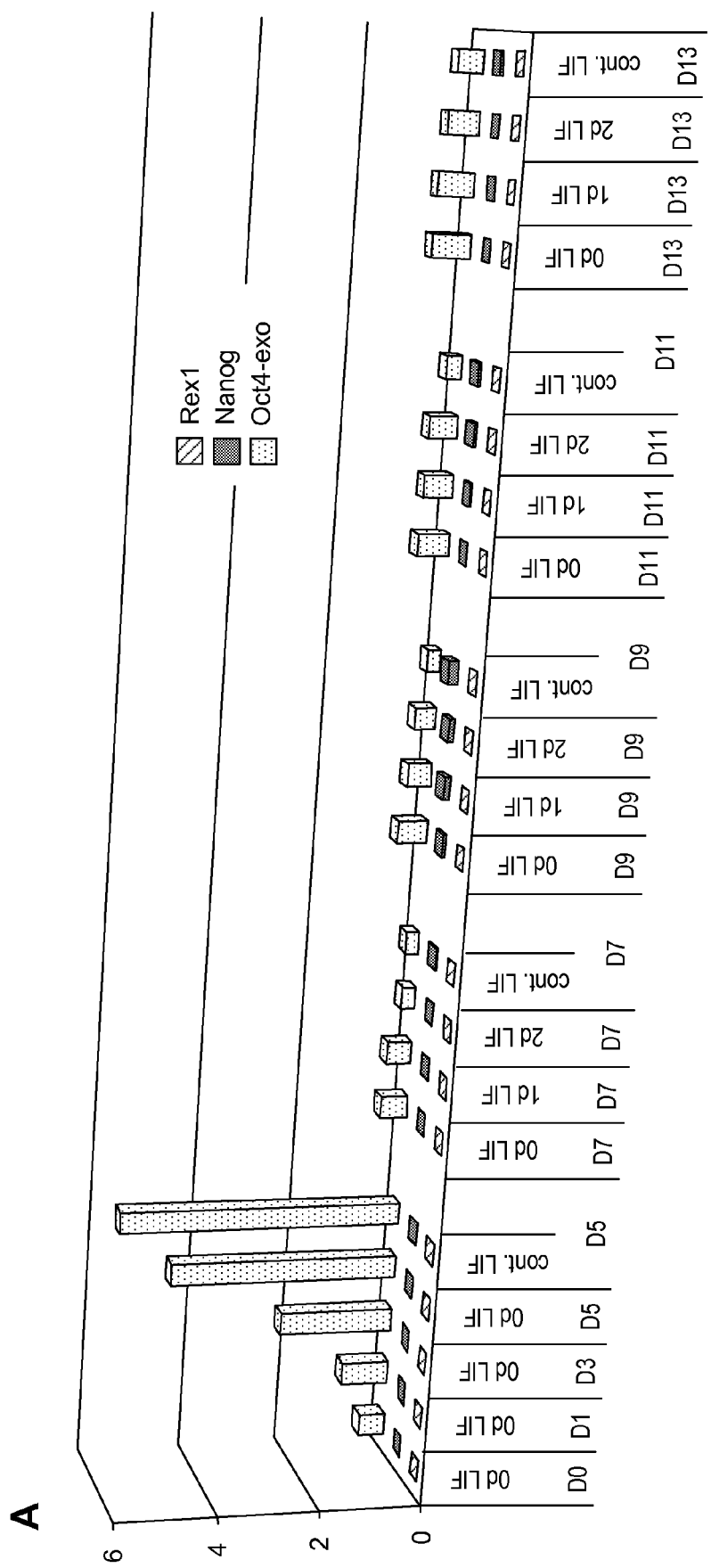
FIG. 13: Quantitation of sequential gene expression during transdifferentiation. The experimental setup is the same as in FIG. 9A, with samples harvested at the indicated time points. Pluripotency genes (A) and lineage-specific marker genes (B) are shown in separate graphs. All values are relative to expression levels in iPSCs. Dox treatment was for five days, beginning on day 0.
Figure 13:
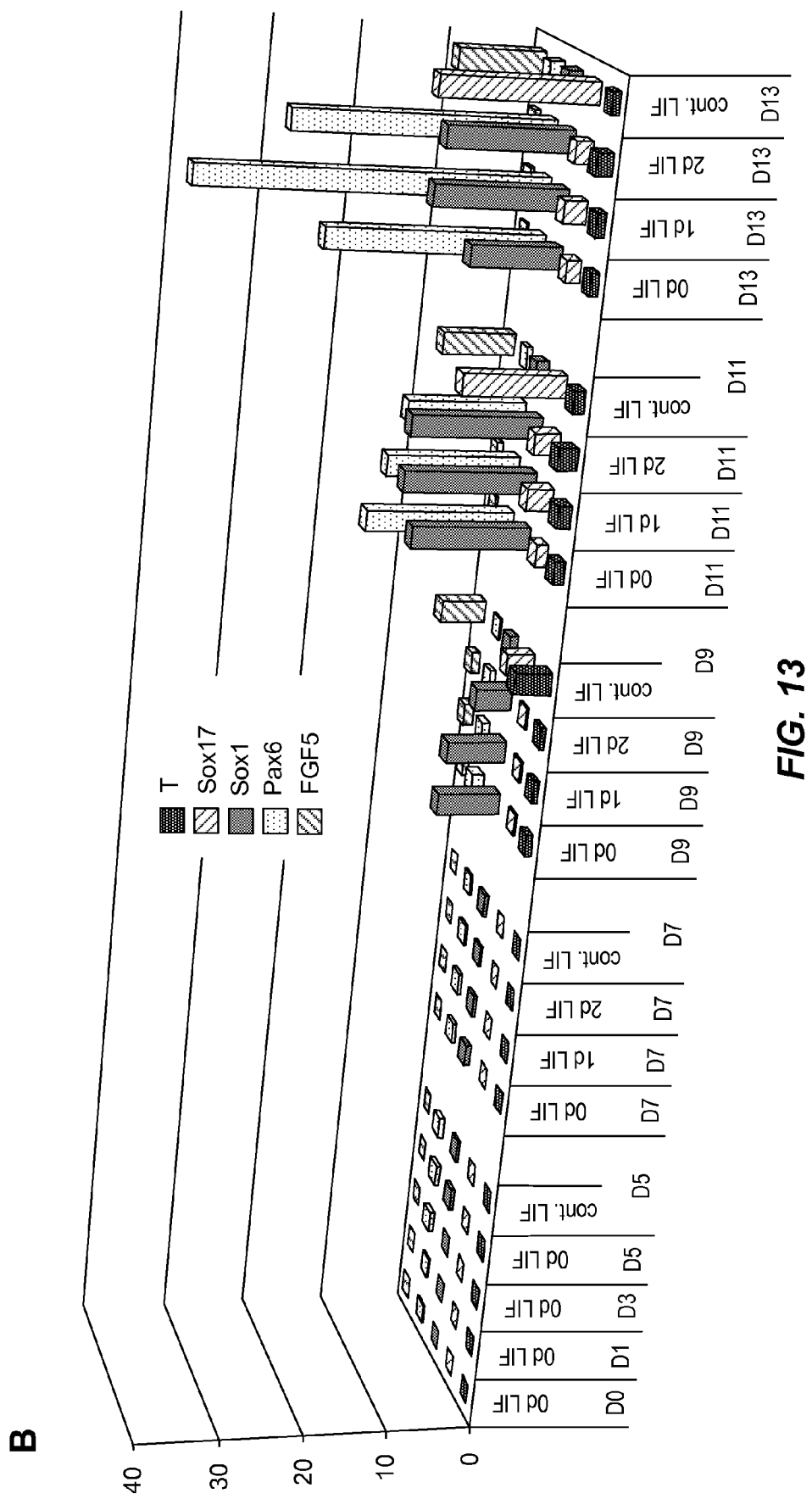

We observed no significant up-regulation of EpiSC markers such as Sox17, Brachyury (Tesar, P. J. et al., Nature 448(7150):196-199 (2007)) and FGF5 (Greber, B. et al., Cell Stem Cell 6(3):215-226 (2010)) during our direct reprogramming. Nonetheless, a recent study by the Schöler group showed direct reprogramming to EpiSCs can be achieved in 3-5 weeks (Han et al., Nat Cell Biol, 13(1): 66-71 (2011)) which is substantially slower than our method. Thus, a temporary emergence of EpiSCs during our direct reprogramming—which can be achieved within 12 days—is highly unlikely. Interestingly, five days of induction followed by long-term LIF treatment caused increased expression of Sox17 and FGF5 with extremely low levels of Brachyury and Nanog (FIG. 13). These cells may partially resemble EpiSCs; however, the absence of LIF in our transdifferentiation media makes the generation of such cells nearly impossible. To achieve fully reprogrammed EpiSCs or iPSCs status, a much longer induction of reprogramming factors may be required.

In a recent exciting development, lentiviral expression of OCT4 alone was shown to mediate direct reprogramming of human cells to blood progenitors (Szabo, E. et al., Nature 468(7323):521-526 (2010)). Although OCT4 expression is down-regulated after long-term differentiation, long-term induction is required and there is always a risk of lentiviral reactivation of OCT4 expression, which may induce dysplastic lesions (Hochedlinger, K. et al., Cell 121(3):465-477 (2005)). Our study shows that temporary expression of four reprogramming factors is sufficient to induce lineage-specific transdifferentiation. When our transdifferentiation process can be replicated using non-viral and temporary expression methods such as transient transfection (Okita, K. et al., Science 322(5903):949-953 (2008); Jia, F. et al., Nat Methods 7(3):197-199 (2010)), protein transduction (Zhou, H. et al., Cell Stem Cell 4(5):381-384 (2009); Kim, D. et al., Cell Stem Cell 4(6):472-476 (2009)), mRNA transfection (Warren, L. et al., Cell Stem Cell 7(5):618-630 (2010)) or small molecules (Zhu, S. et al., Cell Stem Cell 7(6):651-655 (2010)), it will form the basis of safe and convenient transdifferentiation across a broad lineage spectrum.

Materials and Methods

Direct reprogramming and differentiation: NGFP1 Dox-inducible iPS cells (Hanna J. et al., Nature (2009); Hanna, J. et al., Cell 133(2):250-264 (2008)) (Stemgent) were injected into C57BL/6 blastocysts and implanted into surrogate mice (CD1, Harlan). Chimeric embryos were isolated at E12.5-13.5. Heads, developing organs and spinal cords were carefully removed from the embryos and MEFs were prepared and selected as previously described (Hanna J. et al., Nature (2009); Wernig, M. et al., Nat Biotechnol 26(8):916-924 (2008); Hanna, J. et al., Cell 133(2):250-264 (2008)). For reprogramming, secondary MEFs (p3-4) were plated on Geltrex-coated culture dishes at $1.5\text{-}2 \times 10^4$ cells/cm$^2$ in MEF medium (Dullbecco's modified Eagle's medium supplemented with 10% fetal bovine serum, 0.1 mM non-essential amino acids, and 2 mM Glutamax). Doxycycline (Sigma-Aldrich, 2-8 μg/ml) treatment was initiated the next morning (Day 0) and continued until the designated day(s). Cells were cultured in MEF medium for an additional day and changed to reprogramming initiation medium (RepM-Ini; knock-out DMEM supplemented with 10% knock-out serum replacer, 5% FBS, 0.1 mM NEAA, 2 mM Glutamax, and 0.055 mM β-mercaptoethanol) for three days. For neural stem/progenitor reprogramming, the medium was changed into neural reprogramming medium (RepM-Neural; Advanced DMEM/F12 and Neurobasal medium were mixed by 1:1 and supplemented with 0.05% bovine serum albumin, 1×N2, 1× B27, 2 mM Glutamax, 0.11 mM β-mercaptoethanol, 20 ng/ml FGF2, 2 ng/ml FGF4, and 20 ng/ml EGF). RepM-Pluri is the same as RepM-Ini, with the addition of 1000 units/ml LIF (Millipore).

For TTF reprogramming, Lentivirus supernatants were produced and harvested as previously described (Takahashi K. et al. *Cell* 131(5):861-872 (2007)). Briefly, 293T cells (Invitrogen) were plated at $5\times10^6$ cells per 100 mm dish and incubated overnight in a 37° C. incubator. Cells were transfected with 4 μg pHAGE2-TetOminiCMV-STEMCCA (29) or FUW-M2rtTA (Addgene) along with packaging mix (1 μg psPAX2 and 3 μg pMD2.G) (Addgene) and FuGENE 6 Transfection Reagent (Roche), according to the manufacturer's instructions. The cells were then cultured in a 32° C. degree incubator, after which supernatants were collected at 48 and 72 hours (post-transfection) and filtered through a 0.45 μm filter (Millipore) before use. TTFs were prepared as previously described (Takahashi, K., et al., *Cell* 126(4):663-676 (2006)). Briefly, tails (only the final third) were cut into small pieces (less than 0.5 cm) and grown on gelatine-coated plates in MEF medium. Cells that migrated out of the tissue were transferred into new dish and used after one more passage (p3). After two rounds of transduction with STEMCCA and rtTA expressing virus, cells were plated on Geltrex-coated dishes at $2\times10^4$ cells/cm$^2$ and reprogrammed as described above. JAK inhibitor 1 (Calbiochem) was added from day 4 onward at 0.5 μM during TTF transdifferentiation.

For neuronal differentiation, completely dissociated cells were plated on Geltrex-coated plates in N2 medium (Elkabetz, Y. et al., *Genes Dev* 22(2):152-165 (2008)). For differentiation, iPSCs cultured in RepM-Pluri were dissociated into single cells and plated on Geltrex-coated plates. After overnight culture, the medium was replaced with RepM-Neural. All media were replenished at least once every two days. All reagents were purchased from Invitrogen if not specified, and all cytokines are from R&D systems.

Quantitative RT-PCR: Total RNA was extracted from samples at the designated time points using the RNeasy Plus Mini Kit with QiaShredder (Qiagen). One microgram of total RNA per sample was reverse-transcribed using the iScript cDNA synthesis kit (Bio-Rad) and the cDNA was diluted with 130 ul of water. 1/50 of the diluted cDNA was used for quantitative PCR with iQ SYBR Green Supermix on the CFX96 system (Bio-Rad). All qPCR reactions were done in duplicate or triplicate, and the expression data were normalized to both Gapdh and β-actin expression using CFX manager software (Bio-Rad). All primer sequences are listed in previous publications (Hanna J. et al., *Nature* (2009); Wernig, M. et al., *Nat Biotechnol* 26(8):916-924 (2008); Greber, B. et al., *Cell Stem Cell* 6(3):215-226 (2010)).

Immunocytochemical analysis: Samples were washed once with D-PBS (Invitrogen, without Ca$^{2+}$ and Mg$^{2+}$) and were fixed with a 4% pure-formaldehyde solution (Electron Microscopy Sciences) with 0.15% picric acid (Sigma-Aldrich) in D-PBS for 20 min, followed by three washes with D-PBS. Blocking and permeabilization were done with a 3% BSA (Jackson ImmunoResearch) and 0.3% Triton X-100 (Sigma-Aldirch) solution in D-PBS for 1 hr at room temperature. All primary antibodies were diluted in 1% BSA and incubated overnight at 4° C. After 1 hr of washing (including several buffer changes) with 0.1% BSA in D-PBS, samples were incubated with Alexa-555- or Alexa-488-conjugated secondary antibodies (Invitrogen) for 1 hr at room temperature. All images were taken using a Zeiss AX10 microscope equipped with an Axiocam HRm camera, and processed with Axiovision software (Zeiss). Primary antibodies used are Pax6 (Covance, 1:500, rb), Tuj1 (Covance, 1:5000, m or rb), Dcx (SantaCruz, 1:200, gt), TH (Sigma, 1:500, m), ZO-1 (Invitrogen, 1:500, rb), PLZF (EMD chemical, 1:100, m), GFAP (Dako, 1:1000, rb), GABA (Sigma, 1:3000, rb), NeuN (Millipore, 1:50, m), Map2 (Abcam, 1:5000, chk), Sox1 (SantaCruz, 1:300, gt), Sox17 (R&D, 1:1000, gt), and T (SantaCruz, 1:300, gt).

Flow cytometric analysis: Cells cultured until the designated time points were washed with D-PBS and dissociated with Accutase (Innovative Cell Tech). After harvesting, the cells were washed twice with ice-cold FACS buffer (HBSS supplemented with 10 mM HEPES, 2% FBS, and 0.1% Sodium Azide [Sigma-Aldrich]). Undissociated cells were removed by passing suspensions twice through a strainer (BD). Cells were incubated individually with PE-conjugated SSEA1 (BD) and APC-conjugated PSA-NCAM, Prominin-1 and A2B5 (Miltenyi Biotec) antibodies for 30 min at 4° C. (all concentrations as suggested by the manufacturer). Appropriate isotype control antibodies were also used separately. After incubation, cells were washed twice with five volumes of FACS buffer, fixed, and resuspended in 4% pure-formaldehyde solution (Electron Microscopy Sciences) in PBS. More than 20,000 cells were analyzed using FACSCalibur and CellQuest software (BD). For further analysis, FlowJo software (Tree Star) was used.

Example 4

Direct Reprogramming of Human Fibroblasts to Endodermal Cells

Experimental Procedures

Direct reprogramming of human fibroblasts: Human fibroblasts (CRL-2097) were cultured in a 100 mm tissue culture dish and transduced with freshly produced virus supernatants, as previously described. Then 10,000 OCT4 transduced cells were seeded on the Matrigel coated plate and cultured in reprogramming medium and treated with 3 μCHIR99021 (Stemgent) for 1 week, followed by treatment with 3 μCHIR99021, 0.1 mM NaB and 100 ng/ml Activin A for another 3-4 weeks. The CXCR4-positive colonies were picked up for expansion in Expansion medium and passaged at the ratio of 1:3 each time by Accutase. Reprogramming medium: Advanced DMEM/F12, 10% Knockout serum replacement, 1% Glutamax, 1% Non-essential amino acids, 1% penicillin/streptomycin, 0.1 mM β-mercaptoethanol. Expansion medium: Advanced RPMI, 1% Glutamax, 1% Non-essential amino acids, 0.5×N2, 0.5× B27, 1% penicillin/streptomycin, 0.1 mM β-mercaptoethanol, 25 ng/ml Wnt3a, 50 ng/ml EGF and 100 ng/ml Activin A (Stemgent). All cell culture products were from Invitrogen/Gibco BRL except where mentioned.

Production of pancreatic β-like cells: The protocol for further induction of pancreatic β-like cells was modified from previously published literatures. Briefly, iDEs were cultured in medium I and treated with 50 ng/ml FGF7, 2 μM Retinoic acid (RA), 0.1 mM GDC-0449 (a Hedgehog pathway inhibitor), 0.1 mM LDN-193189 (a BMP inhibitor) and 0.5 μM A83-01 (a TGFβ/ALK5 receptor inhibitor) for 5 d; then changed to medium II adding 50 ng/ml EGF and 104 DAPT for 3 d; finally, these cells were cultured in medium III with 10 ng/ml bFGF, 50 ng/ml Extendin-4 and 10 mM Nicotinamide for another 5-7 d. Medium I: IMDM/F12, 1% Glutamax, 0.5% BSA, 0.5×ITS, 0.5× B27, 1% penicillin/streptomycin; Medium II: DMEM, 1% Glutamax, 1× B27, 1% penicillin/streptomycin; Medium III: DMEM/F12, 1% Glutamax, 1× B27, 1% penicillin/streptomycin.

Results

Figure 14:
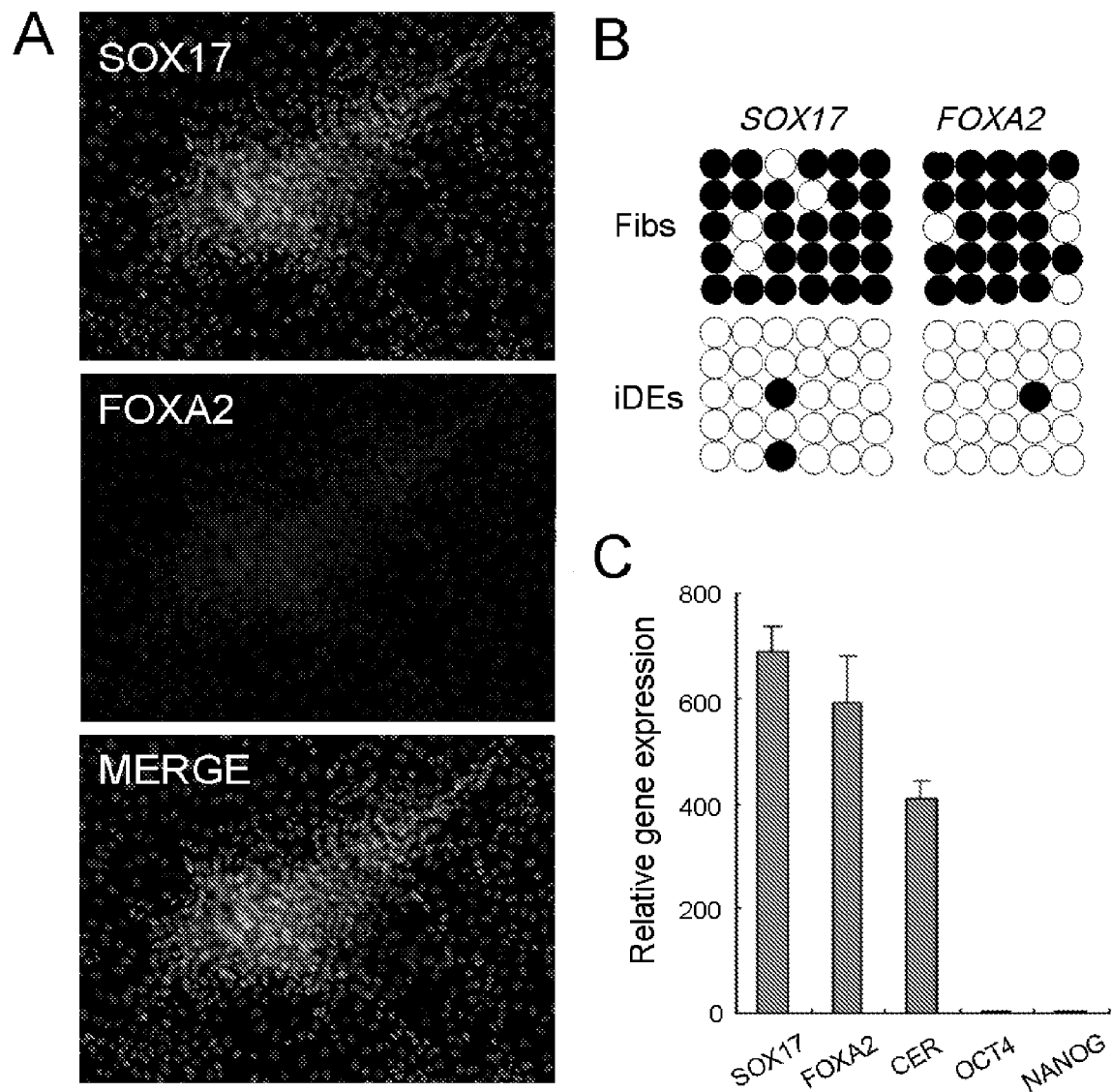
FIG. 14: Direct reprogramming of human fibroblasts to definitive endoderm (iDE) by Oct4 and a unique endodermal inducing condition. (A) shows iDEs positive for both SOX17 and FOXA2, typical markers for definitive endoderm. (B) Bisulfate sequencing analysis shows that SOX17 and FOXA2 promoters are largely demethylated. (C) Expression analysis of pluripotency genes and definitive endoderm marker genes in iDEs.

Direct reprogramming of human fibroblasts to definitive endoderm (iDE): Induced definitive endoderm (iDE) could be generated from human primary fibroblasts by OCT4 and a unique endoderm inducing condition (304 CHIR99021 (a GSK-3 inhibitor), 0.1 mM NaB (an HDAC inhibitor) and 100 ng/ml Activin A (a TGFβ/Activin/Nodal family member)). These iDEs were both SOX17 and FOXA2 positive, a typical characterization for definitive endoderm (FIG. 14A). Bisulfate sequencing analysis revealed that the SOX17 and FOXA2 promoters of iDEs were largely demethylated, providing further evidence for reactivation of the endodermal transcription program in iDEs (FIG. 14B). Additionally, these iDEs expressed specific genes of definitive endoderm, including SOX17, FOXA2 and CER, but did not express pluripotent genes, such as OCT4 and NANOG (FIG. 14C). In conclusion, these iDEs represent typical definitive endodermal cells.

Figure 15:
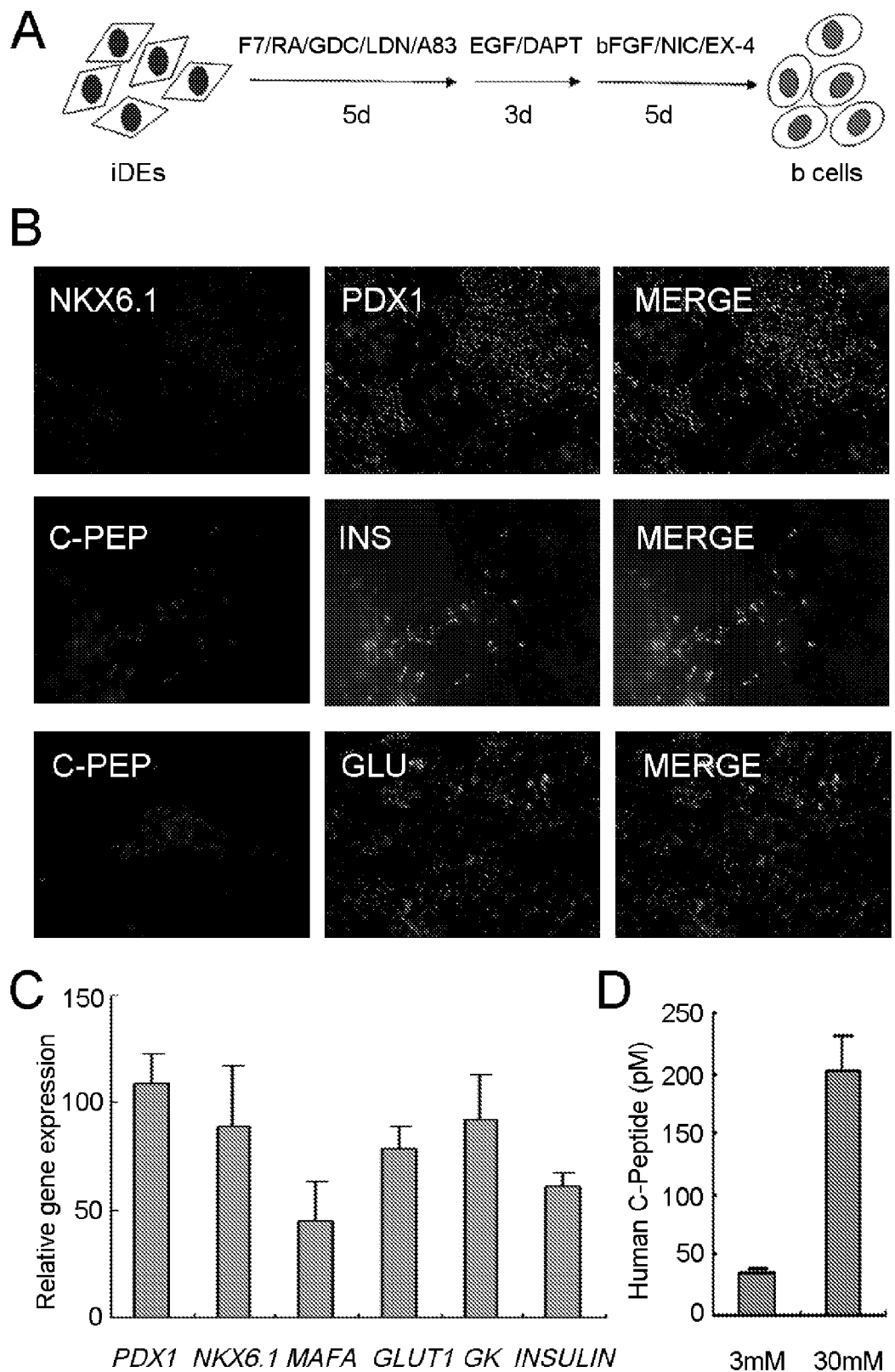
FIG. 15: Direct reprogramming of human fibroblasts to pancreatic lineage cells, such as pancreatic β-like cells. (A) Experimental overview and cartoon representation of results. (B) Immunostaining of iDEs with antibodies against the indicated markers. (B) Real-time PCR analysis of iDE induced pancreatic β-like cells. Expression of islet specific markers genes, including PDX1, NKX6.1, MAFA, GLUT2, GLUCOKINASE and INSULIN, were analyzed. (D) Analysis of C-Peptide released from pancreatic β-like cells derived from iDEs following in vitro glucose stimulation.

Further generation of pancreatic β-like cells: To further investigate the development potentials of these iDEs, we applied a modified protocol for inducing these iDEs to pancreatic-lineage cells (FIG. 15A). After about 2 weeks of stepwise induction and maturation, pancreatic β-like cells were finally generated from these iDEs (FIG. 15B). These pancreatic β-like cells expressed typical lineage-specific markers, such as PDX1, NKX6.1, C-PEPTIDE and INSULIN. These INSULIN-positive cells were also C-PEPTIDE positive, excluding insulin uptake from the culturing media. Real-time PCR analysis showed that these pancreatic β-like cells also expressed islet specific genes, including PDX1, NKX6.1, MAFA, GLUT2, GLUCOKINASE and INSULIN (FIG. 15C). Furthermore, human C-peptide was released from these pancreatic β-like cells on glucose stimulation in vitro, indicating that these pancreatic β-like cells are functional (FIG. 15D). In conclusion, these iDEs could be further induced to insulin producing and glucose responsive pancreatic β-like cells.

Example 5

Direct Reprogramming of Mouse Fibroblasts to Endodermal Cells

Methods of Differentiation

For the preparation of secondary mouse embryonic fibroblasts, NGFP1 Dox-inducible iPS cells (Hanna et al., *Nature*, 26(8):916-924 (2009); Hanna et al., *Cell*, 133(2):250-264 (2008)) were injected into C57BL/6 blastocysts and implanted into surrogate mice (CD1, Harlan). Chimeric embryos were isolated at E12.5-13.5. Heads and developing organs were carefully removed from the embryos and mouse embryonic fibroblasts were prepared and selected as previously described (Hanna et al., *Nature*, 26(8):916-924 (2009); Hanna et al., *Cell*, 133(2):250-264 (2008); Wernig et al., *Nat. Biotechnol.*, 26:916-924 (2008)).

Secondary MEFs (p2-3) were plated on matrigel coated culture dishes at $1\times10^4$ cells/cm2 in MEF media. The medium was changed to Medium I with Doxycycline (4 m/mL) on the next day (Day 0). On Day 5, medium was changed to Medium I with Activin A (10 ng/ml) and JAK inhibitor (0.5 µM). On Day 9, medium was changed to Medium II with RA(2 µM), A83-01(0.5 µM), BMP4(10 ng/ml) and bFGF(10 ng/ml). On Day 12, medium was changed to Medium III (see FIG. 16). Cells were feed every 2 days throughout the whole process. MEF media: DMEM, 2 mM Glutamax, 10% FBS, 1× penicillin/streptomycin. Medium I: Knockout DMEM, 2 mM Glutamax, 10% KSR, 5% FBS, 0.1 mM NEAA, 0.11 mM β-mercaptoethanol, 1× penicillin/streptomycin. Medium II: DMEM, 2 mM Glutamax, 1× B27 media supplement, and 1× penicillin/streptomycin. Medium III: DMEM/F12, 10% FBS, 20 nM progesterone, 100 µM putrescine, 1 mg/mL laminin, 10 mM nicotinamide, 1×ITS premix containing insulin, transferrin, and selenic acid, 1× B27 media supplement, and 1× penicillin/streptomycin.

Results

Figure 16:
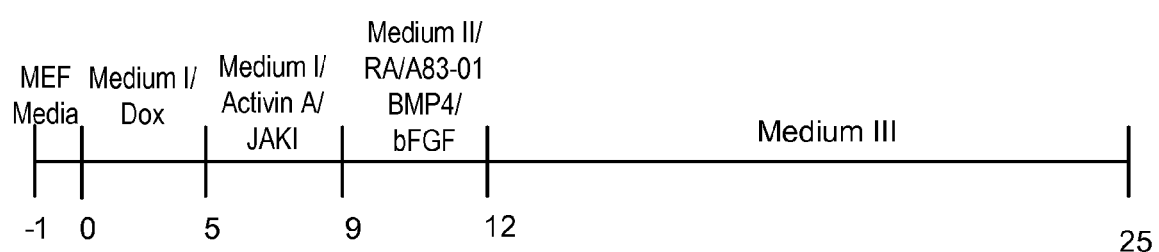
FIG. 16: Transdifferentiation of Dox-inducible secondary mouse fibroblast to pancreatic β-like cells. (A) Schematic overview of the induction protocol. (B) Immunostaining of the induced pancreatic β-like cells with antibody specific to C-peptide.
Figure 16:
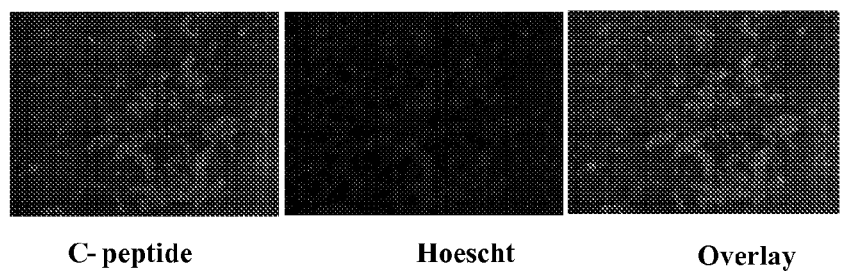

On Day 25, cells were fixed for C-peptide immunostaining (FIG. 16). About 50% of the cells were C-peptide positive.

Example 6

Cardiomyogenesis in Pluripotent Stem Cells

Methods of Differentiation

Pluripotent ESCs represent a potentially unlimited source of functional cardiomyocytes since they can be proliferated in the pluripotent state indefinitely and can be differentiated into beating cardiomyocytes. Realization of this potential is contingent upon the development of consistent and efficient methods of differentiation. The most common method of inducing cardiomyogenesis of murine ES cells involves suspension culture (in the presence of serum and absence of supplemented leukemia inhibitory factor/LIF) to form aggregates (EBs), which differentiate into various cell types, including hematopoietic, endothelial, neuronal and cardiac muscle cells [3]. Isolation of the desired cell type can be achieved through EB dissociation and FACS, followed by replating. When used in combination with specific treatments of growth factors, this has been an effective, though cumbersome, method of generating cardiac cell types and has been particularly useful in the identification of cardiac precursor cells. While the differentiation protocols described above have great utility, they are still not optimal for the study of factors influencing cardiac specification. In particular, media components such as fetal bovine serum (FBS) and Knockout Serum Replacement (KO-SR) contain undefined compositions including growth factors; for example KO-SR has been shown to have bone morphogenetic protein (BMP) activity. The use of undefined media can obscure and complicate the analysis of factors affecting cardiomyocyte differentiation. Additionally, the 3-dimensional nature of the EB model of cardiomyocyte differentiation makes it difficult to obtain homogeneous populations of cells due to the presence of diffusion gradients within embryoid bodies and three-dimensional cell-cell interactions. As EB differentiation is similar to that of the developing embryo, it inherently involves the generation of heterogeneous populations of cells. In contrast, monolayer differentiation provides a greater ability to provide a specific and uniform local concentration of growth factors.

An alternate strategy to EB differentiation that has proven successful in the human system is the coculture of ESCs with a cell line that can direct cell fate. In particular, by culturing the hESC lines hES2 and hES3 with a mouse endoderm-like cell line (END2), an average of 25% cardiomyocytes can be derived. [9] The authors speculate that unknown factors secreted by the endodermal cells, may be directly stimulating the differentiation of cardiomyocytes. Unfortunately, the coculture method is not a defined system, and as such, it is difficult to pinpoint the underlying mechanisms of its success.

A method of differentiation which has proven successful in differentiation of neural and endoderm derivatives has been monolayer differentiation in serum-free media. As discussed, serum-free media afford precise and repeatable determinations of the effectiveness of given signaling mechanisms in cell fate specification. As such, considerable progress has been made using these systems of differentiation to understand the mechanisms governing ectoderm and endoderm derivative specification. To date, similar success has yet to be achieved with the differentiation of cardiomyocytes, and as such, there are several outstanding questions regarding cardiac fate specification.

Signaling Mechanisms Involved in Cardiomyogenesis

Wnt Signaling

While the importance of the canonical Wnt pathway in cardiomyogenesis has long been appreciated, the modality in which it promotes cardiovascular development is unclear as both activators and inhibitors of Wnt signaling have been reported to have positive effects. Experiments with chick embryos demonstrated that the Wnt antagonists Dickkopf-1 and Crescent, released by the adjacent anterior endoderm, stimulate the differentiation of cardiac mesoderm. Similarly, in frog embryos, Dickkopf-1 and Crescent diffuse from Spemann's organizer and stimulate cardiac differentiation in the adjacent mesoderm. In mouse embryos as well, conditional inactivation of β-catenin in the definitive endoderm resulted in ectopic heart formation [10]. On the other hand, Wnt signaling is known to be essential to all aspects of cardiomyogenesis in *drosophila*. Studies concurrent with our own, have suggested a biphasic role of Wnt signaling in cardiac development in the mouse.

BMP Signaling

Much like Wnt signaling, the importance of BMP signaling in cardiac development is appreciated though the specific mechanisms are unclear. Initial studies in amphibian and chick embryos demonstrated that BMP signaling mediates cardiac specification by the adjacent endoderm [15]. BMP signaling was subsequently shown to be essential in vertebrate heart formation, too [16]. Conversely, treatment with the BMP inhibitor Noggin resulted in a marked increase in cardiomyogenesis in an EB model of mouse ES cell differentiation [17]. This study aims to identify a monolayer serum-free condition for the differentiation of cardiomyocytes that can be used to clarify the specific factors and signaling required for stimulation of this transition.

TGF-Beta/Activin/Nodal

In a series of studies, Keller used an ES cell line marked with GFP targeted to the mesendodermal specific gene brachyury to quantify mesoderm and endoderm induction and to isolate and characterize these populations. In short, it was found that in conjunction with Wnt treatment, Activin could indeed induce the formation of primitive streak like cells (Bry+). Furthermore, using a doubly marked GFP-Bry CD4-Foxa2 ES cell line, they were able to assess whether the primitive streak cells formed were anterior (high Foxa2) or posterior (low Foxa2). It was determined that higher concentrations of Activin A stimulated the formation of anterior primitive streak cells; cardiac fate was isolated to cells in this fraction.

Small Molecules Affecting Cardiac Differentiation

Using mESCs stably transfected with the cardiac muscle specific α-myosin heavy chain (αMHC) promoter-driven enhanced green fluorescence protein (EGFP) as a reporter, Takahashi et al. screened 880 known drugs in monolayer culture and found that ascorbic acid (vitamin C) can significantly enhance spontaneous cardiac differentiation of mESCs. Interestingly, other antioxidants such as N-acetyl-cysteine or vitamin E do not have a similar effect, thus suggesting that the cardiomyogenesis inducing activity of ascorbic acid may be independent of its antioxidative property.

Concurrent with this work, the Schultz lab screened large combinatorial chemical libraries using P19 cells that were stably transfected with the cardiac muscle specific atrial natriuretic factor (ANF) promoter-driven luciferase reporter, and found a series of diaminopyrimidine compounds, named cardiogenol A-D, that can efficiently and selectively induce P19 and mESCs to differentiate into cardiomyocytes. The differentiated cells expressed multiple cardiac muscle markers, including GATA-4, Nkx2.5, MEF2, and myosin heavy chain (MHC), and formed large areas of spontaneously beating patches.

Using P19 embryonic carcinoma cells with a stably integrated Nkx2.5-firefly luciferase BAC, Olson et al. screened the 147,000 compounds University of Texas Southwestern chemical library to find activators of cardiac fate. The researchers initially found NaB to be an activator of Nkx2.5-luc expression and thus used this as a positive control in their screen. Using a chemoinformatic approach, the researchers identified a particular family of sulfonyl-hydrazone (Shz) small molecules as being the most promising. The molecules were shown not to be HDAC inhibitors, did not activate the CMV promoter in P 19CL6 cells, and could not direct neuronal differentiation in stem cells.

In an in vivo small molecule screen aimed at identifying chemicals that might modulate dorsoventral patterning, the group recently identified dorsomorphin (6-[4-(2-Piperidin-1-yl-ethoxy)phenyl]-3-pyridin-4-yl-pyrazolo[1,5-a]pyrimidine), a molecule which can selectively inhibit the BMP type I receptor. Since the growth factor Noggin, an inhibitor of BMP signaling, had previously been shown to promote cardiac differentiation in an EB model of mouse development, the authors tested dorsomorphin for cardiac inducing effects. The authors report that treatment of ES cells with dorsomorphin for only the first 24 hours of differentiation induced robust cardiac differentiation, while Noggin treatment had been reported to be effective when treated for a 5 day span including 3 days before differentiation. The authors postulate that dorsomorphin induces cardiac differentiation by restricting differentiation of other cell types including the endothelial, smooth muscle, and hematopoietic lineages.

Small Molecule Screen for Regulators of Cardiomyogenesis

Generation and characterization of an Nkx2.5-GFP ESC line: One of the challenges of assessing differentiation efficacy and efficiency is the method of determining which cell types are generated. Common analyses which identify cell type include RT-PCR, western-blot, immunostaining and functional characterization (eg. beating cells). With the exception of some functional characterizations, all of these methods involve the termination of the experiment as the cells must be harvested or fixed. An alternative strategy is to mark the cells with a fluorescent protein (GFP) under the control of a promoter specific for the cell type of interest. In choosing a marker for a cell type, it is usually best to choose the earliest expressed gene that is also specific for the cell type, often a transcription factor gene as these generally precede the expression of structural genes. In addition to being specific, the marker should also be ubiquitously expressed in the specific lineage of interest. Numerous transcription factors are expressed in the developing heart where they direct and control cardiac specific gene expression and regulate cell fate. Perhaps the most quintessential cardiac specific transcription factor is Nkx2.5. Nkx2.5 is expressed throughout heart development as well as in cardiomyocytes. Additionally, the Nkx2.5 gene has ubiquitous expression in the heart tube, unlike some other cardiac linked transcription factors (Tbx5) that can be expressed sporadically in the anterior-posterior axis of the heart tube.

Figure 17:
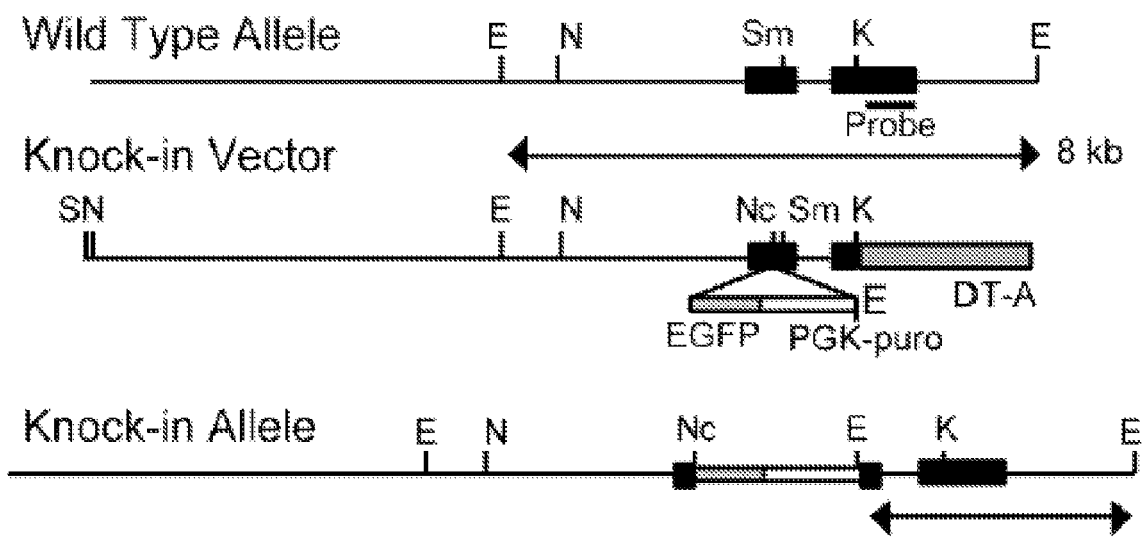
FIG. 17: Nkx2.5 GFP Targeting Vector.

Construction of the Nkx2.5-GFP ES cell: A pCSX-EGFP-PP-DT targeting plasmid containing an Nkx2.5 EGFP vector was obtained from the Morisaki group in Osaka, Japan as seen in FIG. 17.

Figure 18:
FIG. 18: Nkx2.5-GFP Cardiomyocytes Express Low Levels of GFP.

Of all the clones selected as having inserted the knock-in vector, 10 cell lines with the correct GFP insertion into the Nkx2.5 locus were expanded for testing. Hanging drop embryoid bodies were generated for each cell line and monitored daily for GFP expression. Unfortunately, GFP expression was not clearly visible in any of the clones, as is shown in FIG. 18 (nuclei stained blue with DAPI in a contracting region that is negative for Nkx2.5-GFP expression).

Figure 19:
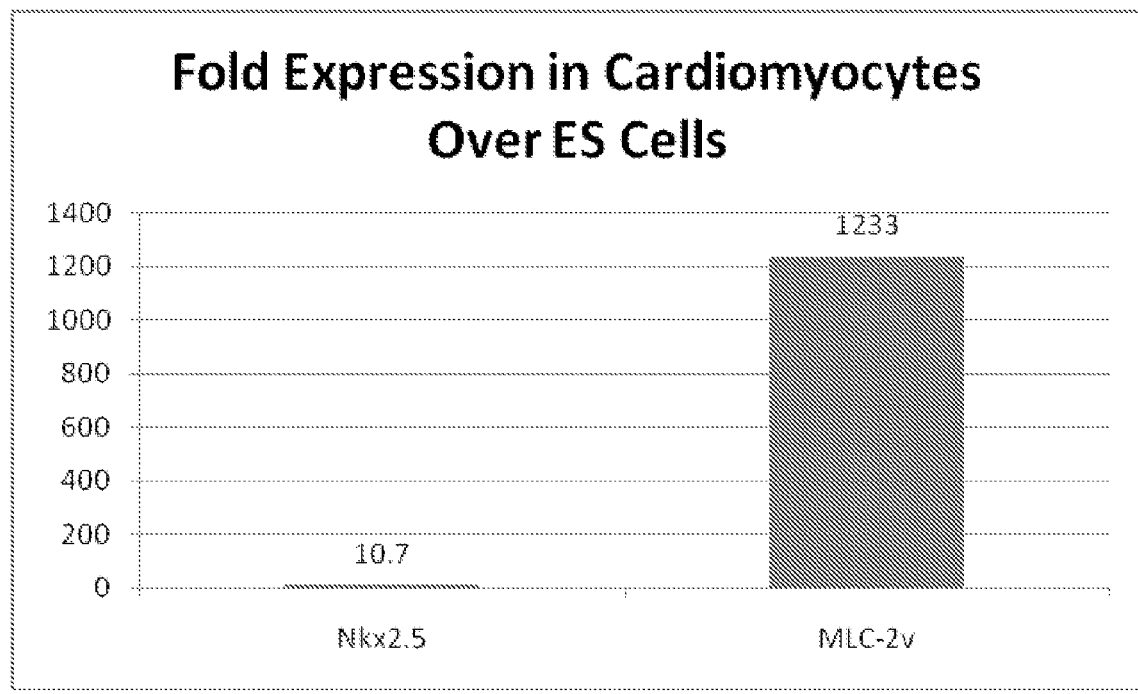
FIG. 19: Transcript Expression Levels in Cardiomyocytes.

Cells were differentiated further into beating colonies which also showed levels of GFP expression that were marginally visible under the fluorescent microscope. As such, we determined that these cells would be inappropriate for the monitoring of cardiac differentiation in high-throughput screening setting. Further research with a collaborator (Burcin, Novartis) indicated that despite its crucial role in cardiac development Nkx2.5 transcript levels only increase 10 fold over there basal levels (FIG. 19) while differentiating whereas the structural gene MLC-2v is more than 1000 fold upregulated cardiomyocytes.

Figure 20:
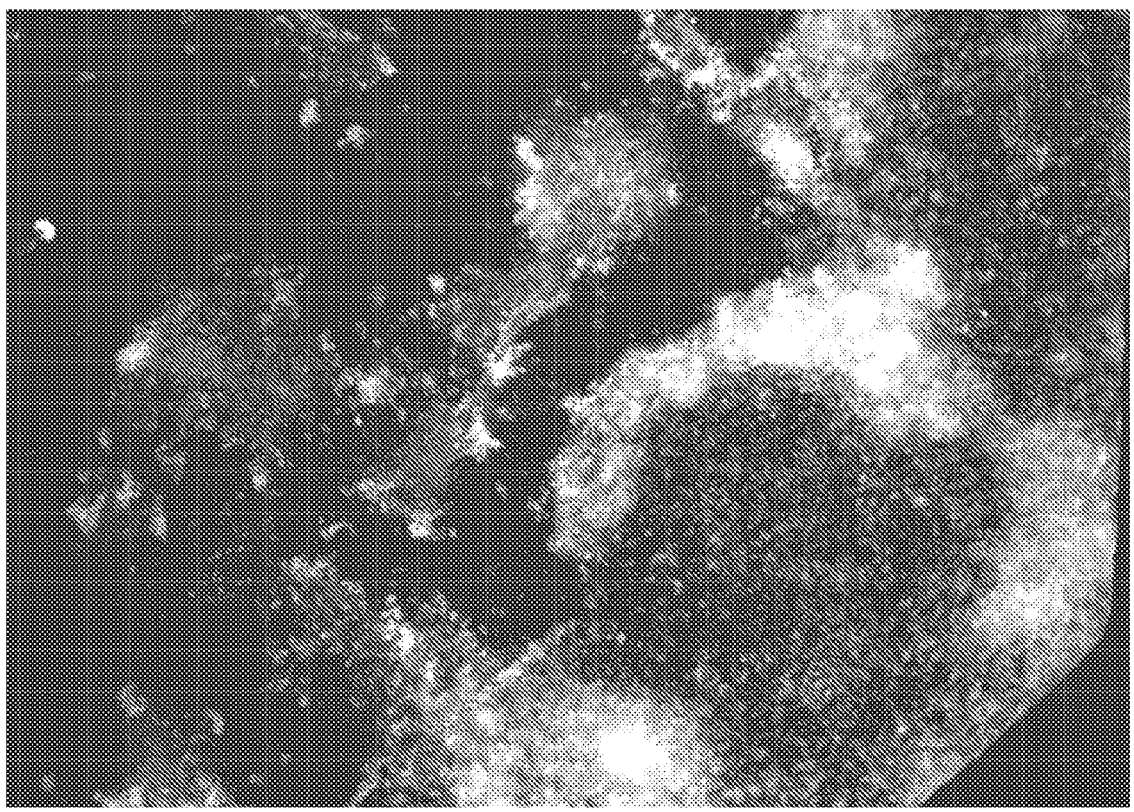
FIG. 20: MLC-2v-GFP Cells Express GFP in Beating Patches.

Having determined that Nkx2.5 would not be an appropriate marker for cardiac differentiation, we sought to identify other markers that might be more suitable. Our collaborator at Novartis, Mark Burcin, had recently developed an MLC-2v-GFP ES cell line, that his lab had yet to characterize. Similar to the validation of the Nkx2.5 lines, we generated hanging drop EB's with the MLC-2v-GFP cells in order to spontaneously differentiate cardiomyocytes. Unlike transcription factors, a structural gene such as myosin should be very highly upregulated above basal levels. Additionally, as MLC-2v tends to mark ventricular cells (those most affected in a myocardially infracted heart) we reasoned that this would be an excellent marker for differentiation. Upon examination of beating regions of cells under the fluorescent microscope, GFP expression was observed in the contracting cells, as well as in some cells surrounding the contracting cells. Shown in FIG. 20 is a representative image of MLC-2v—GFP expression of EB differentiated cardiomyocytes with blue nuclei stained with DAPI). While we hoped for a more specific pattern of expression, we felt these cells would be sufficient to proceed with a small molecule high-throughput screen.

Figure 21:
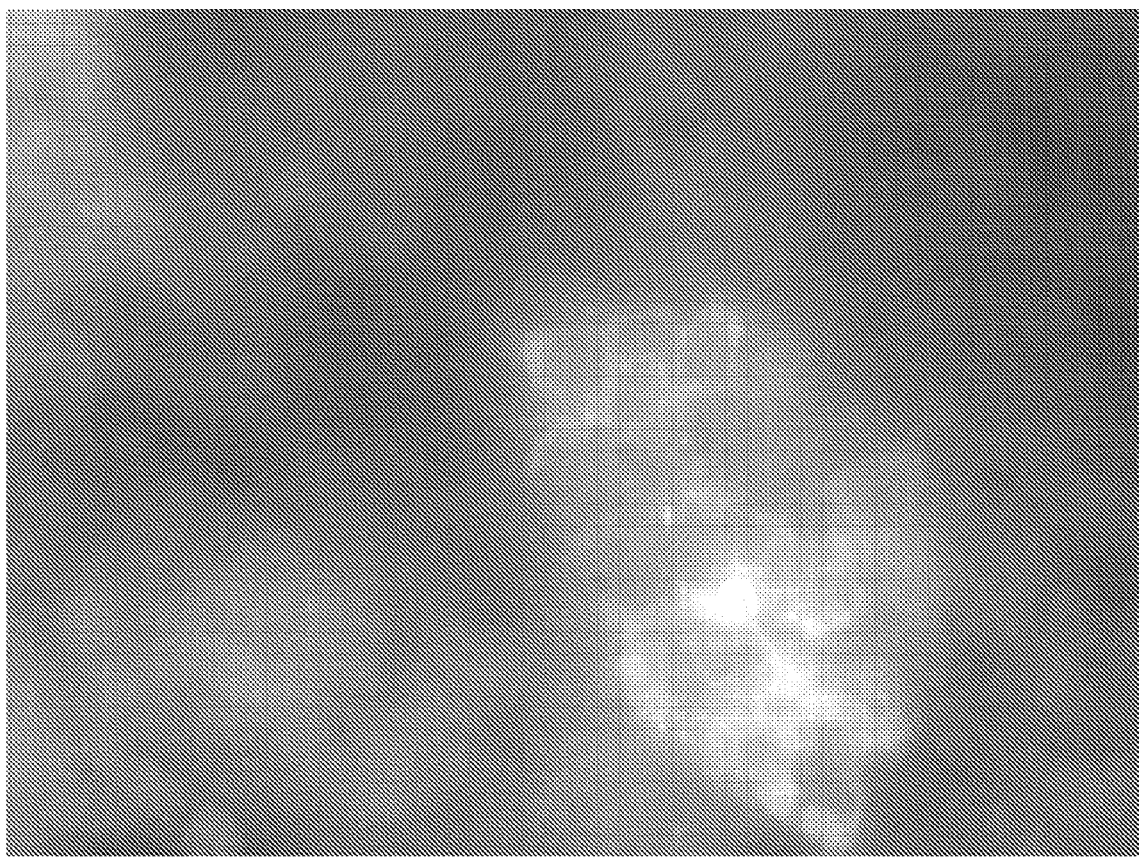
FIG. 21: A Permissive Percentage of MLC-2v-GFP Cells Differentiate Into Cardiomyocytes.

To set up a screen for molecules capable of inducing cardiomyogenesis in ES cells, we first sought to identify a permissive condition. Ideally, a permissive condition is one in which a low percentage of cells differentiate into cardiomyocytes in the absence of a positive control. Too high of a percentage would mean the signal of a 'hit' molecule would not be significantly higher than the background signal, and too low of a percentage could mean that the condition would not allow cardiac differentiation, and potential hits would thus be missed. We decided to use 384-well plates, as these had sufficient area for cell survival and cell homogeneity. As serum is capable of inducing mesodermal differentiation, we opted to use a media similar to ES cell media without the self-renewal factor LIF. Various plating densities were tested and it was determined that 5,000 cells per well was sufficiently dense, without being overly dense causing cells to overgrow and die. Media was replaced every 3 days, and cells were observed under the fluorescent microscope to identify the ideal time for GFP observation. By day 15, we observed approximately 1% of cells expressed in GFP, though no beating regions were observed. Shown in FIG. 21 is a small patch of GFP positive cells differentiated in chemically defined medium on Matrigel in a serum-free defined medium.

Figure 22:
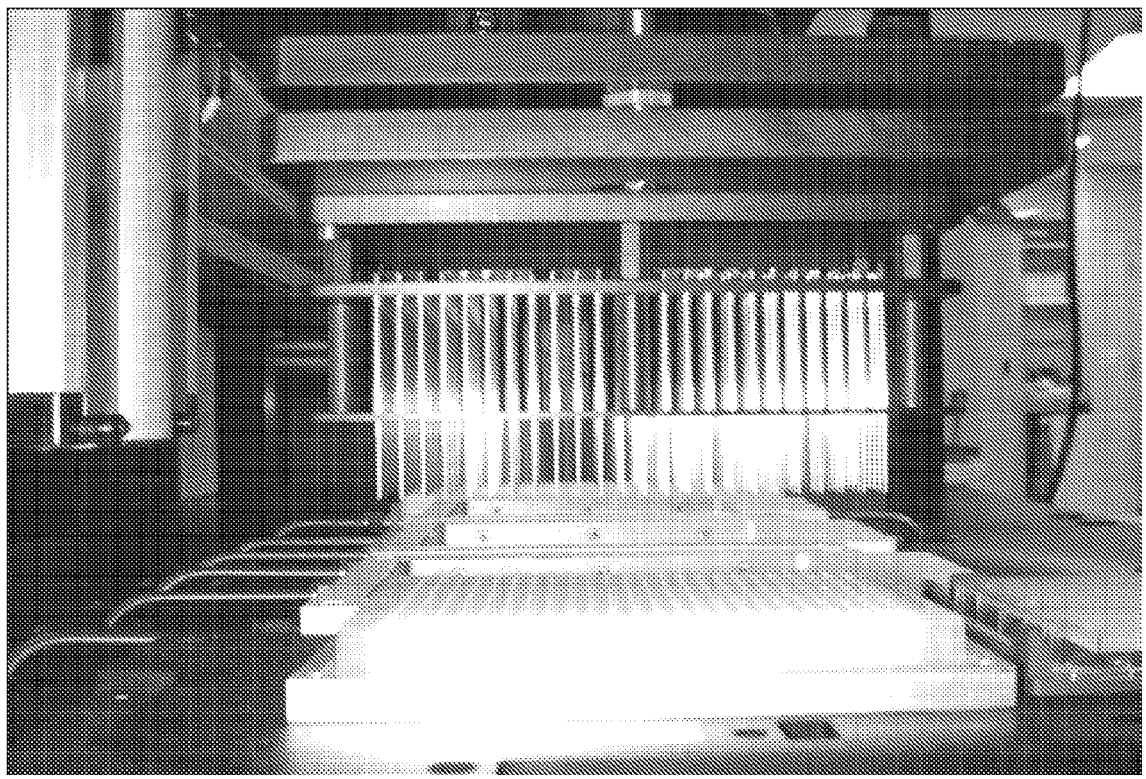
FIG. 22: Pintool Technology Delivers Nanoliters of Compound.

For the screen, 5,000 cells were plated per well of a gelatin coated, black 384-well plate, in 80 uL of ES media. The following day, cells were washed with PBS, and the differentiation medium was added. We chose to use a library of 50,000 kinase directed compounds that had proved fruitful in previous similar studies. Using a pintool machine (FIG. 22), 500 nl of compound was added to each well, and media was refreshed every 3 days thereafter.

Figure 23:
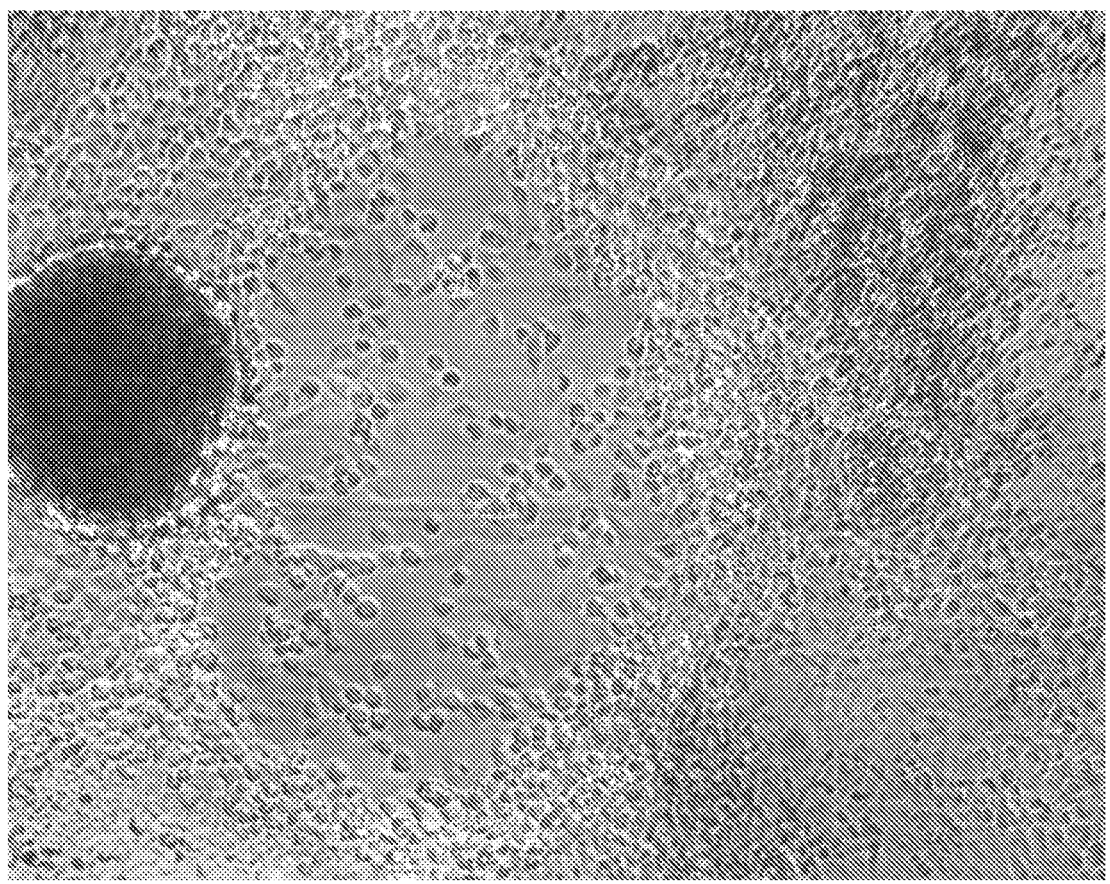
FIG. 23: A Potential Hit From MLC-2v Screen Displays Strong Fluorescence in GFP Channel.

Approximately 280 compounds displayed a significantly higher amount of signal in the GFP channel of the microscope at 15 days. Shown in FIG. 23 is a representative hit compound showing extensive signal in the GFP channel of the fluorescent microscope.

False positives and false negatives can be a significant problem in small molecule screens. False positives may include fluorescent molecules that mimic the GFP signal, random differentiation in a given well, or interaction of a small molecule with a random component of the medium. False negatives may include compounds that had their effect masked by a component of the medium. In order to screen out false positives, the initial 280 compounds were arrayed into a new 384-well plate, and the screen was repeated using these. Minutes after adding compounds, the cells were observed under the fluorescent microscope to assess possible compounds fluorescence. The 15 strongest fluorescing compounds of the original 280 were inducing fluorescence in the cells only 5 minutes after addition, indicating a false positive due to compound fluorescence. Of the rest, only 10 of these initial compounds repeated in the first follow-up, and unfortunately none of the 10 repeated in a second follow-up. We theorized that the lack of repeatable hits in this screen was due to a combination of false positives and false negatives, with the underlying problem being undefined and random media components (serum) that mask real hits, and stimulate false hits.

A Serum-Free, Monolayer Condition for Cardiomyocytes:

The most common method of inducing cardiomyogenesis of murine ES cells involves suspension culture (in the presence of serum and absence of supplemented leukemia inhibitory factor/LIF) to form aggregates (EBs), which differentiate into various cell types, including hematopoietic, endothelial, neuronal and cardiac muscle cells. Isolation of the desired cell type can be achieved through EB dissociation and FACS, followed by replating. When used in combination with specific treatments of growth factors, this has proven to be an effective, though cumbersome, method of generating cardiac cell types and has been particularly useful in the identification of cardiac precursor cells. While the differentiation protocols described above have great utility, they are still not optimal for the study of factors influencing cardiac specification. In particular, media components such as fetal bovine serum (FBS) and Knockout Serum Replacement (KO-SR) contain undefined compositions including growth factors. For example KO-SR has been shown to have bone morphogenetic protein (BMP) activity. The use of undefined media can obscure and complicate the analysis of factors affecting cardiomyocyte differentiation. Additionally, the 3-dimensional nature of the EB model of cardiomyocyte differentiation makes it difficult to obtain homogeneous populations of cells due to the presence of diffusion gradients within embryoid bodies and three-dimensional cell-cell interactions. As EB differentiation is similar to that of the developing embryo, it necessarily involves the generation of heterogeneous populations of cells. In contrast, monolayer differentiation provides a greater ability to provide a specific and uniform local concentration of growth factors.

Figure 24:
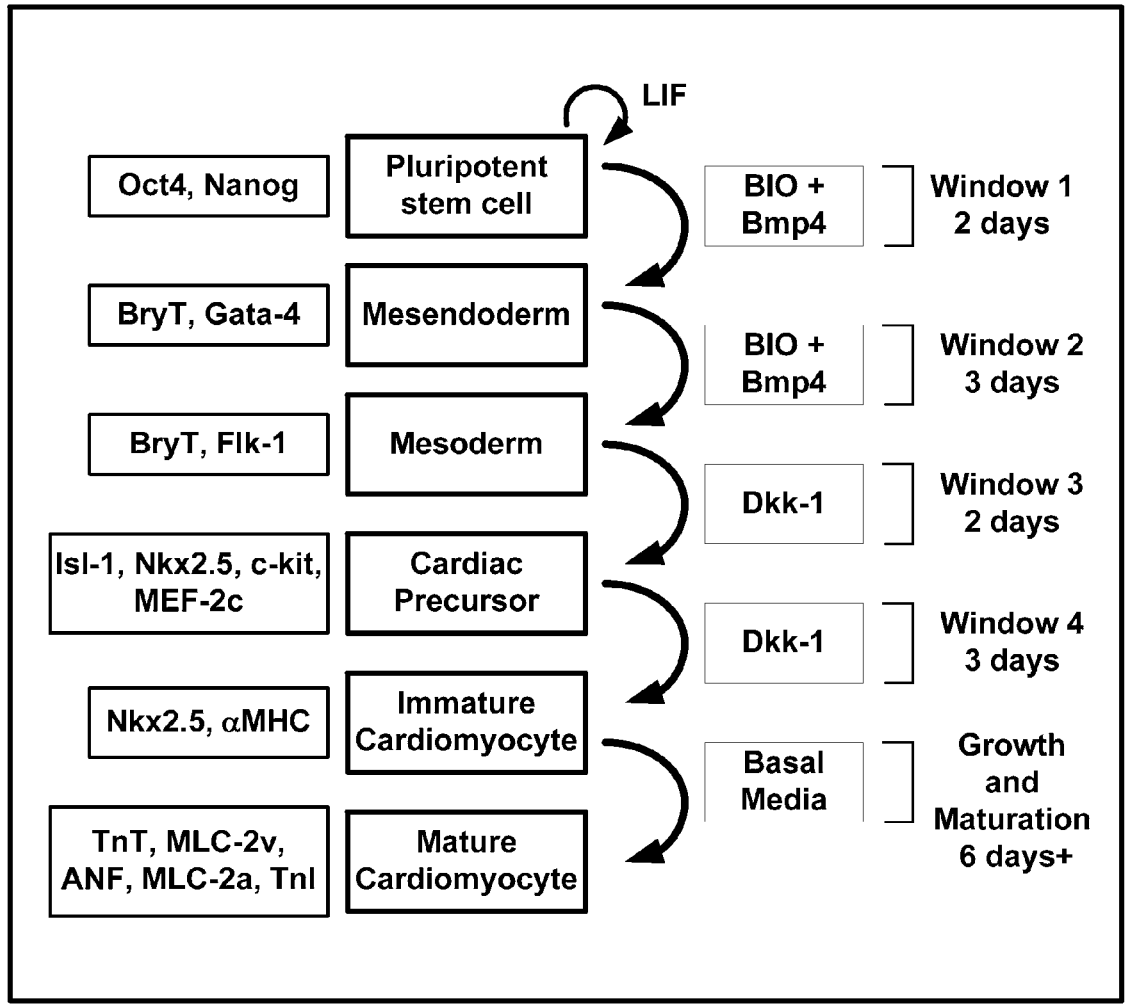
FIG. 24: Schematic for the Stepwise Differentiation of Cardiomyocytes.

Assay Development:

While cellular differentiation is a fluid process, its study can be simplified by defining stages of differentiation. In order to identify conditions conducive to cardiomyocyte differentiation, we employed a matrix strategy in which cells were differentiated for 10 days encompassing 4 treatment windows (followed by a period of maturation in the final procedure). The stages identified for the current study were mesendoderm, mesoderm, cardiac precursor, early cardiomyocyte, and mature cardiomyocyte. Shown in FIG. 24 is a schematic representing the transition from ES cells to cardiomyocytes, including markers for each cell type defined and the treatments used to stimulate each transition.

Figure 25:
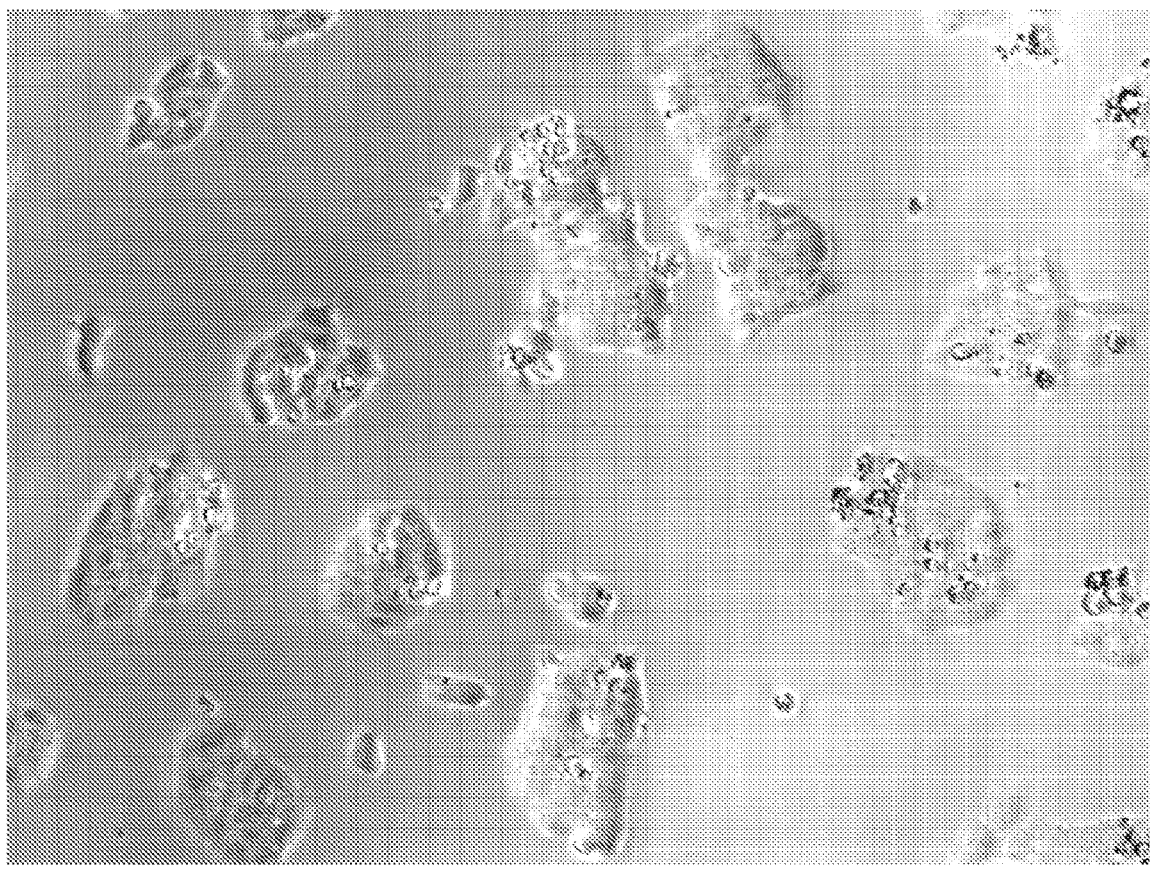
FIG. 25: Sufficient ESC Colony Size is Required for Survival in CDM.

We began by identifying a minimal serum-free condition in which approximately 1% of cells would express αMHC (alpha-myosin heavy chain) after 10 days of culture. Combinations of medium components and plate coatings were tested in parallel, with the most permissive and consistent condition being a modified chemically defined N2/B27 medium on Matrigel coated plates (see Methods). Prior to differentiation, ES cells were maintained in a pluripotent state on MEFs and with LIF. At day −1, the cells were trypsinized and replated on Matrigel coated plates in LIF supplemented medium, allowing for better cell survival and more robust initial colony formation. In one day, a sufficient colony size is achieved allowing survival in serum-free medium (FIG. 25).

Figure 26:
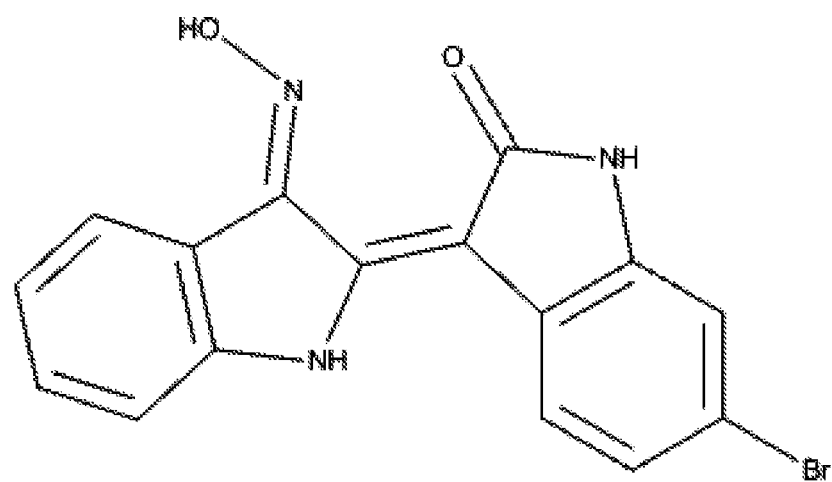
FIG. 26: Molecular Structure of GSK-3 inhibitor, 6-bromoindirubin-3'-oxime (BIO).
Figure 27:
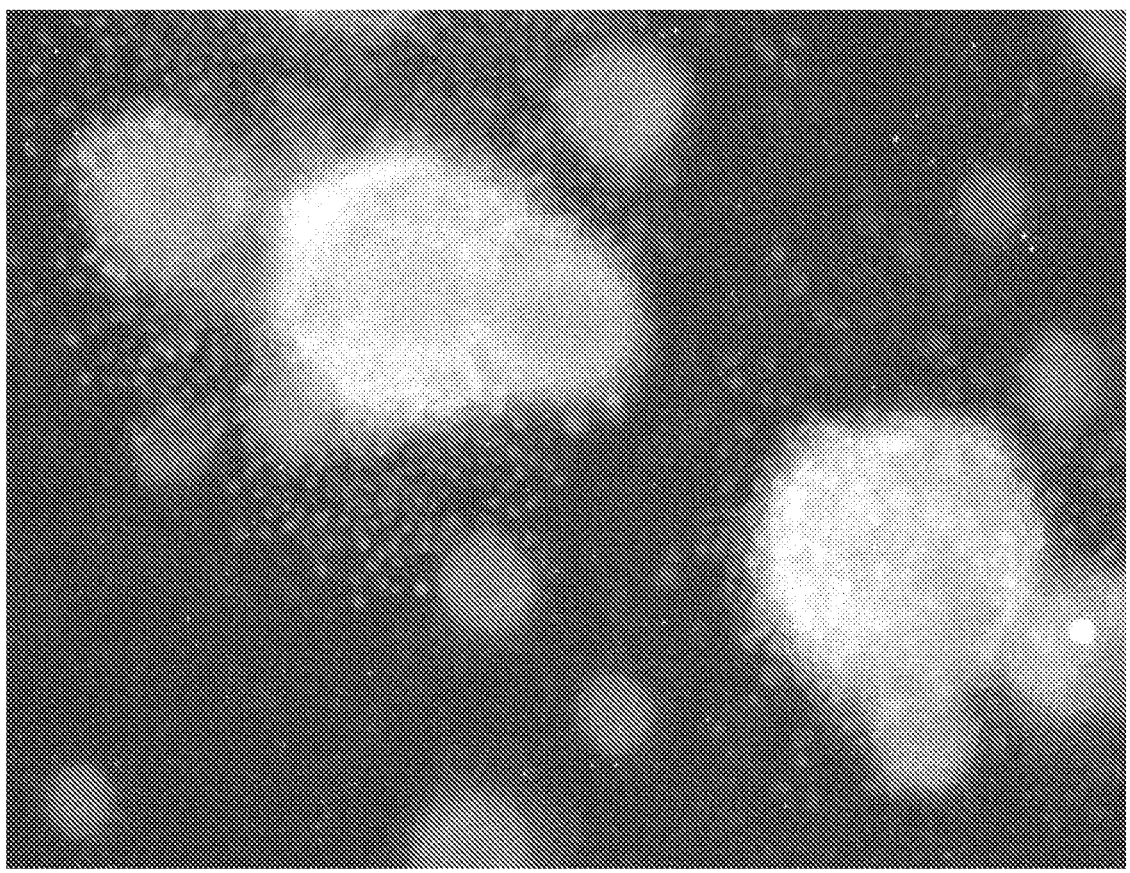
FIG. 27: BIO Induces Expression of αMHC and GATA-4.

From a literature search, we identified growth factors, cytokines and small molecules reported to influence cardiac differentiation, such as activators and inhibitors of BMP, TGF-β/Nodal, Hedgehog, Wnt, and Notch pathways and tested each for their ability to induce cardiomyogenesis at each time window. For example, to test Dkk-1 in the second window, cells were in basal medium for days 0-2, treated with Dkk-1 for days 2-5, then cultured in basal medium until day 10 before immunofluorescence scoring. Positive regulators of cardiac specification at each stage were therefore identified by their ability to induce alpha-myosin heavy chain (αMHC) expression at day 10, as assessed by immunostaining Results BMP and Wnt Stimulate Early Cardiac Differentiation Some factors had no significant effect (e.g., hedgehog), few had negative effects (e.g., Activin A), while two factors had strikingly positive effects in directing cardiac specification. The potent GSK-3 inhibitor, 6-bromoindirubin-3'-oxime (BIO) (FIG. 26), was found to increase the percentage of αMHC staining when administered in the first window (day 0-2), and to a lesser extent during the second window (day 2-5), with an optimal dosage of 4 uM. Shown in FIG. 26 is a representative image of BIO induced cardiac cells stained for alpha-MHC and GATA-4.

Figure 28:
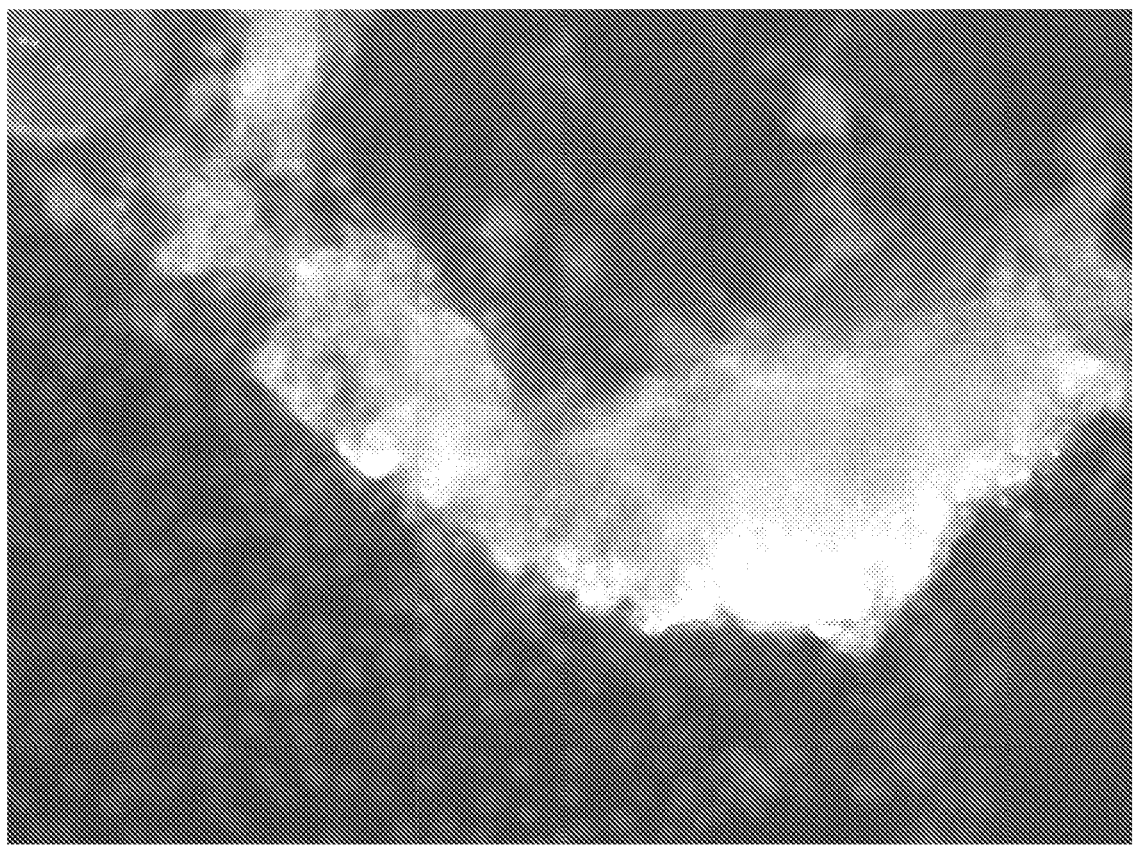
FIG. 28: BMP-4 Induces Expression of αMHC and GATA-4.

BMP-4, a member of the TGF-β superfamily, had similar effects on the percentage of αMHC positive cells when administered during the first and/or second treatment windows with an optimal concentration of 20 ng/ml. Shown in FIG. 28 is a representative image of BMP-4 induced cardiac cells stained for alpha-MHC and GATA-4.

Treatment with either BMP-4 or BIO in the first window resulted in approximately 20% of cells staining for αMHC. When the optimal treatments from these first two windows are combined into a single differentiation scheme, the cells develop and differentiate into colonies where approximately 35% of cells stain positive for MHC at day 10.

Inhibition of Wnt by Dkk-1 Stimulates Late Cardiac Differentiation

Having identified positive effectors of cardiomyogenesis in the first two windows of differentiation, we sought to reexamine our group of factors in the later stages of differentiation. In this iteration, cells were treated with a combination of BMP-4 and BIO for 5 days before being treated in the third window (day 5-7) or fourth window (day 7-10). In this case, we found that treatment with the Wnt inhibitor Dkk-1 further increased the efficiency of cardiac differentiation by 20%. Furthermore, when these colonies of cells were replated onto gelatin coated plates and maintained in a basal medium, nearly 50% developed a beating phenotype after 6 days of culture.

Time Course Analysis of Differentiation

Figure 29:
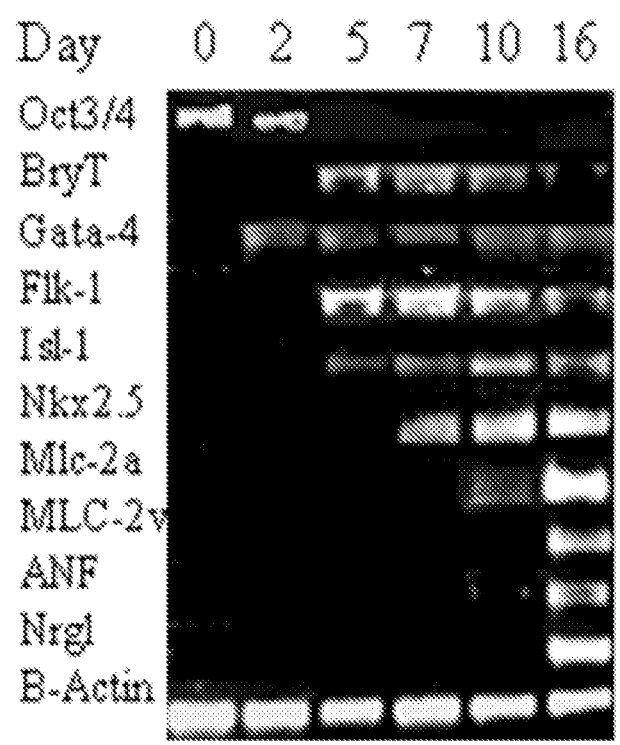
FIG. 29: RT-PCR Time Course Analysis of Differentiation.

In order to arrive at a clearer understanding of this process, we carried out immunofluorescence and RT-PCR studies of the differentiating cells. At day −1, the cells were replated onto Matrigel in LIF containing medium, and by day 0 the cells continued to express the pluripotency marker Oct-4 (FIG. 29). At this point, the self-renewal cues were removed and mesoderm specification began through simultaneous BMP and Wnt signaling. At this stage, cells began to resemble the primitive streak of the developing embryo, expressing markers such as Brachyury T and Gata-4, with Gata-4 being expressed as early as day 2 (FIG. 29) and Brachyury T being expressed as early as day 3 (FIG. 18).

Listed in Table 1 are the specific primers and conditions used for the RT-PCR studies.

TABLE 1

RT-PCR Primers and Conditions

| Gene | Sense (SEQ ID NO.:) | Antisense (SEQ ID NO.:) | Cycles | Melting T (° C.) |
|---|---|---|---|---|
| Oct3/4 | GGCGTTCTCTTTGGAAAG GTGTTC (10) | CTCGAACCACATCCTTCT CT (11) | 25 | 58 |
| BryT | CAT GTA CTC TTT CTT GCT GG (12) | GGT CTC GGG AAA GCA GTG GC (13) | 33 | 58 |
| GATA4 | TTC CTT GTC CTC ATC ACC CAC AGA (14) | GAC AA TGT TAA CGG GTT GTG GAG G (15) | 32 | 58 |
| Flk1 | GGTTCTCTGTCAAGTGGC GGTAAA (16) | AGCACACAGGCAGAAAC CAGTAGA (17) | 32 | 58 |
| Isl-1 | TGT CAG GAG ACT TGC CAC TTT (18) | GCC AAA CGT TTA TTA GTG AAA TAG TCC TG (19) | 32 | 58 |
| Nkx2.5 | ACC TTT CTC CGA TCC ATC CCA CTT (20) | GCG TTA GCG CAC TCA CTT TAA TGG (21) | 28 | 58 |

TABLE 1 -continued

RT-PCR Primers and Conditions

| Gene | Sense (SEQ ID NO.:) | Antisense (SEQ ID NO.:) | Cycles | Melting T (° C.) |
|---|---|---|---|---|
| Mlc2a | AAG GGA AGG GTC CCA TCA ACT TCA (22) | AAC AGT TGC TCT ACC TCA GCA GGA (23) | 30 | 58 |
| Mlc2v | ACT TCA CCG TGT TCC TCA CGA TGT (24) | TCC GTG GGT AAT GAT GTG GAC CAA (25) | 32 | 58 |
| ANF | TTCCTCGTCTTGGCCTTTT G (26) | CCTCATCTTCTACCGGCA TCTTC (27) | 32 | 58 |
| Nrg1 | CCA ATG GCC ACA TTG CCA ATA GGT (28) | AGC CTG GCC TGT AAT TCT TCC TGT (29) | 32 | 58 |
| β-Actin | GAA GGT GAC AGC ATT GCT TCT GTG (30) | TTG GTC TCA AGT CAG TGT AGA GGC (31) | 27 | 58 |

Figure 30:
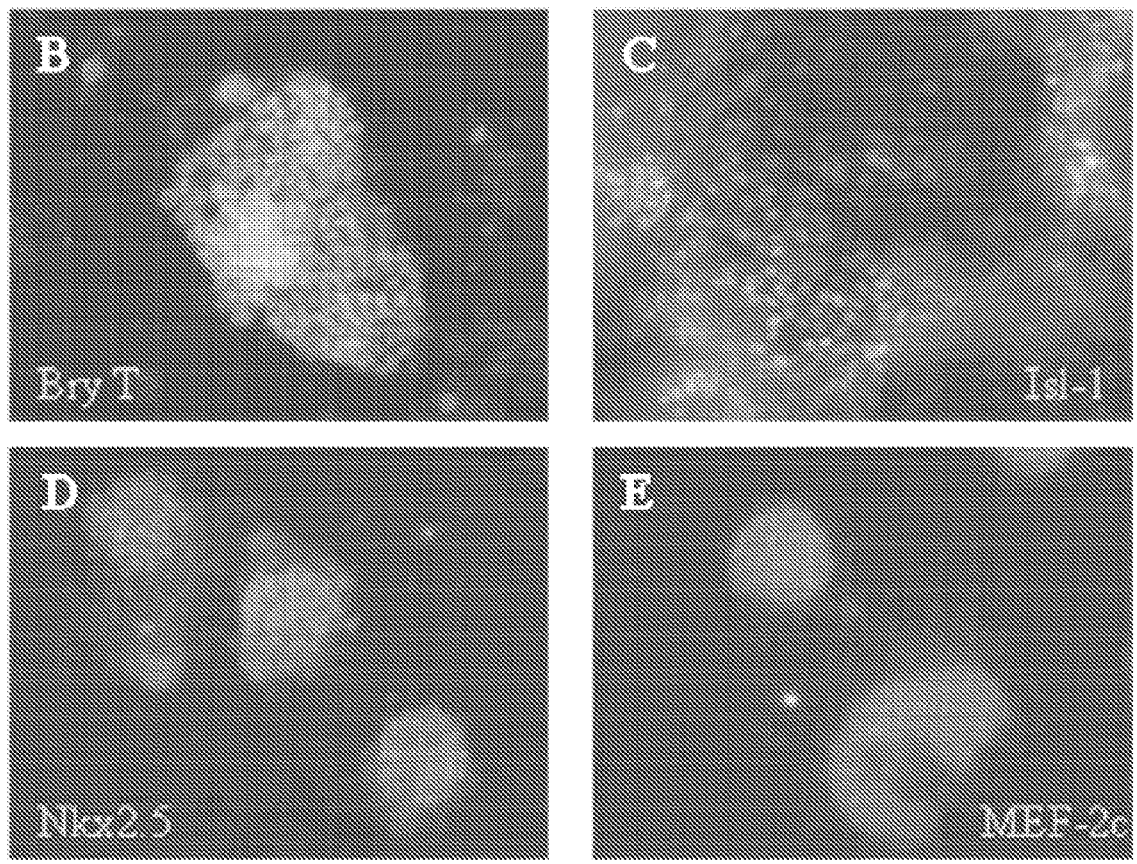
FIG. 30: Differentiating Cells Express Intermediate Markers of Cardiac Differentiation.

Continued stimulation with BMP-4 and BIO over days 2-5 further specified the cells first as mesodermal, and later more specifically as cardiac forming mesoderm, as observed by expression of Isl-1 and Flk-1 (FIG. 29). In the third window of treatment, BMP-4 and BIO were replaced by Dkk-1, and Isl-1 expression increased (FIGS. 29, 30C) and Nkx2.5 (FIGS. 29, 30D) and MEF-2c (FIGS. 29, 30E) are expressed. After a total of 5 days of treatment with Dkk-1, the first markers of mature cardiomyocytes began to be expressed (FIG. 29).

Figure 31:
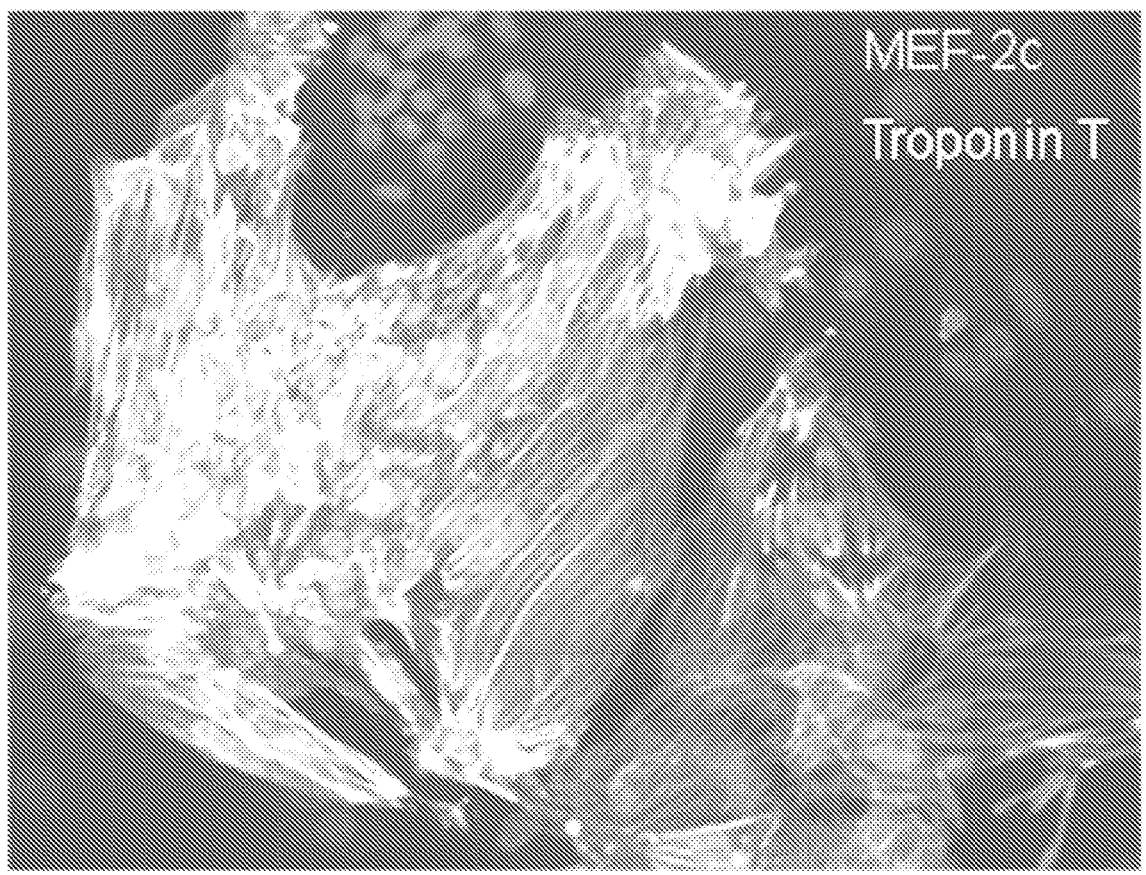
FIG. 31: Beating Cells Express Markers of Mature Cardiomyocytes.
Figure 32:
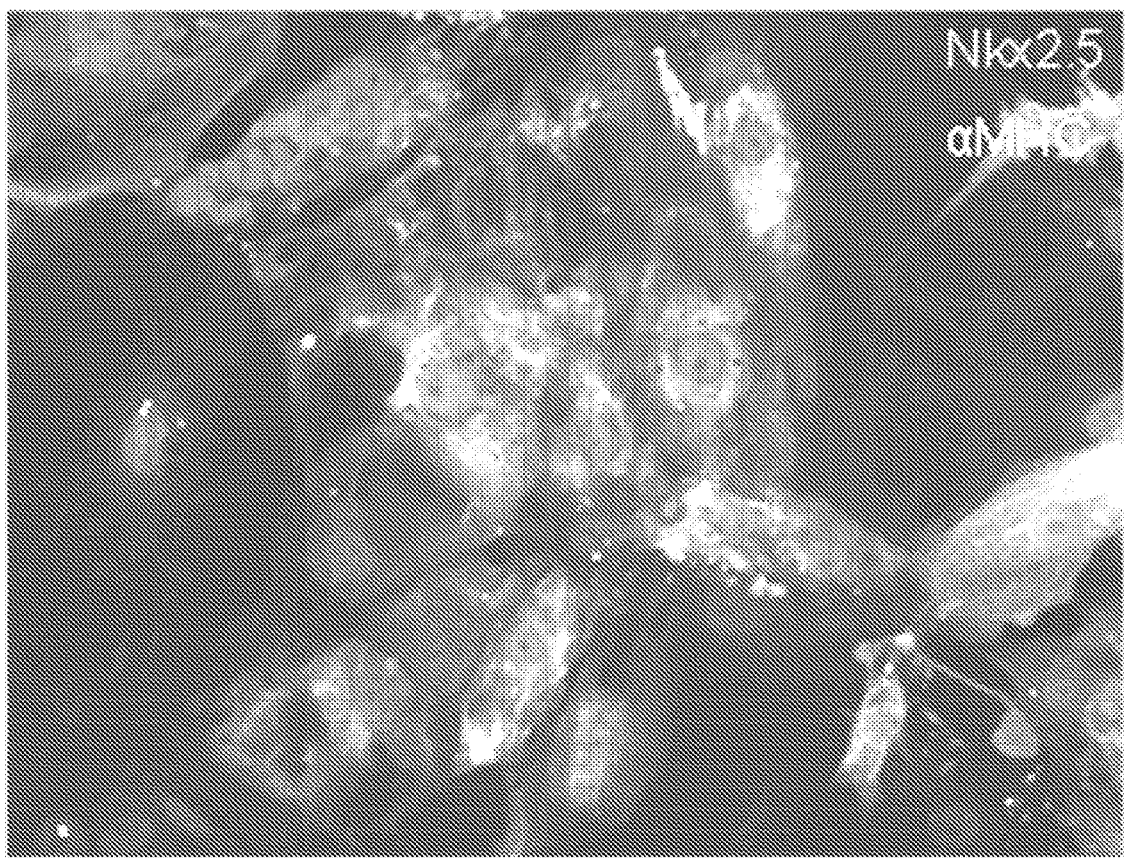
FIG. 32: Beating Cells Express Markers of Mature Cardiomyocytes.

At this point, we found further maturation was facilitated by replating the cells onto gelatin coated plates in basal medium, without using additional growth factors. Colonies of cells began to spontaneously contract after approximately 6 days and express cardiac specific genes such as Troponin T, αMHC, and MLC-2v (FIGS. 29, 31, and 32).

We determined that contracting cardiomyocytes could subsequently be maintained in serum-free medium for over one month.

A Small-scale Screen in a Serum-free, Monolayer Condition

Having identified the first serum-free monolayer condition for cardiac differentiation of ES cells, we sought to test its efficacy as a platform to discover regulators of cardiomyogenesis. A collection of approximately 200 small molecules and growth factors reported to be influential in developmental processes were assembled. R1 ES cells were grown and plated for differentiation on Matrigel in 24-well plates using the media and growth factors described above. The screening collection was then added and removed from each well at specific time points in order to account for different developmental time windows. The collection was screened at days 0-2, 2-5, and 5-7.

Calcium Signaling Stimulates Mesodermal Differentiation

Figure 33:
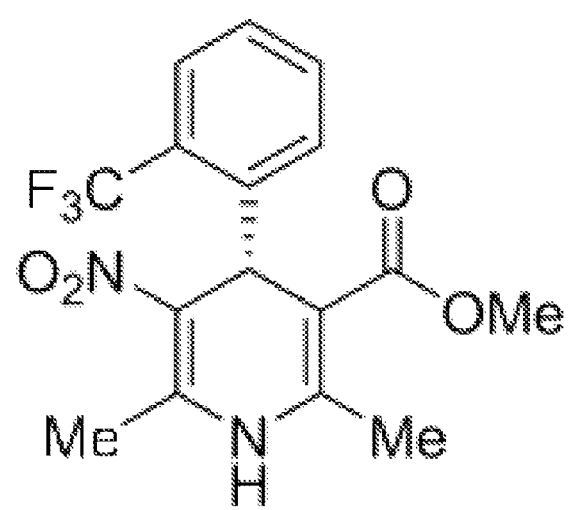
FIG. 33: Molecular Structure of BayK 8644.

A strong positive stimulator of cardiac differentiation was found to be the L-type Calcium channel (LTCC) agonist BayK 8644 (FIG. 33). Calcium signaling is involved in several developmentally important signaling pathways. In regards to mesoderm formation and patterning, gradients of intracellular $Ca^{2+}$ and inositol-1,4,5-trisphosptate (Ins(1,4,5) $P_3$) have been suggested to play a role in formation of the dorsal-ventral (D-V) axis of the embryo.

The members of the Wnt-1 class signal through the canonical Wnt/beta-catenin signaling pathway, in which a stabilization of cytoplasmic beta-catenin allows beta-catenin to regulate gene expression in the nucleus. Conversely, members of the Wnt-5A class, stimulate the release of intracellular $Ca^{2+}$ and activate two $Ca^{2+}$-sensitive enzymes—$Ca^{2+}$/calmodulin-dependent protein kinase II (CamKII) and protein kinase C (PKC)—in a G-protein-dependent, but β-catenin-independent, manner. This pathway is commonly referred to as the Wnt/$Ca^{2+}$ pathway, or non-canonical Wnt signaling, as Calcium is thought to stimulate CamKII and PKC.

To further ascertain the mechanisms by which calcium might be stimulating cardiac differentiation, growth factors and small molecules in related pathways were tested. As stated, non-canonical Wnt signaling is dependent upon calcium. The model of differentiation proposed, however, states that canonical Wnt signaling is required at the early stages differentiation. As canonical and non-canonical Wnt signaling are generally opposing signals, it is unlikely that calcium was operating in the non-canonical pathway here. Nonetheless, Wnt5a was tested for its ability to stimulate cardiac differentiation at the same stage as BayK 8644, both in conjunction with Bmp-4 and BIO and alone. Wnt5a treatment resulted in a 20% decrease in overall beating efficiency in the differentiation, possibly by interfering with canonical Wnt signaling.

Figure 34:
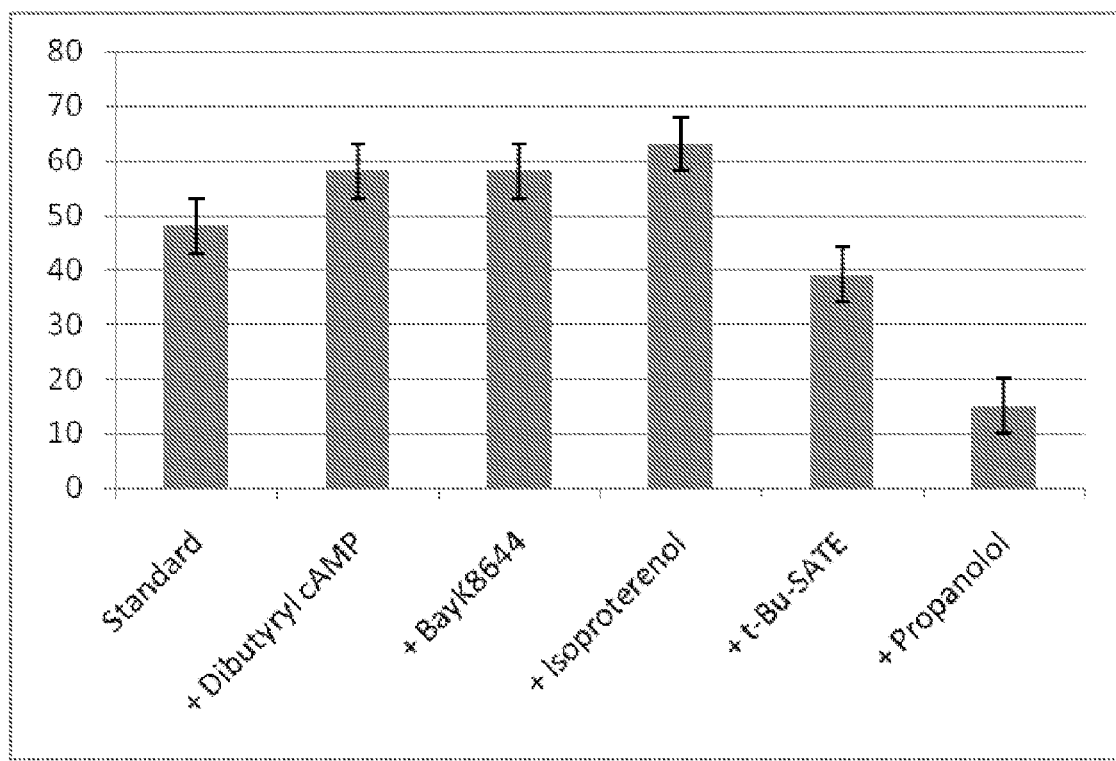
FIG. 34: Percentage of Beating Colonies.

To clarify that the effect seen with BayK 8644 was indeed mediated by calcium, several beta adrenergic regulating compounds were tested. Beta adrenergic receptors interact with G-proteins that contain the Galphas (Gs) and Galphai (Gi) subunits. The Galphas and Gbetagamma subunits positively regulate L-type $Ca^{2+}$ channels. Additionally, several isoforms of adenylate (adenylyl)cyclases are activated by Galphas subunits and as such, activation of b-adrenergic receptors typically can elevate levels of cyclic AMP (cAMP). Interestingly, the Gs activator isoproterenol displayed an even more potent cardiac inducing effect than BayK 8644, while the beta blocker propranolol greatly decreased cardiac potential. To test whether the calcium effect might be explained by cAMP levels, we tested an inhibitor of adenylyl cyclase 2',5'-dd-3'-AMP-bis(t-Bu-SATE) and saw a decrease in the percentage of beating clusters. Additionally, the stable cAMP analog dibutyryl cAMP, often used to stimulate PKA/PKC signaling, increased the percentage of beating colonies (FIG. 34).

Figure 35:
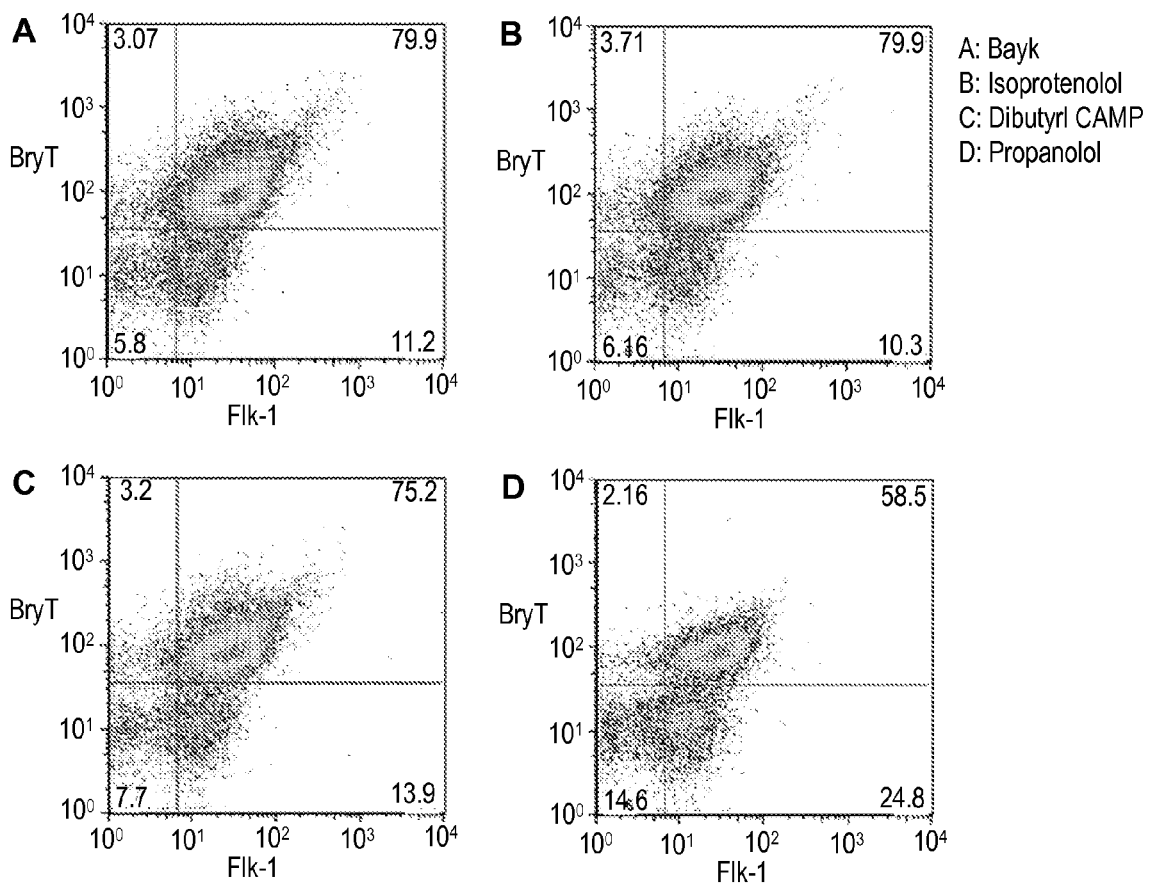
FIG. 35: FACS Analysis of Mesodermal Markers. Cells were treated with the small molecule BayK 8644 (A), isoprotenolol (B), dibutyrl cAMP (C), or propanolol (D) and Brachyury expression was measured.

To ascertain what role calcium and cAMP might be playing in this early stage of cardiac differentiation, FACS was carried out using two markers involved in mesodermal fates. Specifically, a Brachyury-EGFP ES cell (a gift from the Keller lab) was used to identify cells progressing to a primitive streak type population. Further, cells were stained using a Flk-1 antibody to further delineate axial location of the primitive streak type cells. Briefly, cells were treated with small molecules for day 0-2, and harvested at day 4.5 for analysis. As seen in the FACS plots (FIG. 35), the tested compounds had less of an effect on Brachyury-GFP expression, and more of an effect on Flk-1 expression. BayK8644, isoproterenol, and dibutyryl cAMP all displayed a similar increase in the portion of GFP+ cells that were also positive for Flk-1, whereas propanolol decreased the percentage Flk-1 positive cells. These results indicate that calcium and cAMP signaling is helping to further specify the differentiation to a subset of the primitive streak that is cardiogenic (Flk-1+).

To further analyze the mechanism of action of the cardiogenic effect seen with these molecules, QRT-PCR was carried out on cells treated from day 0-2 and harvested at day 4.5.

Figure 36:
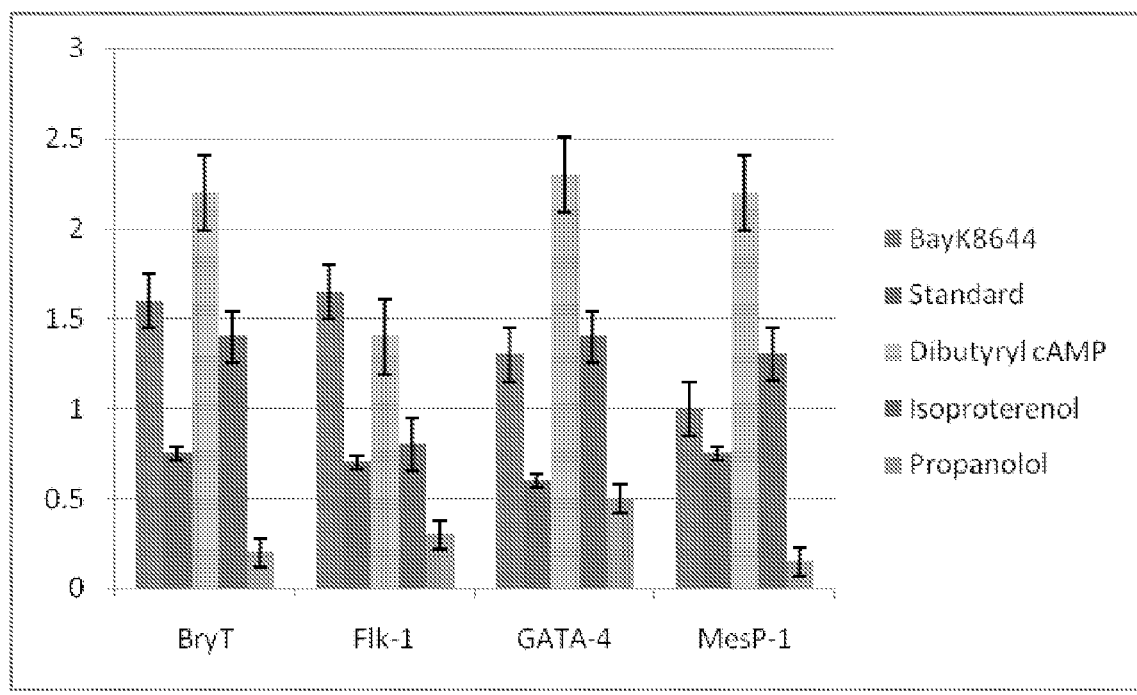
FIG. 36: QRT-pCR Analysis of Markers. Normalized fold expression of markers was measured for cells treated with BayK 8644, dibutyrl cAMP, isoprotenolol, or propanolol.

As seen in the expression analysis (FIG. 36), BayK8644, dibutyryl cAMP and isoproterenol all increased expression of Brachyury T, Flk-1, GATA-4 and MESP1.

GATA-4 is a GATA family zinc-finger transcription factor that interacts with cardiac transcription factors Nkx2.5, Tbx5, and HAND2 and its expression is slightly earlier than that of Nkx2.5, though it is not completely specific for cardiac fates. The Mesp1 gene encodes the basic HLH protein MesP1 which is expressed in the mesodermal cell lineage during early gastrulation. Disruption of the Mesp1 gene leads to aberrant heart morphogenesis, resulting in cardia bifida. MesP1 is expressed in the heart tube precursor cells and is required for mesodermal cells to depart from the primitive streak and to generate a single heart tube. Flk-1 is a receptor for vascular endothelial growth factor (VEGF) and marks both cardiac and hematopoietic precursors that arise from the primitive streak.

A TGF-beta Inhibitor Stimulates Cardiac Differentiation in Later Stages of Development The transforming growth factor (TGF)-beta superfamily is a diverse group of cytokines that have pleiotropic effects in numerous biological processes. TGF-beta signaling is achieved via heteromeric complexes of both type I and type II serine/threonine kinase receptors. Upon binding of the TGF-beta ligand and heterodimerization, the type I receptor is phosphorylated by the type II receptor which activates a signal transduction cascade involving the Smad pathways. The superfamily members are classified into 2 categories: TGF-beta/Activin/Nodal, and BMP/GDF. The TGF-beta/Activin/Nodal group activates Activin receptor-like kinase (ALK) 4, 5, and 7, which phosphorylate Smad2 and 3, while the BMP/GDF group activates ALK 1, 2, 3, and 6, which in turn phosphorylate Smad1, 5, and 8.

Figure 37:
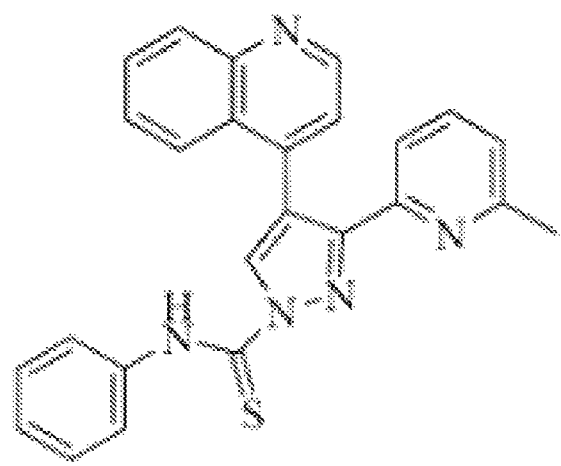
FIG. 37: Molecular Structure of TGF-beta Inhibitor, A83-01.

TGF-beta signaling is thought to be essential to the development of mesoderm, in particular to the induction of the primitive streak. In in vitro studies, the Keller group demonstrated dramatic reduction in cardiac differentiation when EBs were treated with the TGF-beta inhibitor SB431542. Additionally, as the primitive streak migrates inward in the developing embryo, the cells undergo EMT, enabling their motility; EMT is stimulated by TGF-beta signaling. Interestingly, we found that treatment with the TGF-beta inhibitor A83-01 (FIG. 37) actually induced a higher number of beating colonies when used in days 5 though 7 of the differentiation program. A83-01 is selective for the ALK4, 5, and 7 receptors, and is more specific than SB431542.

Figure 38:
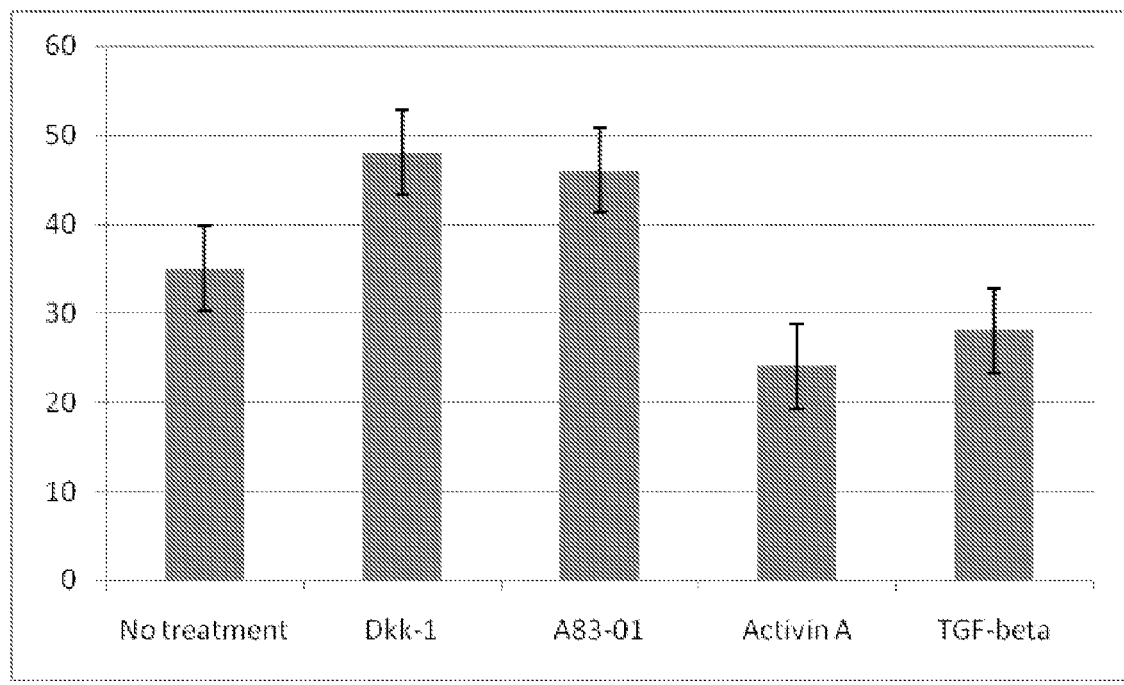
FIG. 38: Percentage Beating Colonies Observed After Treatment in Days 5-7.

To further demonstrate that inhibition of Activin/Nodal/TGF-beta signaling is playing a role in cardiac determination, the growth factors Activin and TGF-beta were tested. As expected, treatment with these growth factors resulted in a lower number of beating colonies, as is shown in FIG. 38.

Figure 39:
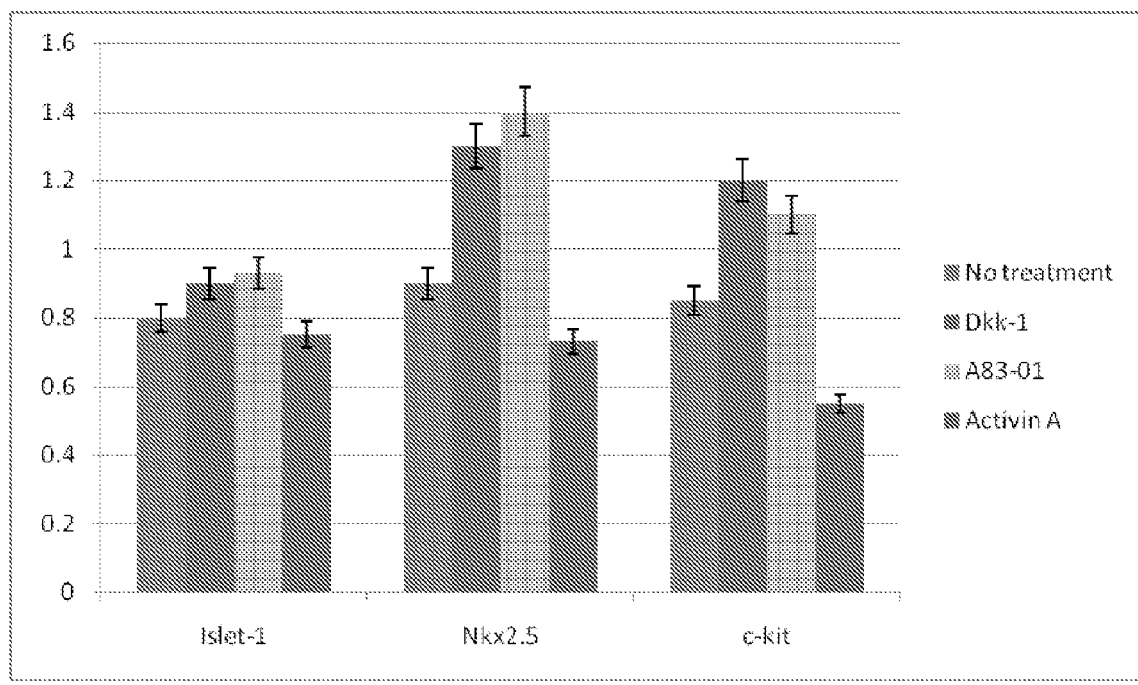
FIG. 39: QRT-PCR After Treatments in Days 5-7.

QRT-PCR was carried out to observe the induction of cardiomyogenesis at the transcript level. At day 5, when A83-01 treatment begins, the predominant state is that of a developed primitive streak type population that is yet to display robust expression of markers of cardiac precursors such as Nkx2.5, Isl-1, and c-kit. As can be seen in FIG. 39, treatment with A83-01 from days 5-7 induced higher levels of expression of cardiac specific markers when assessed at day 8, whereas treatment with Activin A had the opposite effect.

Discussion

The model of cardiomyocyte differentiation we propose is therefore most simply modeled as involving 4 phases of differentiation, followed by a period of maturation. At the earliest stages, both BMP-4 and Wnt alone can specify ES cells towards mesendodermal and mesodermal lineages. When both pathways are activated concomitantly, the differentiation becomes more specific to a subset of cardiac forming mesoderm. β-catenin induces mesoderm formation through Brachyury T expression, and BMP-4/Smad1 is also thought to induce mesoderm, thought its mechanism is unclear.

Continued BMP and Wnt signaling into the second phase of differentiation aids in specification of the cardiac fate through direct promotion of cardiac precursor genes. The downstream pathway components of BMP-4, Smad1/4 activate Nkx2.5 expression through direct binding of its promoter. Similarly, canonical Wnt signaling has been shown to induce dorsal mesoderm formation and promote formation of cardiac precursors by directly regulating expression of the cardiac precursor gene, islet-1. At the onset of the third stage of differentiation, the earliest markers of cardiac precursors are just beginning to be expressed. Specification of cardiac precursors from this mixture of mesodermal cells was achieved when the Wnt inhibitor Dkk-1 was used.

After continued stimulation with Dkk-1 in the fourth stage of differentiation the cells begin to express mature cardiomyocyte markers and form tight colonies that are resistant to trypsin mediated dissociation. We observed an increased efficiency in cardiac maturation when these colonies were detached and replated at a lower density on gelatin coated dishes, while being maintained in basal medium.

Though numerous growth factors have been implicated in cardiomyogenesis, we have found a minimal signaling requirement for cardiac specification that is remarkably simple. Our results indicate that BMP and Wnt signaling sit high in the order of mesodermal and subsequent cardiac specification and that inhibition of Wnt signaling is important in later stages of differentiation. It is inevitable that the regulation of more pathways is involved in specification of the cardiac lineages; the chemically defined, monolayer condition described herein should prove an excellent tool in the pursuit of these factors.

While calcium/cAMP signaling is important in various differentiation programs, its particular importance in the specification of cardiogenic mesoderm was previously unknown. This phase of differentiation coincides with the inward movement of gastrulation which naturally involves an increase in calcium concentrations. However, the only role calcium was thought to play was in the motility and morphogenic changes that occur during gastrulation. In our studies, it was demonstrated that calcium also plays a signaling role in a cAMP pathway to direct cells toward a cardiogenic mesodermal fate.

While monolayer conditions for the differentiation of neural and endoderm derivatives have been described, to our knowledge, similar success has yet to be achieved in cardiac differentiation. Use of a similar basal differentiation condition should facilitate comparisons of different ESC derived populations. Previously, BIO and BMP-4 have been reported to stimulate self-renewal of mESCs. In this study, a novel cardiac mesoderm induction effect of BIO on ESCs was identified, and a strong positive role for BMP-4 in cardiac mesoderm formation was observed. Clearly, the effect of these molecules is contextually dependent upon factors such as the composition of signaling molecules in the medium and the extracellular matrix. As such, the present study highlights the value of the serum-free and monolayer approach to the study of ESC differentiation. Additional analyses of the regulation of cardiomyogenesis should be facilitated by use of the described system as the lack of undefined medium components should prove to produce more reliable and consistent results. Similarly, the use of a monolayer differentiation procedure allows for finer tuned mimics of the in vivo development process.

Methods

Knock-in ESC generation: R1 ES cells were grown on feeder layer to near confluency, tryspinized, resuspended in 0.2-0.5 ml PBS, and transferred to an electroporation cuvette with 0.4 cm gap. The linearized targeting construct (25-60 ug) was added to the cuvette and briefly mixed by pipette and placed on ice for minutes before electroporation. A BioRad Gene Pulser II was used at max capacitance and 500V. The cuvette was immediately iced for 10 minutes. The mixture was resuspended in warm ES media, and plated on feeder layer (1 6-well plate). The following day, media was changed and selection began with 0.1 ug/ml puromycin. When colonies became clearly visible to the naked eye, approximately one week later, colonies were picked. Colonies exhibiting round colony shape and distinct borders were picked using a 200 ul pipette, containing 30 ul trypsin, and transferred into 96 well plates. Cells were then split into 96-well plates for freezing, and 24-well plates for DNA harvesting. DNA was harvested by adding sarcosyl lysis buffer and incubating overnight. The lysis was transferred into tubes containing 5 ul of proteinase K and mixed. Tubes were then filled EtOH and mixed until precipitate formed and centrifuged for 2 minutes at maximum speed. The supernatant was removed and another 500 uL of 70% EtOH was added and vortexed. After another 5 minute centrifuge at max rpm, the supernatant was removed and the tubes were allowed to air dry, before resuspending the pellet in 125 ul water.

A primer set specific for the Nkx2.5 promoter and the GFP insert were designed to be used to test for correct integration of the vector. PCR reactions were run for all 500 clones generated, with 10 of the clones showing the correct PCR product size on an electrophoresis gel. The 10 cell lines with the correct GFP insertion into the Nkx2.5 locus were expanded for testing. Hanging drop embryoid bodies were generated for each cell line and monitored daily for GFP expression.

Embryonic stem cell maintenance: All reagents are from Invitrogen unless otherwise stated. R1 mESCs are cultured on 0.1% gelatin-coated dishes with irradiated MEF (CF-1) cells in growth medium (ESGM). ESGM contains Knockout DMEM, 15% KO-Serum Replacement, 1×L-Glutamax, 1 mM beta-mercaptoethanol, 1× non-essential amino acids, 1× nucleosides, and 1000 U/ml LIF (Millipore). All reagents are from Invitrogen unless otherwise stated. Prior to differentiation, cells were passaged once on low-density MEF.

Cardiac differentiation: Cells are plated at a density of 200,000 cells/well of a 6-well plate in 2.5 ml of ESGM. 6-well plates are coated overnight at 4° C. with 1 ml of Matrigel (BD Bioscience) diluted 50× from stock concentration. 24 hours after plating, or after sufficient colony size was achieved, cells are switched into chemically defined medium (CDM) and treated with 4 uM BIO (Calbiochem) and 20 ng/ml BMP-4 (R&D). CDM contains RPMI 1640, 0.5×N2, 1×B27 (without Vitamin A), 0.5× Glutamax, 0.55 mM beta-mercaptoethanol, 1× non-essential amino acids, 1× nucleosides. At Day 2, medium is changed, and again CDM containing 4 uM BIO with 20 ng/ml BMP-4 is added to the cells. At Day 5, cells are washed once with PBS and medium is changed to CDM containing 100 ng/ml Dkk-1 (R&D). At Day 7, medium is changed, and again CDM containing 100 ng/ml Dkk-1 is added to the cells. At Day 10, cells are trypsinized (0.05% trypsin) (Approximately 5 minutes at 37° C., or until cells begin to detach) and replated onto gelatin coated 6-well plates in CDM with no additional growth factors. By this time, the cells will have formed tight colonies that will be difficult to disrupt (Supplementary FIG. 2b). If the cells do not detach with trypsin alone, a cell scraper can be used. The trypsin is used primarily to detach the cells rather than to dissociate them to a single cell suspension. It is preferable for the colonies to remain intact. The trypsin is briefly quenched with MEF media, cells are centrifuged, and resuspended in CDM for plating. Medium is refreshed as needed to remove dead cells and debris (every 1 to 2 days).

Immunofluorescence: Cells were fixed in 4% paraformaldehyde (Sigma) for 15 minutes, and stained in 0.3% Triton (Sigma) containing 5% donkey serum (Jackson ImmunoResearch). Antibodies were used at dilutions of MF20 [Developmental Studies Hybridoma Bank (DSHB)] 1:100, CT3 (DSHB) 1:100, Nkx2.5 (Santa Cruz) 1:200, MEF-2c (Santa Cruz), Islet-1 (DSHB) 1:100, and Brachyury T (Santa Cruz) 1:200. Secondary antibodies (Jackson ImmunoResearch) were used at 1:200 for Cy2 and 1:500 for Cy3. Nuclei are stained with DAPI (Sigma).

FACS analysis: Cells were harvested into a single cell suspension by treatment with 0.05% trypsin, quenched with serum containing medium, and resuspended in FACS buffer: 1×PBS ($Ca/Mg^{2+}$ free), 1 mM EDTA, 25 mM HEPES pH 7.0, 1% Fetal Bovine Serum. Cells were then filtered with 0.2 μm filter, and stored at 4° C. until analysis.

qRT-PCR: Total RNA from each sample was prepared from $5 \times 10^4$ cells using RNeasy mini kit (Qiagen). Reverse transcription was carried out by using Reverse Transcription System (Promega) and PCR performed using PCR Super Mix (Invitrogen).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of converting an animal cell from a first non-pluripotent cell fate to a second non-pluripotent cell fate, the method comprising:
   (a) introducing a polynucleotide encoding an Oct4 polypeptide, and optionally one or more reprogramming factors comprising polynucleotides encoding a Klf4 polypeptide, a Sox2 polypeptide, or a c-Myc polypeptide, into a first non-pluripotent cell, or
   contacting a first non-pluripotent cell with an Oct4 polypeptide, and optionally one or more reprogramming factors comprising a Klf4 polypeptide, a Sox2 polypeptide, or a c-Myc polypeptide,
   (b) limiting the expression of endogenous Nanog in the cells from step (a) to a level substantially lower than the level of expression of endogenous Nanog in an induced pluripotent cell (iPSC), thereby generating a non-pluripotent intermediate cell and
   (c) inducing differentiation of the cell under conditions to generate a cell having a second non-pluripotent cell fate.

2. The method of claim 1, wherein step (b) further comprises contacting the non-pluripotent intermediate cell with a JAK inhibitor.

3. The method of claim 1, wherein step (b) comprises eliminating exogenous LIF.

4. The method of claim 1, wherein the first non-pluripotent cell is a fibroblast or a neural precursor cell.

5. The method of claim 1, wherein the method is conducted in vitro.

6. The method of claim 1, wherein the non-pluripotent intermediate cell is not capable of forming a teratoma.

7. The method of claim 1, wherein polynucleotides encoding an Oct4 polypeptide, a Klf4 polypeptide, and a Sox2 polypeptide are introduced into the first non-pluripotent cell or wherein the first non-pluripotent cell is contacted with an Oct4 polypeptide, a Klf4 polypeptide, and a Sox2 polypeptide.

8. The method of claim 1, wherein polynucleotides encoding an Oct4 polypeptide, a Klf4 polypeptide, a Sox2 polypeptide, and a c-Myc polypeptide are introduced into the first non-pluripotent cell or wherein the first non-pluripotent cell is contacted with an Oct4 polypeptide, a Klf4 polypeptide, a Sox2 polypeptide, and a c-Myc polypeptide.

9. The method of claim 1, wherein the cell having the second non-pluripotent cell fate is a cell of mesodermal lineage, a cell of ectodermal lineage, or a cell of endodermal lineage.

10. The method of claim 9, wherein inducing differentiation of the non-pluripotent intermediate cell to the cell having the second non-pluripotent cell fate comprises contacting the non-pluripotent intermediate cell with BMP4, a calcium channel agonist, a Gαs activating agent, a cAMP analog, and/or a GSK-3 inhibitor.

11. The method of claim 9, wherein the cell of the mesodermal lineage is a cardiomyocyte, the cell of the ectodermal lineage is a neuronal cell, or the cell of the endodermal lineage is a pancreatic cell.

12. A method of differentiating an animal cell into a cardiomyocyte, the method comprising:
    (a) generating a non-pluripotent intermediate cell by (i) introducing a first non-pluripotent animal cell having a first non-pluripotent cell fate a polynucleotide encoding Oct4, and optionally, one more reprogramming factors comprising polynucleotides encoding a Klf4 polypeptide, a Sox2 polypeptide, or a c-Myc polypeptide; or (ii) contacting a first non-pluripotent animal cell having a first non-pluripotent cell fate with Oct4, and optionally, one or more reprogramming factors comprising a Klf4 polypeptide, a Sox2 polypeptide, or a c-Myc polypeptide;
    (b) limiting the expression of endogenous Nanog in the cells from step (a) to a level substantially lower than the level of expression of endogenous Nanog in an induced pluripotent cell (iPSC), thereby generating a non-pluripotent intermediate cell; and
    (c) contacting the non-pluripotent intermediate cell with a GSK-3 inhibitor and/or a BMP protein under conditions sufficient to generate a cardiomyocyte.

13. The method of claim 12, wherein the animal cell is a human cell.

14. The method of claim 12, wherein the method is conducted in vitro.

15. A method of transdifferentiating an animal cell into a cardiomyocyte, comprising:
    (a) introducing into a first non-pluripotent animal cell having a first non-pluripotent cell fate a polynucleotide encoding Oct4, and optionally, one or more reprogramming factors comprising polynucleotides encoding a Klf4 polypeptide, a Sox2 polypeptide, or a c-Myc polypeptide; or contacting a non-pluripotent animal cell having a first non-pluripotent cell fate with an Oct4 polypeptide, and optionally, one or more reprogramming factors comprising a Klf4 polypeptide, a Sox2 polypeptide, or a c-Myc polypeptide;
    (b) limiting the expression of endogenous Nanog in the cells from step (a) to a level substantially lower than the level of expression of endogenous Nanog in an induced pluripotent cell (iPSC), thereby generating a non-pluripotent intermediate cell; and
    (c) contacting the non-pluripotent intermediate cell with a GSK-3 inhibitor, a calcium channel agonist, a Gαs activating agent, a cAMP analog, and/or a BMP protein under conditions to generate the cardiomyocyte;
    thereby differentiating the non-pluripotent intermediate cell into the cardiomyocyte.

16. The method of claim 15, wherein the method further comprises contacting the first non-pluripotent animal cell with a JAK inhibitor.

17. The method of claim 16, wherein the first non-pluripotent animal cell is contacted with the JAK inhibitor prior to contacting the first non-pluripotent animal cell with the GSK-3 inhibitor, the calcium channel agonist, the Gαs activating agent, the cAMP analog, and/or the BMP protein.

18. A method of transdifferentiating an animal cell into a neural progenitor cell, the method comprising:
    (a) introducing into a non-pluripotent animal cell having a first non-pluripotent cell fate a polynucleotide encoding an Oct4 polypeptide, and optionally, one or more polynucleotides encoding one or more polypeptides selected from the group consisting of a Klf4 polypeptide, a Sox2 polypeptide and a c-Myc polypeptide; or contacting a non-pluripotent animal cell having a first non-pluripotent cell fate with an Oct4 polypeptide, and optionally, one or more polypeptides selected from the group consisting of a Klf4 polypeptide, a Sox2 polypeptide and a c-Myc polypeptide;
    (b) limiting the expression of endogenous Nanog in the cells from step (a) to a level substantially lower than the level of expression of endogenous Nanog in an induced pluripotent cell (iPSC), thereby generating a non-pluripotent intermediate cell; and
    (c) contacting the non-pluripotent intermediate cell with FGF2, FGF4, and EGF under conditions to generate the neural progenitor cell;
    thereby differentiating the non-pluripotent animal cell into the neural progenitor cell.

19. The method of claim 18, wherein the method further comprises contacting the non-pluripotent animal cell with a Wnt inhibitor, a JAK inhibitor, or both a Wnt inhibitor and a JAK inhibitor.

20. The method of claim 19, wherein the non-pluripotent animal cell is contacted with the Wnt inhibitor, the JAK inhibitor, or both the Wnt inhibitor and the JAK inhibitor prior to contacting the cell with FGF2, FGF4, and EGF.

21. A method of transdifferentiating an animal cell into an induced definitive endoderm (iDE) cell, the method comprising:
    (a) introducing into a non-pluripotent animal cell having a first non-pluripotent cell fate a polynucleotide encoding an Oct4 polypeptide, and optionally, one or more polynucleotides encoding one or more polypeptides selected from the group consisting of a Klf4 polypeptide, a Sox2 polypeptide and a c-Myc polypeptide; or contacting a non-pluripotent animal cell having a first non-pluripotent cell fate with an Oct4 polypeptide, and optionally, one or more polypeptides selected from the group consisting of a Klf4 polypeptide, a Sox2 polypeptide and a c-Myc polypeptide;
    (b) limiting the expression of endogenous Nanog in the cells from step (a) to a level substantially lower than the level of expression of endogenous Nanog in an induced pluripotent cell (iPSC), thereby generating a non-pluripotent intermediate cell; and
    (c) contacting the non-pluripotent intermediate cell with a GSK-3 inhibitor, an HDAC inhibitor, and a TGFβ/Activin/Nodal family member under conditions to generate the iDE cell;
    thereby differentiating the non-pluripotent animal cell into the iDE cell.

22. A method of transdifferentiating an animal cell into a pancreatic beta cell, the method comprising:
    (a) introducing into a non-pluripotent animal cell having a first non-pluripotent cell fate a polynucleotide encoding an Oct4 polypeptide, and optionally, one or more polynucleotides encoding one or more polypeptides selected from the group consisting of a Klf4 polypeptide, a Sox2 polypeptide and a c-Myc polypeptide; or contacting a non-pluripotent animal cell having a first non-pluripotent cell fate with an Oct4 polypeptide, and optionally, one or more polypeptides selected from the group consisting of a Klf4 polypeptide, a Sox2 polypeptide and a c-Myc polypeptide;
    (b) limiting the expression of endogenous Nanog in the cells from step (a) to a level substantially lower than the level of expression of endogenous Nanog in an induced pluripotent cell (iPSC), thereby generating a non-pluripotent intermediate cell;
(c) contacting the non-pluripotent intermediate cell with a GSK-3 inhibitor, an HDAC inhibitor, and a TGFβ/Activin/Nodal family member under conditions to generate an iDE cell; and
(d) under conditions to generate the pancreatic beta cell,
  (1) contacting the iDE cell with FGF7, RA, a Hedgehog pathway inhibitor, a BMP inhibitor, and a TGFβ/ALK5 receptor inhibitor;
  (2) contacting the cell of step (d)(1) with EGF and a Notch inhibitor; and
  (3) contacting the cell of step (d)(2) with bFGF and nicotinamide; thereby differentiating the non-pluripotent animal cell into the pancreatic beta cell.

23. The method of claim 22, wherein step (d) further comprises contacting with extendin 4.

\* \* \* \* \*